US009944978B2

(12) United States Patent
Harley et al.

(10) Patent No.: US 9,944,978 B2
(45) Date of Patent: Apr. 17, 2018

(54) MULTIPLEX QUANTITATIVE PCR

(71) Applicant: Telomere Diagnostics, Inc., Menlo Park, CA (US)

(72) Inventors: Calvin Harley, Murphys, CA (US); Jue Lin, Foster City, CA (US); Karl Guegler, Menlo Park, CA (US)

(73) Assignee: TELOMERE DIAGNOSTICS, INC., Menlo Park, CA (US)

( * ) Notice: Subject to any disclaimer, the term of this patent is extended or adjusted under 35 U.S.C. 154(b) by 60 days.

(21) Appl. No.: 14/746,437

(22) Filed: Jun. 22, 2015

(65) Prior Publication Data

US 2016/0186250 A1 Jun. 30, 2016

Related U.S. Application Data

(60) Provisional application No. 62/098,057, filed on Dec. 30, 2014, provisional application No. 62/163,434, filed on May 19, 2015.

(51) Int. Cl.
| | | |
|---|---|---|
| *C12P 19/34* | (2006.01) | |
| *C12Q 1/68* | (2018.01) | |
| *A61K 35/28* | (2015.01) | |
| *A61K 31/40* | (2006.01) | |
| *A61K 35/12* | (2015.01) | |

(52) U.S. Cl.
CPC ............ *C12Q 1/6851* (2013.01); *A61K 31/40* (2013.01); *A61K 35/28* (2013.01); *C12Q 1/686* (2013.01); *A61K 2035/124* (2013.01)

(58) Field of Classification Search
CPC .............. C12C 1/686; C12C 2525/151; C12C 2525/161; C12C 2525/186; C12C 2525/197; C12C 2525/204; C12C 2537/16; C12C 2545/113; C12C 2563/107; C12C 2565/102; C12C 1/6851; A61K 2035/124; A61K 35/28
USPC ...................................................... 435/91.2
See application file for complete search history.

(56) References Cited

U.S. PATENT DOCUMENTS

| | | | |
|---|---|---|---|
| 4,280,992 A | 7/1981 | Sugiura et al. | |
| 4,469,863 A | 9/1984 | T'so et al. | |
| 4,683,195 A | 7/1987 | Mullis et al. | |
| 4,683,202 A | 7/1987 | Mullis | |
| 5,034,506 A | 7/1991 | Summerton et al. | |
| 5,216,141 A | 6/1993 | Benner | |
| 5,235,033 A | 8/1993 | Summerton et al. | |
| 5,386,023 A | 1/1995 | Sanghvi et al. | |
| 5,489,508 A | 2/1996 | West et al. | 435/6 |
| 5,602,240 A | 2/1997 | De Mesmaeker et al. | |
| 5,637,684 A | 6/1997 | Cook et al. | |
| 5,644,048 A | 7/1997 | Yau | 536/25.3 |
| 5,686,245 A | 11/1997 | West | 435/6 |
| 5,741,677 A | 4/1998 | Kozlowski | 435/91.2 |
| 5,741,678 A | 4/1998 | Ronai | 435/912 |
| 5,834,193 A | 11/1998 | Kozlowski et al. | |
| 5,856,096 A | 1/1999 | Windle et al. | |
| 5,910,122 A | 6/1999 | D'Angelo | |
| 5,928,916 A | 7/1999 | Keogh | |
| 5,945,319 A | 8/1999 | Keogh | |
| 6,020,124 A | 2/2000 | Sorenson | 435/6 |
| 6,022,326 A | 2/2000 | Tatum et al. | |
| 6,436,677 B1 | 8/2002 | Gu | 435/183 |
| 6,444,261 B1 | 9/2002 | Plaksine et al. | |
| 6,514,693 B1 | 2/2003 | Lansdorp | |
| 6,919,200 B2 | 7/2005 | Ibrahim | |
| 7,482,116 B2 | 1/2009 | Birnboim | |
| 7,557,190 B2 | 7/2009 | Barbosa et al. | |
| 7,601,521 B2 | 10/2009 | Sidransky | |
| 7,695,904 B2 | 4/2010 | Cawthon | 435/6 |
| 8,025,849 B2 | 9/2011 | Baldwin et al. | |
| 8,039,215 B2 | 10/2011 | Higuchi et al. | 435/6.12 |
| 8,048,631 B2 | 11/2011 | Cawthon | 435/6.12 |
| 8,221,381 B2 | 7/2012 | Muir et al. | |
| 8,318,911 B2 | 11/2012 | Anastasi et al. | |

(Continued)

FOREIGN PATENT DOCUMENTS

| | | |
|---|---|---|
| AU | 2003208902 | 1/2003 |
| AU | 2003208902 | 11/2008 |

(Continued)

OTHER PUBLICATIONS

Marchant, "Spit test offers guide to health," Nature News: Q&A Published online May 28, 2011. http://www.nature.com/news/2011/110528/full/news.2011.330.html.
Office Action dated Jul. 29, 2016 by Taiwan Patent Office for TW Application No. 101151332, which was filed on Dec. 28, 2012 and published as 201343919, filed on Nov. 1, 2013 (Inventor—Calvin Harley; Applicant—Telome Health, Inc.) (Original—10 pages; Translation—10 pages).
Third Office Action dated Mar. 18, 2016 by State Intellectual Property Office of the People's Republic of China for Application No. 2012800689920, which was filed on Dec. 31, 2011 and published as 104105798, filed on Oct. 15, 2014 (Inventor—Calvin Harley; Applicant—Telome Health, Inc.) (Original—3 pages; Translation—6 Pages).
U.S. Appl. No. 61/139,890, filed Dec. 22, 2008, R. Cawthon.
U.S. Appl. No. 13/141,429, filed Dec. 22, 2008, R. Cawthon.
U.S. Appl. No. 60/353,591, filed Jan. 31, 2002, R. Cawthon.
U.S. Appl. No. 10/355,626 (U.S. Pat. No. 7,695,904), filed Jan. 31, 2003, R. Cawthon.

(Continued)

*Primary Examiner* — Cynthia B Wilder
(74) *Attorney, Agent, or Firm* — Ballard Spahr LLP

(57) ABSTRACT

Disclosed are methods and compositions for determining the average length or abundance of a first target nucleic by calculating the abundance of a first target nucleic acid (T) relative to the average abundance (S) of a second and a third target nucleic acid, in a single well using a separate detection label for each target nucleic acid. In various aspects, the first target nucleic acid is a telomere. In exemplary aspects, the disclosed methods and compositions can be used to determine the average telomere length in a biological sample. The average telomere length determined using the disclosed methods and compositions can be correlated to a variety of clinically important conditions and indices. This abstract is intended as a scanning tool for purposes of searching in the particular art and is not intended to be limiting of the present invention.

16 Claims, 33 Drawing Sheets

(56) References Cited

U.S. PATENT DOCUMENTS

| | | | |
|---|---|---|---|
| 9,169,516 | B2 | 10/2015 | Cawthon |
| 2003/0162209 | A1 | 8/2003 | Martin .............................. 435/6 |
| 2003/0162266 | A1 | 8/2003 | Cawthon .......................... 435/6 |
| 2004/0175733 | A1 | 9/2004 | Andersen et al. ................ 435/6 |
| 2004/0265815 | A1 | 12/2004 | Baird |
| 2005/0009097 | A1 | 1/2005 | Better et al. |
| 2006/0141492 | A1 | 6/2006 | Sowers et al. ................... 435/6 |
| 2006/0210980 | A1 | 9/2006 | Cawthon .......................... 435/6 |
| 2007/0161031 | A1 | 7/2007 | Trinklein et al. ................ 435/6 |
| 2007/0274982 | A1 | 11/2007 | Peters et al. |
| 2008/0063628 | A1 | 3/2008 | Davis et al. |
| 2009/0142408 | A1 | 6/2009 | Lin et al. |
| 2010/0010064 | A1 | 1/2010 | Moore et al. |
| 2010/0124744 | A1* | 5/2010 | Will ..................... C12Q 1/6818 435/6.11 |
| 2010/0151477 | A1 | 6/2010 | Cawthon .......................... 435/6 |
| 2010/0273675 | A1 | 10/2010 | Balis et al. ...................... 435/6 |
| 2010/0311954 | A1 | 12/2010 | Chamberlain et al. |
| 2011/0182862 | A1 | 7/2011 | Green et al. |
| 2011/0207128 | A1 | 8/2011 | Cawthon .......................... 435/6 |
| 2011/0212002 | A1 | 9/2011 | Curry et al. |
| 2011/0244462 | A1 | 10/2011 | Bendix et al. |
| 2011/0294676 | A1* | 12/2011 | Cawthon .............. C12Q 1/6851 506/7 |
| 2011/0296543 | A1 | 12/2011 | Chang et al. |
| 2012/0252014 | A1 | 10/2012 | Loeffert et al. |
| 2013/0011918 | A1 | 1/2013 | West et al. |
| 2014/0248622 | A1 | 9/2014 | Wang et al. |
| 2014/0370505 | A1 | 12/2014 | Harley |

FOREIGN PATENT DOCUMENTS

| | | |
|---|---|---|
| AU | 2009329987 | 12/2009 |
| AU | 2009329987 | 6/2011 |
| AU | 2012362210 | 12/2012 |
| CA | 2474468 | 1/2003 |
| CA | 2513747 | 1/2004 |
| CA | 2513747 | 8/2004 |
| CA | 2748265 | 12/2009 |
| CA | 2748265 | 6/2011 |
| CA | 2474468 | 3/2014 |
| CN | 03804867.1 | 1/2003 |
| CN | 1639352 | 7/2005 |
| CN | 201188066 Y | 1/2009 |
| CN | 2009801572698 | 12/2009 |
| CN | 102439171 | 8/2011 |
| CN | 2012800689920 | 12/2012 |
| CN | 104105798 | 10/2014 |
| EP | 0155747 | 9/1985 |
| EP | 03707624.7 | 1/2003 |
| EP | 04705326.9 | 1/2004 |
| EP | 1476561 | 11/2004 |
| EP | 1585974 | 10/2005 |
| EP | 09804177.5 | 12/2009 |
| EP | 2325619 | 5/2011 |
| EP | 2379747 | 7/2011 |
| EP | 12152681.8 | 1/2012 |
| EP | 2474822 | 7/2012 |
| EP | 12863843.4 | 12/2012 |
| EP | 2798091 | 11/2014 |
| HK | 05103554.7 | 1/2003 |
| HK | 1169681 | 7/2010 |
| HK | 1072275 | 8/2012 |
| HK | 1169683 | 10/2012 |
| HK | 12110505.3 | 10/2012 |
| HK | 13100352.7 | 1/2013 |
| HK | 1173218 | 5/2013 |
| HK | 15103294.0 | 4/2015 |
| HK | 10202593 | 10/2015 |
| JP | 09-206081 A | 8/1997 |
| JP | 2003-564211 | 1/2003 |
| JP | 2006-503063 | 1/2004 |
| JP | 2004-533801 | 11/2004 |
| JP | 2005-027518 | 2/2005 |
| JP | 5686493 | 7/2006 |
| JP | 2011-543646 | 12/2009 |
| JP | 2012-513215 | 12/2009 |
| JP | 2015-175632 | 12/2009 |
| JP | 4515767 | 8/2010 |
| TW | 101151332 | 12/2012 |
| TW | 201343919 | 11/2013 |
| WO | WO 1996/041016 | 12/1996 |
| WO | WO 1997/012681 | 4/1997 |
| WO | WO 1999/046408 | 9/1999 |
| WO | WO 2000/030753 | 6/2000 |
| WO | WO 2001/040462 | 6/2001 |
| WO | WO 2001/066799 | 9/2001 |
| WO | PCT/US2003/002844 | 1/2003 |
| WO | WO 2003/064615 | 8/2003 |
| WO | PCT/US2004/002215 | 1/2004 |
| WO | WO 2004/068110 | 8/2004 |
| WO | WO 2006/110735 | 10/2006 |
| WO | PCT/US2009/069243 | 12/2009 |
| WO | WO 2010/075413 | 7/2010 |
| WO | PCT/US2012/072131 | 12/2012 |
| WO | WO 2013/102116 | 4/2013 |
| WO | PCT/US2014/039110 | 5/2014 |
| WO | WO 2014/190138 | 5/2014 |
| WO | PCT/US2015/036991 | 6/2015 |

OTHER PUBLICATIONS

U.S. Appl. No. 12/700,475 (U.S. Pat. No. 8,048,631), filed Jan. 31, 2002, R. Cawthon.
U.S. Appl. No. 60/442,456, filed Jan. 24, 2003, R. Cawthon.
U.S. Appl. No. 10/543,111 (U.S. Pat. No. 9,169,516), filed Jan. 26, 2004 (Oct. 27, 2015), R. Cawthon.
U.S. Appl. No. 61/304,958, filed Feb. 16, 2010, R. Cawthon.
U.S. Appl. No. 13/028,910, filed Feb. 16, 2011, R. Cawthon.
U.S. Appl. No. 61/826,484, filed May 22, 2013, C. Harley et al.
U.S. Appl. No. 14/892,395, C. Harley et al.
U.S. Appl. No. 61/581,835, filed Dec. 30, 2011, C. Harley.
U.S. Appl. No. 61/582,261, filed Dec. 31, 2011, C. Harley.
U.S. Appl. No. 14/370,005 (US 2014/0370505), filed Dec. 28, 2012 (Dec. 18, 2014), C. Harley.
U.S. Appl. No. 62/098,057, filed Dec. 30, 2014, C. Harley et al.
U.S. Appl. No. 62/163,434, filed May 19, 2015, C. Harley et al.
Final Rejection dated Jul. 12, 2016 by the U.S. Patent and Trademark Office for U.S. Appl. No. 14/370,005, filed Dec. 28, 2012 and published as US-2014-0370505-A1 on Dec. 18, 2014 (Inventor—Calvin Harley et al)(8 Pages).
Adaikalakoteswari, A. et al., Association of Telomere Shortening with Impaired Glucose Tolerance and Diabetic Maccoangiopathy, Atherosclerosis, 195: 83-9 (2007).
Alder, J.K. et al., Short Telomeres are a Risk Factor for Idiopathic Pulmonary Fibrosis, Proc Natl Acad Sci USA, 105(35): 13051-6 (2008).
Allshire, R.C. et al., Human Telomeres Contain at Least Three Types of G-Rich Repeat Distributed Non-Randomly, Nucleic Acids Res, 17(12): 4611-27 (1989).
Allsopp, R.C. et al., Telomere Length Predicts Replicative Capacity of Human Fibroblasts, Proc Natl Acad Sci USA, 89(21): 10114-8 (1992).
Almasy L, et al. (1998) Multipoint quantitative-trait linkage analysis in general pedigrees. Am J Hum Genet. 62: 1198-211.
Aps, J.K.M. et al., Flow Cytometry as a New Method to Quanitfy the Cellular Content of Human Saliva and Its Relation to Gingivitis, Clinica Chimica Acta, 321(1-2): 35-41 (2002).
Asai, A. et al., A Novel Telomerase Template Antagonist (GRN163) as a Potential Anticancer Agent, Cancer Res, 63: 3931-9 (2003).
Austriaco, Jr. et al., Changes of Telomere Length Cause Reciprocal Changes in the Lifespan of Mother Cells in *Saccharomyces cerevisiae*, Proc Natl Acad Sci USA, 94: 9768-72 (1997).
Baerlocher, G. and P. Lansdorp, Telomere Length Measurements in Leukocyte Subsets by Automated Multicolor Flow FISH, Cytometry, 55: 1-6 (2003).
Baerlocher, G. et al., Flow Cytometry and FISH to Measure the Average Length of Telomeres (flow FISH), Nature Protocols, 1(5): 2365-76 (2006).

(56) References Cited

OTHER PUBLICATIONS

Baerlocher, G. et al., Telomere Length Measurement by Fluorescence in Situ Hybridzation and Flow Cytometry: Tips and Pitfalls, Cytometry, 47: 89-99 (2002).
Baird, D.M. et al., Extensive Allelic Variation and Ultrashort Telomeres in Senescent Human Cells, Nat Genet, 33(2): 203-7 (2003).
Baird, D.M. et al., Mechanisms Underlying Telomere Repeat Turnover, revealed by Hypervariable Variant Repeat Distribution Patterns in the Human Xp/Yp Telomere, EMBO J, 14(21): 5433-43 (1995).
Bakaysa, S.L. et al. (2007) Telomere length predicts survival independent of genetic influences, Aging Cell, 6(6): 769-74.
Baldino, F.J. et al., High-Resolution in situ Hybridization Histochemistry, Methods Enzymology, 168: 761-77 (1989).
Beaucage, S.L. and P.I. Radhakrishnan, The Functionalization of Oligonucleotides via Phosphoramidite Derivatives, Tetrahedron, 49(10): 1925-63 (1993).
Bechter, O.E. et al., Telomere Length and Telomere Activity Predict Survival in Patients with B Cell Chronic Lymphocytic Leukemia, Cancer Res, 58(21): 4918-22 (1998).
Beekman M, et al. (2006) Chromosome 4q25, microsomal transfer protein gene, and human longevity: novel data and a meta-analysis of association studies, J Gerontol A Biol Sci Med Sci, 61(4): 355-62.
Bendix et al., Longitudinal Changes in Leukocyte Telomere Length and Mortality in Humans, J Gernotol A Biol Sci Med Sci, 69(2): 231-9 (2014).
Bessler, M. et al., Dysfunctional Telomeres and Dsykeratosis Congenita, Haematologica, 92(8): 1009-12 (2007).
Blasco, M.A. et al. (1997) Telomere shortening and tumor formation by mouse cells lacking telomerase RNA, Cell, 91(1): 25-34.
Boulay, J.L. et al. (1999) Gene dosage by quantitative real-time PCR. Biotechniques. 27(2): 228-30, 232.
Bray, P. et al., Human cDNA Clones for Four Species of $G_\alpha$ Signal Tranduction Protein, Proc Natl Acad Sci USA, 83(23): 8893-7 (1986).
Brill, W.K.D. et al., Synthesis of Oligodeoxynucleoside Phosphorodithioates via Thioamidites, J Am Chem Soc, 111(6): 2321-2 (1989).
Brouilette, S.W. et al., Telomere Length, Risk of Coronary Heart Disease, and Stain Treatment in the West of Scotland Primary Prevention Study: A Nested Case-Control Study, Lancet, 369: 107-14 (2007).
Brouilette, S.W. et al., White Cell Telomere Length and Risk of Premature Myocardial Infarction, Arteriscler Throm Vasc Biol, 23: 842-6 (2003).
Brown, M.D. et al. (2006) IQGAP1 in cellular signaling: bridging the GAP. Trends Cell Biol. 16(5): 242-9.
Brummendorf et al., Telomere Length in Leukocyte Subpopulations of Patients with Aplastic Anemia, Blood, 97(4): 895-900 (2001).
Calado, R.T. and N.S. Young, Telomeres, telomerase, and Human Disease, The Hematologist, 7(1): 7 (2010).
Canela, A. et al., High-Throughput Telomere Length Quantification by FISH and Its Application to Human Population Studies, Proc Natl Acad Sci USA, 104(13): 5300-5 (2007).
Capezzone, M. et al., Short Telomeres, Telomerase Reverse Transcriptase Gene Amplification, and Increased Telomerase Activity in the Blood of Familial Papillary Thyroid Cancer Patients, J Clin Endocrinol Metab, 93(10): 3950-7 (2008).
Cariello, N.F. et al., Fidelity of Thermococcus litoralis DNA Polymerase (Vent) in PCR Determined by Denaturing Gradient Gel Electrophoresis, Nucleic Acids Res, 19(15): 4193-8 (1991).
Carlsson, C. et al., Screening for Genetic Mutations, Nature, 380(6571): 207 (1996).
Cawthon RM, et al. (2003) Association between telomere length in blood and mortality in people aged 60 years or older. Lancet. 361: 393-5.
Cawthon RM. (2002) Telomere measurement by quantitative PCR. Nucleic Acids Res. 30(10): e47.

Cawthon RM. (2009) Telomere length measurement by a novel monochrome multiplex quantitative PCR method. Nucleic Acids Res. 37(3): e21.
Challacombe, S.J. and J.R. Naglik, The Effects of HIV Infection on Oral Mucosal Immunity, Adv Dental res, 19: 29-35 (2006).
Chang et al., Telomere Length and Replicative Aging in Human Vascular Tissues, Proc Natl Acad Sci USA, 92: 11190-4 (1995).
Cherif et al., Ageing and Telomeres: A Study into Organ and Gender-Specific Telomere Shortening, Nucleic Acids Res, 31(5): 1576-83 (2003).
Cheung, V.G. et al. (2002) The genetics of variation in gene expression. Nat Genet. 32 Suppl: 522-5.
Cheung VG, et al. (2003) Natural variation in human gene expression assessed in lymphoblastoid cells. Nat Genet. 33: 422-5.
Cheung VG, et al. (2005) Mapping determinants of human gene expression by regional and genome-wide association. Nature. 437(7063): 1365-9.
Chien, A. et al., Deoxyribonucleic Acid Polymerase from the Extreme Thermophile *Thermus aquaticus*, J Bacteriol, 127(3): 1550-7 (1976).
Christensen, K. et al., The Quest for Genetic Determinants of Human Longevity: Challenges and Insights, Nature Reviews Genetics, 7: 436-48 (2006).
Cohen, S. et al., A Global Measure of Perceived Stress, J Health Soc Behav, 24(4): 385-96 (1983).
Cronkhite, J.T. et al., Telomere Shortening in Familial and Spradic Pulmonary Fibrosis, Am J Resp Crit Care Med, 178: 729-37 (2008).
D'Aquila, R.T. et al. (1991) Maximizing sensitivity and specificity of PCR by pre-amplification heating. Nucleic Acid Research. 19(13): 3749.
Dai M, et al. (2005) Evolving gene/transcript definitions significantly alter the interpretation of GeneChip data. Nucleic Acids Res. 33(20): e175.
Dausset J, et al. (1990) Centre d'etude du polymorphisme humain (CEPH): collaborative genetic mapping of the human genome. Genomics. 6(3): 575-577.
De Mesmaeker, A. et al., Comparison of Rigid and Flexible Backbones in Antisense Oligonucleotides, Bioorganic & Medicinal Chem Lett, 4(3): 395-8 (1994).
Dempcy, R.O. et al., Synthesis of a Thymidyl Pentamer of Deoxyribonucleic Guanidine and Bunding Studies with DNA Homopolynucleotides, Proc Natl Acad Sci USA, 92(13): 6097-101 (1995).
Diaz, R.S. and E.C. Sabino, Accuracy of Replication in the Polymerase Chain Reaction. Comparison Between *Thermotoga maritima* DNA Polymerase and *Thermos aquaticus* DNA Polymerase, Braz J Med Res, 31(10): 1239-42 (1998).
Dixon AL, et al. (2007) A genome-wide association study of global gene expression. Nat Genet. 39(10): 1202-7.
Don, R.H. et al.(1991) 'Touchdown' PCR to circumvent spurious priming during gene amplification. Nucleic Acid Research. 19(14): 4008.
Dustin, M.L. (2006) Immunology. When F-actin becomes too much of a good thing. Science. 313(5788): 767-8.
Effros, R.B. et al., Shortened Telomeres in the Expanded CD28-CD8+ Cell Subset in HIV Disease Implicate Replicative Senescence in HIV Pathogenesis, AIDS, 10(8): F17-22 (1996).
Effros, R.B. et al., Telomere/Telomerase Dynamics Within the Human Immune System: Effect of Chronic Infection and Stress, Exp Gerontol, 46(2-3): 135-40 (2011).
Efron B, et al. (2004) Least angle regression. Ann Statist. 32(2): 407-99.
Efron B, et al. (2007) on testing the significance of sets of genes. Ann Appl Stat. 1(1): 107-29.
Egholm, M. et al., Peptide Nucleic Acids (PNA). Oligonucleotide Analogs with an Achiral Peptide Backbone, J Am Chem Soc, 114(5): 1895-7 (1992).
Egholm, M. et al., PNA Hybridizes to Complementary Oligonucleotides Obeying the Watson-Crick Hydrogen-Bonding Rules, Nature, 365(6446): 566-8 (1993).

(56) References Cited

OTHER PUBLICATIONS

Ehrlenbach, S. et al. (2009) Influences on the reduction of relative telomere length over 10 years in the population-based Bruneck study: introduction of a well-controlled high-throughput assay. Intl. J. Epidemol. (38): 1725-1734.
Epel, E.S. et al., Accelerated Telomere Shortening in Response to Life Stress, Proc Natl Acad Sci USA, 101(49): 17312-5 (2004).
Fan, J. et al., Detection of a Novel Avian Influenza A (H7N9) Virus in Humans by Multiplex One-Step Real-Time RT-PCR Assay, BMC Infectious Diseases, 14: 541 (9 pages) (2014).
Farzaneh-Far, R. et al., Telomere Length Trajectory and Its Determinants in Persons with Coronary Asrtery Disease: Longitudinal Findings from the Heart and Soul Study, PloS One, 5(1): e8612 (7 pages) (2010).
Fitzpatrick, A.L. et al. (2011) Leukocyte telomere length and mortality in the cardiovascular health study. J. Gerontol. A. Biol. Sci. Med. Sci. 66A(4): 421-9.
Föger, N. et al. (2006) Requirement for coronin 1 in T lymphocyte trafficking and cellular homeostasis. Science. 313: 839-42.
Frank, I.E. et al.(1993) A statistical view of some chemometrics regression tools (with discussion). Technometrics. 35: 109-48.
Frenck et al., The Rate of Telomere Sequence Loss in Human Leukocytes Caries with Age, Proc Natl Acad Sci USA, 95: 5607-10 (1998).
Fyhrquist, F. and O. Saijonma, Telomere Length and Cardiovascular Aging, Ann Med, 44(Suppl 1): S138-42 (2012).
Geesaman, B.J. et al. (2003) Haplotype-based identification of a microsomal transfer protein marker associated with the human lifespan. Proc Natl Acad Sci USA. 100(24): 14115-20.
Gertsch J., et al., "Relative quantification of mRNA levels in Jurkat T cells with RT-real time-PCR (RT-rt-PCR): New possibilities for the screening of anti-inflammatory and cytotoxic compounds," *Pharm Res.*, 19(8): 1236-43 (2002).
Göring, H.H. et al. (2007) Discovery of expression QTLs using large-scale transcriptional profiling in human lymphocytes. Nat Genet. 39(10): 1208-16.
Griffith et al., Mammalian Telomeres End in a Large Duplex Loop, Cell, 97: 503-14 (1999).
Gudnason, H. et al., Comparison of Multiple DNA Dyes for Real-Time PCR: Effects of Dye Concentration and Sequence Composition on DNA Amplification and Melting Temperature, Nucleic Acids Res, 35(19): e127 (2007) (8 pages).
Hamilton, B. et al. (2005) A systematic RNAi screen for longevity genes in C. elegans. Genes Dev. 19(13): 1544-55.
Haraldsson, M.K. et al. (2008) The lupus-related Lmb3 locus contains a disease-suppressing Coronin-1A gene mutation. Immunity. 28: 40-51.
Harley, C.B. et al., A Natural Product Telomerase Activator as Part of a Health Maintenance Program, Rejuvenation Res, 14(1): 45-56 (2011).
Harley CB, et al. (1990) Telomeres shorten during ageing of human fibroblasts. Nature. 345(6274): 458-60.
Harris et al., The Association Between Telomere Length, Physical Health, Cognitive Ageing, and Mortality in Non-Demented Older People, Neuroscience Lett, 406: 260-4 (2006).
Harrison, D., Oxidative stress and coronary artery disease, Can J Cardiol, 14(suppl D): 30D-2D (1998).
Heacock et al., Molecular Analysis of Telomere Fusions in *Arabidopsis*: Multiple Pathways for Chromosome End-Joining, EMBO J, 23(11): 2304-13 (2004).
Hemann, M.T. et al., The Shortest Telomere, Not Average Telomere Length, is Critical for Cell Viability and Chromosome Stability, Cell, 107(1): 67-77 (2001).
Henderson, S. et al. (1996) In situ analysis of changes in telomere size during replicative aging and cell transformation. J. Cell Biol. 134(1): 1-12.
Herrera E, et al. (1999) Disease states associated with telomerase deficiency appear earlier in mice with short telomeres. EMBO J. 18(11): 2950-2960.
Higuchi R, et al. (1993) Kinetic PCR analysis: real-time monitoring of DNA amplification reactions. Biotechnology (NY). 11(9): 1026-1030.
Hoare, M. et al., CD4+ T-Lymphocyte Telomere Length is Related to Fibrosis Stage, Clinical Outcome and Treatement Response in Chronic Hepititis C Virus Infection, J Hepatol, 53(2): 252-60 (2010).
Hoerl AE, et al. (2000) Ridge regression: Biased estimation for nonorthogonal problems. Technometrics. 41: 80-86.
Hukezalie, K.R. et al., In Vitro and Ex Vivo Inhibition of Human Telomerase by Anti-HIV Nucleotide Reverse Transcriptase Inhibitors (NRTIs) but Not by Non-NRTIs, PLoS One, 7(11): e47505 (2012).
Hultdin M, et al. (1998) Telomere analysis by fluorescence in situ hybridization and flow cytometry. Nucleic Acids Res. 26(16): 3651-3656.
Jeanclos, E., et al., Shortened telomere length in white blood cells of patients with IDDM, Diabetes, 47: 482-86 (1998).
Jeffs, P.W. and X. Gao, Unusual Conformation of a 3'-Thioformacetal Linkage in a DNA Duplex, J Biomolecular NMR, 4(1): 17-34 (1994).
Jenkins, G.N. and N.J. Turner, The Biosynthesis of Carbocyclic Nucleosides, Chem Soc Rev, 24: 169-76 (1995).
Johnson MR, et al. (2000) Quantitation of dihydropyrimidine dehydrogenase expression by real-time reverse transcription polymerase chain reaction. Anal Biochem. 278(2): 175-184.
Joneja, A. and X. Huang, Linear Nicking Endonuclease-Mediated Strand-Displacement DNA Amplification, Anal Biochem, 414(1): 58-69 (2011).
Jyonouchi, S., et al., "Dyskeratosis congenita: a combined immunodeficiency with broad clinical spectrum—a single-center pediatric experience," Pediatr Allergy Immunol, 22(3): 313-9 (2011).
Kainz P. (2000) The PCR plateau phase—towards an understanding of its limitations. Biochim Biophys Acta. 1494: 23-27.
Kerber RA et al. (2001) Familial excess longevity in Utah genealogies. J Gerontol A Biol Sci Med Sci. 56: B130-139.
Kerber RA, et al. (2009) Gene expression profiles associated with aging and mortality in humans. Aging Cell. 8(3): 239-250.
Kim et al., Specific Association of Human Telomerase Activity with Immortal Cells and Cancer, Science, 266: 2011-5 (1994).
Kimura, M. et al. (2008) Telomere length and mortality: a study of leukocytes in elderly Danish twins. Am. J. Epidemol. 167(7): 799-806.
Kimura, M. et al., Measurement of telomere length by the Southern blot analysis of terminal restriction fragment lengths, Nature Proctocols, 5(9): 1596-607 (2010).
Kimura, M. and A. Aviv, Measurement of Telomere DNA Content by Dot Blot Analysis, Nucleic Acids Res, 39(12): e84 (2011).
Koppal, T., "DNA Sequencing: Getting to the $1,000 Genome—DNA sequencing technologies strive for higher throughputs and lower costs," *Lab Manager*, 4(4): 46-47 (2009).
Kuniaki, A. et al. (2002) Two independent regions of human telomerase reverse transcriptase are important for its oligomerization and telomerase activity. J. Biol. Chem. 277(10): 8538-8544.
Kuramoto, M. et al. (2001) Identification and analyses of the Xenopus TERT gene that encodes the catalytic subunit of telomerase. Gene. 277: 101-110.
Lawyer FC, et al. (1993) High-level expression, purification, and enzymatic characterization of full-length Thermus aquaticus DNA polymerase and a truncated form deficient in 5' to 3' exonuclease activity. PCR Methods Appl. 2(4): 275-287.
Lecomte, Ph.J. and O.P. Doubleday, Selective Inactivation of the 3' to 5' Exonndease Activity of *Escherichia coli* DNA Polymerase I by Beat, Nucleic Acids Res, 11(21):7505 (1983).
Letsinger, R.L. and W.S. Mungall, Phosphoramidate Analogs of Oligonucleotides, J Org Chem, 35(11): 3800-3 (1970).
Letsinger, R.L. et al., Effects of Pendant Groups at Phosphorus on Binding Properties of d-ApA Analogues, Nucleic Acids Res, 14(8): 3487-99 (1986).
Letsinger, R.L. et al., Cationic Olgionucleotides, J Am Chem Soc, 110(13): 4470-1 (1988).

(56) References Cited

OTHER PUBLICATIONS

Letsinger, R.L. et al., Hybridization of Alternationg Cationic/Anionic Oligonucleotides to RNA Segments, Nucleosides and Nucleotides, 13(6-7): 1597-605 (1994).
Li, B. et al. (2003) Rap1 affects the length and heterogeneity of human telomeres. Mol Biol Cell. 14(12): 5060-8.
Lin, J. et al., Analyses and Comparisons of Telomerase Activity and Telomere Length in Human T and B Cells: Insights for Epidemiology of Telomere Maintenance, J Immunol Methods, 352(1-2): 71-80 (2010).
Liu, H. et al. (2007) AffyProbeMiner: a web resource for computing or retrieving accurately redefined Affymetrix probe sets. Bioinformatics. 23: 2385-90.
Liu, W.M. et al. (2002) Analysis of high density expression microarrays with signed-rank call algorithms. Bioinformatics. 18(12): 1593-9.
Liu, J. et al., Longer Leukocyte Telomere Length Predicts Increased Risk of Hepititis B Virus-Related Hepatocellular Carcinoma: A Case Analysis, 117(18): 4247-56 (2011).
Löffert, D. et al. (1997) PCR optimization: primer design. Qiagen News. 5: 3-6.
Lundberg, K.S. et al., High-Fidelity Amplification Using a Thermostable DNA Polymerase Isolated from Pyrococcus fuiosus, Gene, 108(1): 1-6 (1991).
Lunetta KL, et al. (2007) Genetic correlates of longevity and selected age-related phenotypes: a genome-wide association study in the Framingham Study. BMC Med Genet. 8 Suppl 1: S13.
Ma, H. et al., Shortened Telomere Length Is Associated with Increased Risk of Cancer: A Meta-Analysis, PLoS One, 6(6): e20466, (2011).
Mag, M. et al., Synthesis and Slective Cleavage of an Oligodeoxynucleotide Containing a Bridged Internucleotide 5'-Phosphorothioate Linkage, Nucleic Acids Res, 19(7): 1437-41 (1991).
Martin-Ruiz, C.M. et al., Reproducibility of Telomere Length Assessment: an International Collaborative Study, Int J Epidemiol, doi: 10.1093/ije/dyu191 (2014).
Marullo M. et al., Expressed Alu Repeats as a Novel, Reliable Tool for Normalization of Real-Time Quantitative RT-PCR Data, Genome Biol, 11(1): R9 (1-12) (2010).
Masaki, Y. et al. (2002) Telomerase activity detected in eyed embryos of rainbow trout Oncorhynchus mykiss. Fisheries Science. 68: 132-7.
Mather, K.A. et al. (2010) Is telomere length a biomarker of aging? A review. J. Gerontol. A. Biol. Sci. Med. Sci. 66A(2): 202-13.
Mathers, J.C. (2006) Nutritional modulation of ageing: genomic and epigenetic approaches. Mech Ageing Dev. 127(6): 584-9.
Mecham, B.H. et al. (2004) Sequence-matched probes produce increased cross-platform consistency and more reproducible biological results in microarray-based gene expression measurements. Nucleic Acids Res. 32(9): e74.
Meier, C. and J.W. Engels, Peptide Nucleic Acids (PNAs)—Unusual Properties of Nonionic Oligonucleotide Analogues, Angew Chem Int Ed Engl, 31(8): 1008-10 (1992).
Merrill, R.M. et al. (2003) Impact of the LDS church's health doctrine on deaths from diseases and conditions associated with cigarette smoking. Ann Epidemiol. 13(10): 704-11.
Monks, S.A. et al.(2004) Genetic inheritance of gene expression in human cell lines. Am J Hum Genet. 75(6): 1094-105.
Morley, M. et al. (2004) Genetic analysis of genome-wide variation in human gene expression. Nature. 430(7001): 743-7.
Morrison, T.B. et al. (1998) Quantification of low-copy transcripts by continuous SYBR Green I monitoring during amplification. Biotechniques. 24(6): 954-8, 960, 962.
Mueller, P. et al. (2008) Regulation of T cell survival through coronin-1-mediated generation of inositol-1,4,5-trisphosphate and calcium mobilization after T cell receptor triggering. Nat Immunol. 9(4): 424-31.
Munoz-Jordan et al., T-Loops at Trypanosome Telomeres, EMBO J, 20: 579-88 (2001).

Myers, T.W. and D.H. Gelfand, Reverse Transcription and DNA Amplification by a Thermus Thermophilus DNA Polymerase, Biochemistry, 30(31): 7661-6 (1991).
Nakayama, J.I. et al. (2002-03) Stretch PCR Assay. Methods in Molecular Biology. 191: 125-36.
Nebel A, et al. (2005) No association between microsomal triglyceride transfer protein (MTP) haplotype and longevity in humans. Proc Natl Acad Sci USA. 102(22): 7906-9.
Nishita, D.M. et al., Clinical trial participant characteristics and saliva and DNA metrics, BMC Medical Research Methodology, 9: 71 (1-10) (2009).
Njajou, O.T. et al., Association between telomere length, specific causes of death, and years of healthy life in health, aging, and body composition, a population-based cohort study, J Gerontol A Biol Sci Med Sci, 64(8): 860-4 (2009).
Nordstrom, B. et al., Characterization of Bacteriophage T7 DNA Polymerase Purified to Homogeneity by Antithioredoxin Immunoadsorbent Chromatography, J Biol Chem, 256(6): 3112-7 (1981).
O'Callaghan, N. et al. (2008) a quantitative real-time PCR method for absolute telomere length. Biotechniques. 44(6): 807-9.
Ogata, N. et al., Idenshi Kogaku Keyword Book ("Genetic Engineering Keywords"), Yodosha, 2000' $2^{nd}$ Edition, p. 405.
Paeschke, K. et al., Telomeres: Structures in Need of Unwinding, FEBS Lett, 584(17): 3760-72 (2010).
Palmer et al., Telomere Length, Telomerase Activity, and Replicative Potential in HIV Infection: Analysis of CD4+ and CD8+ T Cells from HIV-Discordant Monozygotic Twins, J Experimental Medicine, 185(7): 1381-6 (1997).
Panossian, L.A. et al., Telomere shortening in T cells correlates with Alzheimer's disease status, Neurobiol. Aging, 24(1): 77-84 (2003).
Pommier, J.P. et al., Immunosenescence in HIV Pathogenesis, Virology, 231(1): 148-54 (1997).
Poon, S. S. et al., Telomere Length Measurements Using Digital Fluorescence Microscopy, Cytometry, 36(4): 267-78 (1999).
Powers, R.W. et al. (2006) Extension of chronological life span in yeast by decreased TOR pathway signaling. Genes Dev. 20(2): 174-84.
Puca, A.A. et al. (2001) A genome-wide scan for linkage to human exceptional longevity identifies a locus on chromosome 4. Proc Natl Acad Sci USA. 98(18): 10505-8.
Puterman, E. and E. Epel, An Intricate Dance: Life Experience, Multisystem Resiliency, and Rate of Telomere Decline Throughout the lifespan, Soc Personal Psychol Compass, 6(11): 807-25 (2012).
Rattan, S.I.S. et al., Increased Molecular Damage and Heterogeneity as the Basis of Aging, Biol Chem, 389(3): 267-72 (2008).
Reiner, A. et al. (2003) Identifying differentially expressed genes using false discovery rate controlling procedures. Bioinformatics. 19, 368-75.
Relative fluorescence unit (RFU), DNA.gov: Glossary, Apr. 2011 (found at http://web.archive.org/web/20110506061955/http://www.dna.gov/glossary#R; retrieved on Dec. 23, 2014) (1 page).
Roth, A., et al., Small Molecules in Oncology, Recent Results in Cancer Research, U.M. Martens (ed.), Springer Verlag, 2010, pp. 221-234.
Ruchaud, S. et al. (2007) Chromosomal passengers: conducting cell division. Nat Rev Mol Cell Biol. 8(10): 798-812.
Rudolph, K.L. et al. (1999) Longevity, Stress Response, and Cancer in Aging Telomerase-Deficient Mice, Cell, 96(5): 701-12.
Rufer, N. et al., Telomere Length Dynamics in Human Lymphocyte Subpopulations Measured by Flow Cytometry, Nat Biotechnol, 16(8): 743-7.
Rufer, N. et al. (1999) Telomere fluorescence measurements in granulocytes and T lymphocyte subsets point to a high turnover of hematopoietic stem cells and memory T cells in early childhood. J. Exp. Med. 190(2): 157-67.
Rychlik, W. et al., J NIH Res, 6:78 (1994).
Ryder, M.I. et al. (2004) Alteration of gene expression profiles of peripheral mononuclear blood cells by tobacco smoke: implications for periodontal diseases. Oral Microbiol Immunol. 19(1): 39-49.
Sprinzl, M. et al., Enzymatic Incorporation of ATP and CTP Analogues into the 3' End of tRNA, Eur J Biochem, 81(3): 579-89 (1977).

(56) References Cited

OTHER PUBLICATIONS

Steer, S. E. et al., Reduced telomere length in rheumatoid arthritis is independent of disease activity and duration, An. Rheum Dis, 66(4): 476-80 (2007).
Stenesh, J. and G.R. McGowan, DNA Polymerase from Mesophilic and Thermophilic Bacteria. III. Lack of Fidelity in the Replication of Synthetic Polydeoxyribonucleotides by DNA Polymerase from *Bacillus licheniforrnis* and *Bacillus stearothermophilus*, Biochim Biophys Acta, 475(1): 32-41 (1977).
Strahl, C. and E.H. Blackburn, Effects of Reverse Transcriptase Inhibitors on Telomere Length and Telomerase Activity in Two Immortalized Human Cell Lines, Mol Cell Biol, 16(1): 53-65 (1996).
Stranger, B.E. et al. (2005) Genome-Wide Associations of Gene Expression Variation in Humans. PLoS Genet 1(6): e78.
Svenson, U. et al.(2008) Breast cancer survival is associated with telomere length in peripheral blood cells. Cancer Res. 68(10): 3618-23.
Talasaz, A.H. et al., Isolating Highly Enriched Populations of Circulating Epithelial Cells and Other Rare Cells from Blood Using a Magnetic Sweeper Device, Proc Natl Acad Sci USA, 106(10): 3970-5 (2009).
Tatematsu, K. et al. (1996) A novel quantitative 'stretch PCR assay', that detects a dramatic increase in telomerase activity during the progression of myeloid leukemias. Oncogene. 13: 2265-74.
Tentolouris, N. et al., White blood cells telomere length is shorter in males with type 2 diabetes and microalbuminuria, Diabetes Care, 30(11): 2909-15 (2007).
Therneau TM. (2007) On mixed-effect Cox models, sparse matrices, and modeling data from large pedigrees. Paper presented on Dec. 31, 2007.
Tibshirani R. (1996) Regression Shrinkage and Selection via the Lasso. Journal of the Royal Statistical Society, Series B. 58(1): 267-88.
Uziel, O. et al., Telomere dynamics in arteries and mononuclear cells of diabetic patients: effect of diabetes and of glycemic control, Exper. Gerontology, 42: 971-8 (2007).
Valdes, A.M. et al., Obesity, cigarette smoking, and telomere length in women, Lancet, 366: 662-4 (2005).
Valls, C. et al., Telomere Length is a Pronostic Factor for Overall Survival in Colorectal Cancer, Colorectal Dis, 13(11): 1265-72 (2011).
van Leeuwen, D.M. et al. (2005) Differential gene expression in human peripheral blood mononuclear cells induced by cigarette smoke and its constituents. Toxicol Sci. 86(1): 200-210.
Rylander-Rudqvist T. et al., Quality and quantity of saliva DNA obtained from the self-administrated oragene method—a pilot study on the cohort of Swedish men, Cancer Epidemiol. Biomarkers Prev., 15(9): 1742-5 (2006).
Salpea, K. and S.E. Humphries, Telomere length in atherosclerosis and diabetes, Atherosclerosis, 209(1): 35-8 (2010).
Samani et al., Telomere Shortening in Atherolsclerosis, Lancet, 358: 472-3 (2001).
Sampson, M.J. and D.A. Hughes, Chromosomal telomere attrition as a mechanism for the increased risk of epithelial cancers and senescent phenotypes in type 2 diabetes, Diabetologia, 49: 1726-31 (2006).
Sanders et al., Telomere Length in Epidemiology: A Biomarker of Aging, Age-Related Disease, Both, or Neither?, Epidemiologic Reviews, 35: 112-31 (2013).
Satoh, M. et al., Effect of intensive lipidlowering therapy on telomere erosion in endothelial progenitor cells obtained from patients with coronary artery disease, Clin Sci, 116: 827-35 (2009).
Sawai, H. et al., Synthesis and Properties of Oligoadenylic Acids Conaining 2'-5' Phosphoramide Linkage, Chem Lett, 13(5): 805-8 (1984).
Schadt, E.E. et al. (2003) Genetics of gene expression surveyed in maize, mouse and man. Nature. 422(6929): 297-302.
Scheinberg, P. et al., Association of Telomere Length of Peripheral Blood Leukocytes With Hematopoietic Relapse, Malignant Transformation, and Survival in Severe Aplastic Anemia, JAMA, 304(12): 1358-64 (2010).
Segal, M.R. (2006) Microarray gene expression data with linked survival phenotypes: diffuse large-B-cell lymphoma revisited. Biostatistics. 7, (2): 268-285.
Seong, K.H. et al. (2001) Application of the gene search system to screen for longevity genes in *Drosophila*. Biogerontology. 2(3): 209-17.
Sheffield, V.C. et al. (1989) Attachment of a 40-base-pair G + C-rich sequence (GC-clamp) to genomic DNA fragments by the polymerase chain reaction results in improved detection of single-base changes. Proc Natl Acad Sci USA. 86: 232-236.
Shen, J. et al., Telomere length, oxidative damage, antioxidants and breast cancer risk, Int. J. Cancer, 124(7): 1637-43 (2009).
Shiow, L.R. et al. (2008) the actin regulator coronin 1A is mutant in a thymic egress-deficient mouse strain and in a patient with severe combined immunodeficiency. Nat Immunol. 9(11): 1307-15.
Smith, B., Rinse, Swab, or Spit—What's the Real Source of DNA in Saliva?, DNA Genotek's Sample Collection Blog (Mar. 31, 2010) From http://blog.dnagenotek.com/blogdnagenotekcom.
Southern, E.M., Detection of specific sequences among DNA fragments separated by gel electrophoresis, J. Mol. Biol., 98(3): 503-17 (1975).
Wittwer, C.T. et al. (2001) Real-time multiplex PCR assays. Methods. 25(4): 430-442.
Wolkowitz, O.M. et al., Leukocyte Telomere Length in Major Depression: Correlations with Chronicity, Inflammation and Oxidative Stress—Preliminary Findings, PLoS One, 6(3): e17837 (1-10) (2011).
Wu, Z. et al. (2005) Stochastic models inspired by hybridization theory for short oligonucleotide arrays. J Comput Biol 12(6): 882-893.
Wylie, J.E. et al. (2003) Biomedical databases: protecting privacy and promoting research. Trends Biotechnol. 21(3): 113-116.
Xu, L. and E.H. Blackburn, Human Cancer Cells Harbor T-Stumps, a Distinct Class of Extremely Short Telomeres, Mol Cell, 28(2): 315-27 (2007).
Yang, J. et al. (2007) AZD1152, a novel and selective aurora B kinase inhibitor, induces growth arrest, apoptosis, and sensitization for tubulin depolymerizing agent or topoisomerase II inhibitor in human acute leukemia cells in vitro and in vivo. Blood. 110(6): 2034-2040.
Yoon, M., et al., "Immobilization of antibodies on the self-assembled monolayer by antigen-binding site protection and immobilization kinetic control," *J. Biomed. Sci. Engr.*, 4: 242-247 (2011).
Zekry et al., Telomere Length, Comorbidity, Functional, Nutritional, and Cognitive Status as Predictors of 5 Years Post Hospital Discharge Survival in the Oldest Old, J Nutr Health Aging, 16(3): 225-30 (2012) (Abstract only; Retrieved on Jan. 3, 2014 from http://www.ncbi.nlm.nih.gov/pubmed/22456777).
Zhang, W. et al. (2007) Gender-specific differences in expression in human lymphoblastoid cell lines. Pharmacogenet Genomics. 17(6): 447-450.
Zhang, X. et al. (1999) Telomere shortening and apoptosis in telomerase-inhibited human tumor cells. Genes Dev. 13(18): 2388-2399.
Zhu, H. et al., Healthy Aging and Disease: Role for Telomere Biology?, Clin Sci (Lond), 120(10):427-40 (2011).
Zijlmans JM, et al. (1997) Telomeres in the mouse have large inter-chromosomal variations in the number of T2AG3 repeats. Proc Natl Acad Sci USA. 94(14): 7423-7428.
Examination Report No. 1 dated Aug. 4, 2015 by the Intellectual Property Office of Australia for Australian Patent Application No. 2009329987, which was filed on Jun. 27, 2011 (Applicant—University of Utah; Inventor—Cawthon et al.; (3 pages).
Notice of Abandonment dated Feb. 16, 2015 by the Canadian Intellectual Property Office for Canadian Patent Application No. 2748265, which was filed on Jun. 22, 2011 (Applicant—University of Utah; Inventor—Cawthon et al.; (1 page).

(56) References Cited

OTHER PUBLICATIONS

Vander Griend, D.J. et al., Dual-Label Centromere and Telomere FISH Identifies Human, Rat, and Mouse Cell Contribution to Multi species Recombinant Urogenital Sinus Xenografts, Prostate, 69(14): 1557-64 (2009).
Vera, E. et al., The Rate of Increase of Short Telomeres Predicts Longevity in Mammals, Cell Rep, 2(4): 732-7 (2012).
Verzola, D. et al., Accelerated senescence in the kidneys of patients with type 2 diabetic nephropathy, Am J Physiol, 295: F1563-73 (2008).
Vincent, M. et al., Helicase-Dependent Isothermal DNA Amplification, EMBO Rep, 5(8): 795-800 (2004).
von Ahsen, N. et al., Application of a Thermodynamic Nearest-Neighbor Model to Estimate Nucleic Acid Stability and Optimize Probe Design: Prediction of Melting Points of Multiple Mutations of Apolipoprotein B-3500 and Factor V with a Hybridization Probe Genotyping Assay on the LightCycler, Clin Chem, 45(12): 2094-101 (1999).
von Kiedrowski, G. et al., Parabolic Growth of a Self-Replicating Hexadeoxynucleotide Bearing a 3'-5'-Phosphoamidate Linkage, Angew Chem Int Ed Engl, 30(4): 423-6 (1991).
von Zglinicki, T., Role of oxidative stress in telomere length regulation and replicative senescence, Ann NY Acad Sci, 908: 99-110 (2000).
Wang, L. et al. (2007) Cdc42 GTPase-activating protein deficiency promotes genomic instability and premature aging-like phenotypes. Proc Natl Acad Sci USA. 104(4): 1248-1253.
Ware, J.E., SF-36® Health Survey Update, (found at http://www.sf-36.org/tools/SF36.shtml; retrieved on Dec. 21, 2014) (18 pages).
Wetmur, J.G., DNA Probes: Application of the Principles of Nucleic Acid Hybridization, Crit Rev Biochem Mol Biol, 26(3-4): 227-59 (1991).
White, R. et al. (1985) Construction of linkage maps with DNA markers for human chromosomes. Nature. 313(5998): 101-105.
Wiemann, S.U. et al., Hepatocyte telomere shortening and senescence are general markers of human liver cirrhosis, FASEB J, 16(9): 935-82 (2002).
Wikgren, M. et al., Short Telomeres in Depression and the General Population are Associated with a Hypocortisolemic State, Biol Psychiatry, 71: 294-300 (2011).
Willeit, P. et al., Cellular Aging Reflected by Leukocyte Telomere Length Predicts Advanced Atherosclerosis and Cardiovascular Disease Risk, Aterioscler Thromb Vasc Biol, 30: 1649-56 (2010).
Willeit, P., et al., "Telomere length and risk of incident cancer and cancer mortality," JAMA, 304(1): 69-75 (2010).
Wilson, C.L. et al. (2004) Amplification protocols introduce systematic but reproducible errors into gene expression studies. Biotechniques. 36(3): 498-506.
Certificate of Patent issued on Jul. 3, 2013 for European application No. 098041775, which was filed on Dec. 22, 2009 and granted as 2379747 on Jul. 3, 2013 (Applicant—University of Utah; Inventor—Cawthon et al.;) (39 pages).
Office Action dated Jun. 4, 2014 by the Japan Patent Office for Japanese Patent Application No. 2011-543646, which was filed on Jun. 22, 2011 and published on Jun. 14, 2012 (Applicant—University of Utah; Inventor—Cawthon et al.;) (4 pages).
Office Action dated May 7, 2015 by the Japan Patent Office for Japanese Patent Application No. 2011-543646, which was filed on Jun. 22, 2011 and published on Jun. 14, 2012 (Applicant—University of Utah; Inventor—Cawthon et al.;) (3 pages).
Notice of Allowance dated Oct. 21, 2015 by the Japan Patent Office for Japanese Patent Application No. 2011-543646, which was filed on Jun. 22, 2011 and published on Jun. 14, 2012 (Applicant—University of Utah; Inventor—Cawthon et al.;) (3 pages).
International Search Report dated Mar. 30, 2010 for PCT/US2009/069243, filed on Dec. 22, 2009 and published as WO 2010/075413 on Jul. 1, 2010 (Applicant—University of Utah; Inventor—Cawthon et al.;) (5 pages).
Written Opinion of International Search Report dated Jun. 22, 2011 for PCT/US2009/069243, filed on Dec. 22, 2009 and published as WO 2010/075413 on Jul. 1, 2010 (Applicant—University of Utah; Inventor—Cawthon et al.;) (5 pages).
International Preliminary Report on patentability dated Jun. 22, 2011 for PCT/US2009/069243, filed on Dec. 22, 2009 and published as WO 2010/075413 on Jul. 1, 2010 (Applicant—University of Utah; Inventor—Cawthon et al.;) (6 pages).
Preliminary Amendment filed on Jun. 22, 2011 for U.S. Appl. No. 13/141,429, which was filed Aug. 15, 2011 and published as US 2011/0294676 on Dec. 1, 2011 (Applicant—University of Utah; Inventor—Cawthon et al.;) (3 pages).
Restriction Requirement dated Aug. 20, 2014 for U.S. Appl. No. 13/141,429, which was filed Aug. 15, 2011 and published as US 2011/0294676 on Dec. 1, 2011 (Applicant—University of Utah; Inventor—Cawthon et al.;) (10 pages).
Response to Restriction Requirement filed on Oct. 20, 2014 for U.S. Appl. No. 13/141,429, which was filed Aug. 15, 2011 and published as US 2011/0294676 on Dec. 1, 2011 (Applicant—University of Utah; Inventor—Cawthon et al.;) (9 pages).
Notice of Amendment and Completion of Formalities dated Sep. 29, 2011 for Chinese application No. 200980157269.8, which claims priority to PCT/US2009/069243, filed on Dec. 22, 2009. (Applicant—University of Utah; Inventor—Cawthon et al.;) (3 pages).
Response to Notice of Amendment and Completion of Formalities dated Jan. 19, 2012 for Chinese application No. 200980157269.8, which claims priority to PCT/US2009/069243, filed on Dec. 22, 2009. (Applicant—University of Utah; Inventor—Cawthon et al.;) (2 pages).
Notice of Passing Preliminary Exam dated Feb. 10, 2012 for Chinese application No. 200980157269.8, which claims priority to PCT/US2009/069243, filed on Dec. 22, 2009. (Applicant—University of Utah; Inventor—Cawthon et al.;) (1 pages).
First Office Action dated May 6, 2013 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.;) (12 pages).
Second Office Action dated Dec. 26, 2013 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.;) (13 pages).
Decision on Rejection dated Jul. 8, 2014 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.;) (12 pages).
Communication Pursuant to Rules 161(1) and 162 EPC dated Aug. 2, 2011 for European application No. 09804177.5, which was filed on Dec. 22, 2009 and granted as 2379747 on Jul. 3, 2013 (Applicant—University of Utah; Inventor—Cawthon et al.;) (2 pages).
Amendment before examination filed on Feb. 13, 2012 for European application No. 09804177.5, which was filed on Dec. 22, 2009 and granted as 2379747 on Jul. 3, 2013 (Applicant—University of Utah; Inventor—Cawthon et al.;) (18 pages).
Decision to Grant dated Jun. 6, 2013 for European application No. 09804177.5, which was filed on Dec. 22, 2009 and granted as 2379747 on Jul. 3, 2013 (Applicant—University of Utah; Inventor—Cawthon et al.;) (2 pages).
Response to Office Action filed on Jan. 20, 2011 for Canadian application No. 2474468, which claims priority to PCT/US2003/002844, filed on Jan. 31, 2003. (Applicant—University of Utah; Inventor—Cawthon et al.;) (3 pages).
Office Action dated Jul. 13, 2011 for Canadian application No. 2474468, which claims priority to PCT/US2003/002844, filed on Jan. 31, 2003. (Applicant—University of Utah; Inventor—Cawthon et al.;) (2 pages).
Response to Office Action filed on Jan. 13, 2012 for Canadian application No. 2474468, which claims priority to PCT/US2003/002844, filed on Jan. 31, 2003. (Applicant—University of Utah; Inventor—Cawthon et al.;) (15 pages).

(56) References Cited

OTHER PUBLICATIONS

Office Action dated May 29, 2012 for Canadian application No. 2474468, which claims priority to PCT/US2003/002844, filed on Jan. 31, 2003. (Applicant—University of Utah; Inventor—Cawthon et al.;) (2 pages).
Response to Office Action filed on Nov. 29, 2012 for Canadian application No. 2474468, which claims priority to PCT/US2003/002844, filed on Jan. 31, 2003. (Applicant—University of Utah; Inventor—Cawthon et al.;) (9 pages).
Notice of Allowance dated Jul. 23, 2013 for Canadian application No. 2474468, which claims priority to PCT/US2003/002844, filed on Jan. 31, 2003. (Applicant—University of Utah; Inventor—Cawthon et al.;) (1 page).
Certificate of Patent issued on Mar. 25, 2014 for Canadian application No. 2474468, which claims priority to PCT/US2003/002844, filed on Jan. 31, 2003. (Applicant—University of Utah; Inventor—Cawthon et al.;) (1 page).
Office Action dated Mar. 17, 2006 for Chinese application No. 03804867.1, which claims priority to PCT/US2003/002844, filed on Jan. 31, 2003. (Applicant—University of Utah; Inventor—Cawthon et al.;) (12 pages).
Response to Office Action filed on Sep. 19, 2006 for Chinese application No. 03804867.1, which claims priority to PCT/US2003/002844, filed on Jan. 31, 2003. (Applicant—University of Utah; Inventor—Cawthon et al.;) (5 pages).
Non-Final Office Action dated Jan. 23, 2015 for U.S. Appl. No. 13/141,429, filed Aug. 15, 2011 and published as US 2011/0294676 on Dec. 1, 2011 (Applicant—University of Utah; Inventor—Cawthon et al.;) (7 pages).
Response to Non-Final Office Action filed on Apr. 23, 2015 for U.S. Appl. No 13/141,429, filed Aug. 15, 2011 and published as US 2011/0294676 on Dec. 1, 2011 (Applicant—University of Utah; Inventor—Cawthon et al.;) (15 pages).
Non-Final Office Action dated Jun. 18, 2015 for U.S. Appl. No. 13/141,429, filed Aug. 15, 2011 and published as US 2011/0294676 on Dec. 1, 2011 (Applicant—University of Utah; Inventor—Cawthon et al.;) (7 pages).
Response to Non-Final Office Action filed on Oct. 15, 2015 for U.S. Appl. No. 13/141,429, filed Aug. 15, 2011 and published as US 2011/0294676 on Dec. 1, 2011 (Applicant—University of Utah; Inventor—Cawthon et al.;) (9 pages).
Request for examination filed on May 3, 2006 for Australian application No. 2003208902, which claims priority to PCT/US2003/002844, filed on Jan. 31, 2003. (Applicant—University of Utah; Inventor—Cawthon et al.;) (1 page).
Office Action dated Mar. 29, 2007 for Australian application No. 2003208902, which claims priority to PCT/US2003/002844, filed on Jan. 31, 2003. (Applicant—University of Utah; Inventor—Cawthon et al.;) (2 pages).
Response to Office Action filed on Jul. 23, 2008 for Australian application No. 2003208902, which claims priority to PCT/US2003/002844, filed on Jan. 31, 2003. (Applicant—University of Utah; Inventor—Cawthon et al.;) (16 pages).
Notice of Acceptance dated Jul. 25, 2008 for Australian application No. 2003208902, which claims priority to PCT/US2003/002844, filed on Jan. 31, 2003. (Applicant—University of Utah; Inventor—Cawthon et al.;) (7 pages).
Voluntary Amendment filed on Sep. 20, 2004 for Canadian application No. 2474468, which claims priority to PCT/US2003/002844, filed on Jan. 31, 2003. (Applicant—University of Utah; Inventor—Cawthon et al.;) (3 pages).
Office Action dated Jul. 22, 2010 for Canadian application No. 2474468, which claims priority to PCT/US2003/002844, filed on Jan. 31, 2003. (Applicant—University of Utah; Inventor—Cawthon et al.;) (4 pages).
Certificate of Grant issued Nov. 23, 2011 for European application No. 03707624.7, which claims priority to PCT/US2003/002844, filed on Jan. 31, 2003. (Applicant—University of Utah; Inventor—Cawthon et al.;) (1 page).
Request for Registration filed on Feb. 11, 2012 for Hong Kong application No 051035547, which claims priority to PCT/US2003/002844, filed on Jan. 31, 2003. (Applicant—University of Utah; Inventor—Cawthon et al.;) (1 page).
Certificate of Grant issued Jun. 15, 2012 for Hong Kong application No. 05103554.7, which claims priority to PCT/US2003/002844, filed on Jan. 31, 2003. (Applicant—University of Utah; Inventor—Cawthon et al.;) (4 pages).
Office Action dated Oct. 7, 2008 for Japanese application No. 2003-564211, which claims priority to PCT/US2003/002844, filed on Jan. 31, 2003. (Applicant—University of Utah; Inventor—Cawthon et al.;) (2 pages).
Response to Office Action filed on Apr. 7, 2009 for Japanese application No. 2003-564211, which claims priority to PCT/US2003/002844, filed on Jan. 31, 2003. (Applicant—University of Utah; Inventor—Cawthon et al.;) (4 pages).
Office Action dated May 7, 2009 for Japanese application No. 2003-564211, which claims priority to PCT/US2003/002844, filed on Jan. 31, 2003. (Applicant—University of Utah; Inventor—Cawthon et al.;) (1 page).
Response to Office Action filed on Sep. 7, 2009 for Japanese application No. 2003-564211, which claims priority to PCT/US2003/002844, filed on Jan. 31, 2003. (Applicant—University of Utah; Inventor—Cawthon et al.;) (6 pages).
Office Action dated Nov. 4, 2009 for Japanese application No. 2003-564211, which claims priority to PCT/US2003/002844, filed on Jan. 31, 2003. (Applicant—University of Utah; Inventor—Cawthon et al.;) (1 page).
Response to Office Action filed on Apr. 27, 2010 for Japanese application No. 2003-564211, which claims priority to PCT/US2003/002844, filed on Jan. 31, 2003. (Applicant—University of Utah; Inventor—Cawthon et al.;) (1 page).
Notice of Acceptance dated Apr. 1, 2009 for Chinese application No. 03804867.1, which claims priority to PCT/US2003/002844, filed on Jan. 31, 2003. (Applicant—University of Utah; Inventor—Cawthon et al.;) (2 pages).
Request for examination filed on Aug. 20, 2004 for European application No. 03707624.7, which claims priority to PCT/US2003/002844, filed on Jan. 31, 2003. (Applicant—University of Utah; Inventor—Cawthon et al.;) (7 pages).
Office Action dated Oct. 26, 2006 for European application No. 03707624.7, which claims priority to PCT/US2003/002844, filed on Jan. 31, 2003. (Applicant—University of Utah; Inventor—Cawthon et al.;) (7 pages).
Response to Office Action filed on Aug. 21, 2007 for European application No. 03707624.7, which claims priority to PCT/US2003/002844, filed on Jan. 31, 2003. (Applicant—University of Utah; Inventor—Cawthon et al.;) (9 pages).
Office Action dated Dec. 13, 2007 for European application No. 03707624.7, which claims priority to PCT/US2003/002844, filed on Jan. 31, 2003. (Applicant—University of Utah; Inventor—Cawthon et al.;) (6 pages).
Response to Office Action filed on Sep. 17, 2008 for European application No. 03707624.7, which claims priority to PCT/US2003/002844, filed on Jan. 31, 2003. (Applicant—University of Utah; Inventor—Cawthon et al.;) (7 pages).
Office Action dated Oct. 13, 2010 for European application No. 03707624.7, which claims priority to PCT/US2003/002844, filed on Jan. 31, 2003. (Applicant—University of Utah; Inventor—Cawthon et al.;) (6 pages).
Response to Office Action filed on Jan. 18, 2011 for European application No. 03707624.7, which claims priority to PCT/US2003/002844, filed on Jan. 31, 2003. (Applicant—University of Utah; Inventor—Cawthon et al.;) (20 pages).
Intention to Grant dated Jun. 6, 2011 for European application No. 03707624.7, which claims priority to PCT/US2003/002844, filed on Jan. 31, 2003. (Applicant—University of Utah; Inventor—Cawthon et al.;) (5 pages).
Response to Non-Final Office Action filed on Jan. 22, 2008 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (10 pages).

(56) References Cited

OTHER PUBLICATIONS

Final Office Action dated Mar. 27, 2008 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.; (18 pages).
Response to Final Office Action filed on Jun. 27, 2008 for U.S. Appl. No. 10/355,626, filed Jan. 31, 2003 and issued as U.S. Pat. No. 7,695,904 on Apr. 13 2010 (Applicant—University of Utah; Inventor—Cawthon et al.,) (10 pages).
Notice of Appeal filed on Sep. 26, 2008 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (1 page).
Advisory Action dated Oct. 7, 2008 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (4 pages).
Office Action dated Jan. 22, 2009 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (8 pages).
Response to Office Action filed on Jul. 22, 2009 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (11 pages).
Notice of Allowance dated Nov. 17, 2009 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (6 pages).
Issue Notification dated Mar. 24, 2010 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (1 page).
Notice of Grant and Translated Claims issued May 21, 2010 for Japanese application No. 2003-564211, which claims priority to PCT/US2003/002844, filed on Jan. 31, 2003. (Applicant—University of Utah; Inventor—Cawthon et al.;) (21 pages).
International Search Report dated Nov. 25, 2003 for PCT/US2003/002844, filed on Jan. 31, 2003. (Applicant—University of Utah; Inventor—Cawthon et al.;) (2 pages).
International Preliminary Examination Report dated Nov. 16, 2004 for PCT/US2003/002844, filed on Jan. 31, 2003 and published as WO 2003/064615 on Aug. 7, 2003 (Applicant—University of Utah; Inventor—Cawthon et al.;) (3 pages).
Preliminary Amendment filed on Apr. 29, 2003 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (9 pages).
Preliminary Amendment filed on Feb. 17, 2005 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (9 pages).
Restriction Requirement dated May 2, 2006 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (6 pages).
Response to Restriction Requirement filed on Jun. 5, 2006 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (7 pages).
Restriction Requirement dated Aug. 9, 2006 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (8 pages).
Response to Restriction Requirement dated Mar. 2, 2007 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (8 pages).
Non-Final Office Action dated Aug. 6, 2007 for U.S. Appl. No. 10/355,626, filed Jan. 31, 2003 and issued as U.S. Pat. No. 7,695,904 on Apr. 13, 2010 (Applicant—University of Utah; Inventor—Cawthon et al.;) (10 pages).
Office Action dated Apr. 16, 2012 for Canadian application No. 2513747, which claims priority to PCT/US2004/002215, filed on Jan. 26, 2004. (Applicant—University of Utah; Inventor—Cawthon et al.;) (3 pages).
Response to Office Action filed on Oct. 16, 2012 for Canadian application No. 2513747, which claims priority to PCT/US2004/002215, filed on Jan. 26, 2004. (Applicant—University of Utah; Inventor—Cawthon et al.;) (10 pages).
Office Action dated Oct. 22, 2015 for Canadian application No. 2513747, which claims priority to PCT/US2004/002215, filed on Jan. 26, 2004. (Applicant—University of Utah; Inventor—Cawthon et al.;) (5 pages).
Office Action dated Jan. 22, 2010 for European application No. 04705326.9, which claims priority to PCT/US2004/002215, filed on Jan. 26, 2004. (Applicant—University of Utah; Inventor—Cawthon et al.;) (6 pages).
Response to Office Action filed on Jun. 21, 2010 for European application No. 04705326.9, which claims priority to PCT/US2004/002215, filed on Jan. 26, 2004. (Applicant—University of Utah; Inventor—Cawthon et al.;) (6 pages).
Office Action dated Dec. 27, 2011 for European application No. 04705326.9, which claims priority to PCT/US2004/002215, filed on Jan. 26, 2004. (Applicant—University of Utah; Inventor—Cawthon et al.; (7 pages).
Office Action dated Feb. 21, 2012 for European application No. 04705326.9, which claims priority to PCT/US2004/002215, filed on Jan. 26, 2004. (Applicant—University of Utah; Inventor—Cawthon et al.; (2 pages).
Response to Office Action filed Apr. 30, 2012 for European application No. 04705326.9, which claims priority to PCT/US2004/002215, filed on Jan. 26, 2004. (Applicant—University of Utah; Inventor—Cawthon et al.;) (1 page).
Supplementary Search Report dated Jun. 19, 2012 for European application No. 04705326.9, which claims priority to PCT/US2004/002215, filed on Jan. 26, 2004. (Applicant—University of Utah; Inventor—Cawthon et al.;) (5 pages).
Response to Office Action filed on Jul. 2, 2012 for European application No. 04705326.9, which claims priority to PCT/US2004/002215, filed on Jan. 26, 2004. (Applicant—University of Utah; Inventor—Cawthon et al.;) (2 pages).
Restriction Requirement dated Jul. 8, 2010 for U.S. Appl. No. 12/700,475, filed Feb. 4, 2010 and issued as U.S. Pat. No. 8,048,631 on Nov. 1, 2011 (Applicant—University of Utah; Inventor—Cawthon et al.;) (6 pages).
Response to Restriction Requirement filed on Aug. 9, 2010 for U.S. Appl. No 12/700,475, filed Feb. 4, 2010 and issued as U.S. Pat. No. 8,048,631 on Nov. 1, 2011 (Applicant—University of Utah; Inventor—Cawthon et al.,) 10 pages.
Office Action dated Oct. 28, 2010 for U.S. Appl. No. 12/700,475, filed Feb. 4, 2010 and issued as U.S. Pat. No. 8,048,631 on Nov. 1, 2011 (Applicant—University of Utah; Inventor—Cawthon et al.;) (8 pages).
Response to Office Action filed on Mar. 28, 2011 for U.S Appl. No. 12/700,475, filed Feb. 4, 2010 and issued as U.S. Pat. No. 8,048,631 on Nov. 1, 2011 (Applicant—University of Utah; Inventor—Cawthon et al.;) (14 pages).
Supplemental Application Data Sheet filed on Jun. 15, 2011 for U.S. Appl. No. 12/700,475, filed Feb. 4, 2010 and issued as U.S. Pat. No. 8,048,631 on Nov. 1, 2011 (Applicant—University of Utah; Inventor—Cawthon et al.;) (5 pages).
Notice of Allowance dated Jun. 27, 2011 for U.S. Appl. No. 12/700,475, filed Feb. 4, 2010 and issued as U.S. Pat. No. 8,048,631 on Nov. 1, 2011 (Applicant—University of Utah; Inventor—Cawthon et al.;) (10 pages).
Issue Notification dated Oct. 12, 2011 for U.S. Appl. No. 12/700,475, filed Feb. 4, 2010 and issued as U.S. Pat. No. 8,048,631 on Nov. 1, 2011 (Applicant—University of Utah; Inventor—Cawthon et al.;) (1 page).

(56) References Cited

OTHER PUBLICATIONS

Office Action dated Mar. 8, 2011 for Canadian application No. 2513747, which claims priority to PCT/US2004/002215, filed on Jan. 26, 2004. (Applicant—University of Utah; Inventor—Cawthon et al.;) (3 pages).
Response to Office Action filed on Sep. 8, 2011 for Canadian application No. 2513747, which claims priority to PCT/US2004/002215, filed on Jan. 26, 2004. (Applicant—University of Utah; Inventor—Cawthon et al.;) (23 pages).
Response to Communication pursuant to Rules 70(2) and 70a(2) EPC and reference to Rule 39(1) EPC filed on Apr. 22, 2013 for European application No. 12152681.8, which was filed on Jan. 26, 2012 and published as 2474822 on Jul. 11, 2012 (Applicant—University of Utah; Inventor—Cawthon et al.;) (4 pages).
Office Action dated Nov. 4, 2009 for Japanese application No. 2006-503063, which claims priority to PCT/US2004/002215, filed on Jan. 26, 2004. (Applicant—University of Utah; Inventor—Cawthon et al.;) (2 pages).
Response to Office Action filed on Mar. 25, 2010 for Japanese application No. 2006-503063, which claims priority to PCT/US2004/002215, filed on Jan. 26, 2004. (Applicant—University of Utah; Inventor—Cawthon et al.;) (5 pages).
Office Action dated Nov. 16, 2010 for Japanese application No. 2006-503063, which claims priority to PCT/US2004/002215, filed on Jan. 26, 2004. (Applicant—University of Utah; Inventor—Cawthon et al.;) (2 pages).
Notice of appeal filed Mar. 16, 2011 for Japanese application No. 2006-503063, which claims priority to PCT/US2004/002215, filed on Jan. 26, 2004. (Applicant—University of Utah; Inventor—Cawthon et al.;) (3 pages).
Formality office action dated Apr. 12, 2011 for Japanese application No. 2006-503063, which claims priority to PCT/US2004/002215, filed on Jan. 26, 2004. (Applicant—University of Utah; Inventor—Cawthon et al.;) (2 pages).
Appeal brief filed May 24, 2011 for Japanese application No. 2006-503063, which claims priority to PCT/US2004/002215, filed on Jan. 26, 2004. (Applicant—University of Utah; Inventor—Cawthon et al.;) (8 pages).
Office Action dated Jan. 21, 2014 for Japanese application No. 2006-503063, which claims priority to PCT/US2004/002215, filed on Jan. 26, 2004. (Applicant—University of Utah; Inventor—Cawthon et al.;) (4 pages).
Response to Office Action filed on May 20, 2014 for Japanese application No. 2006-503063, which claims priority to PCT/US2004/002215, filed on Jan. 26, 2004. (Applicant—University of Utah; Inventor—Cawthon et al.;) (6 pages).
Intention to Grant dated Sep. 4, 2012 for European application No. 04705326.9, which claims priority to PCT/US2004/002215, filed on Jan. 26, 2004. (Applicant—University of Utah; Inventor—Cawthon et al.;) (44 pages).
Decision to Grant dated Jan. 31, 2013 for European application No. 04705326.9, which claims priority to PCT/US2004/002215, filed on Jan. 26, 2004. (Applicant—University of Utah; Inventor—Cawthon et al.;) (2 pages).
Certificate of Grant issued on Feb. 27, 2013 for European application No. 04705326.9, which claims priority to PCT/US2004/002215, filed on Jan. 26, 2004. (Applicant—University of Utah; Inventor—Cawthon et al.;) (1 page).
Office Action dated Feb. 16, 2012 for European application No. 12152681.8, which was filed on Jan. 26, 2012 and published as 2474822 on Jul. 11, 2012 (Applicant—University of Utah; Inventor—Cawthon et al.;) (1 page).
Response to Office Action filed Apr. 26, 2012 for European application No. 12152681.8, which was filed on Jan. 26, 2012 and published as 2474822 on Jul. 11, 2012 (Applicant—University of Utah; Inventor—Cawthon et al.;) (1 page).
Office Action dated Apr. 27, 2012 for European application No. 12152681.8, which was filed on Jan. 26, 2012 and published as 2474822 on Jul. 11, 2012 (Applicant—University of Utah; Inventor—Cawthon et al.;) (2 pages).

Response to Office Action filed May 14, 2012 for European application No. 12152681.8, which was filed on Jan. 26, 2012 and published as 2474822 on Jul. 11, 2012 (Applicant—University of Utah; Inventor—Cawthon et al.;) (1 page).
Supplementary Search Report dated Jun. 8, 2012 for European application No. 12152681.8, which was filed on Jan. 26, 2012 and published as 2474822 on Jul. 11, 2012 (Applicant—University of Utah; Inventor—Cawthon et al.;) (11 pages).
Communication pursuant to Rules 70(2) and 70a(2) EPC and reference to Rule 39(1) EPC dated Jul. 16, 2012 for European application No. 12152681.8, which was filed on Jan. 26, 2012 and published as 2474822 on Jul. 11, 2012 (Applicant—University of Utah; Inventor—Cawthon et al.;) (2 pages).
Response to Non-Final Office Action filed on May 8, 2015 for U.S. Appl. No, 10/543,111, filed Mar. 10, 2006 and issued as U.S. Pat. No. 9,169,516 on Oct. 27, 2015 (Applicant—University of Utah; Inventor—Cawthon et al.;) (12 pages).
Notice of Allowance dated Jun. 15, 2015 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (7 pages).
Issue Notification dated Oct. 27, 2015 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (1 page).
Preliminary Amendment filed on Sep. 18, 2015 for U.S. Appl. No. 14/858,177, filed Sep. 18, 2015 (Applicant—University of Utah; Inventor—Cawthon et al.;) (3 pages).
Restriction Requirement dated Jan. 24, 2013 for U.S. Appl. No. 13/028,910, filed Feb. 16, 2011 and published as US 2011/0207128 on Aug. 25, 2011 (Applicant—University of Utah; Inventor—Cawthon et al.;) (8 pages).
Notice of Abandonment dated Aug. 7, 2013 for U.S. Appl. No. 13/028,910, filed Feb. 16, 2011 and published as US 2011/0207128 on Aug. 25, 2011 (Applicant—University of Utah; Inventor—Cawthon et al.;) (2 pages).
International Search Report dated Dec. 30, 2014 by the International Searching Authority for International Patent Application No. PCT/US2014/039110, which was filed on May 22, 2014 and published as WO 2014/190138 on Nov. 27, 2014 (Inventor—Harley; Applicant—Telome Health, Inc.;) (6 pages).
Supplementary European Search Report dated Jul. 10, 2015 by the European Patent Office for European Patent Application No. 12863843.4, which was filed on Dec. 28, 2012 and published as EP 2798091 on Nov. 6, 2014 (Inventor—Harley; Applicant—Telome Health, Inc.;) (6 pages).
Office Action dated Feb. 2, 2015 by the State Intellectual Property Office of the People's republic of China for Chinese Patent Application No. 2012800689920, which was filed on Dec. 28, 2012 and published as CN104105798 on Oct. 15, 2014 (Inventor—Harley; Applicant—Telome Health, Inc.;) (4 pages).
International Search Report and Written Opinion dated Mar. 11, 2013 by the International Searching Authority for International Patent Application No. PCT/US2012/072131, which was filed on Dec. 28, 2012 and published as WO 2013/102116 on Jul. 4, 2013 (Inventor—Harley; Applicant—Telome Health, Inc.;) (12 pages).
International Preliminary Report on Patentability dated Jul. 1, 2014 by the International Searching Authority for International Patent Application No. PCT/US2012/072131, which was filed on Dec. 28, 2012 and published as WO 2013/102116 on Jul. 4, 2013 (Inventor—Harley; Applicant—Telome Health, Inc.;) (10 pages).
Preliminary Amendment filed on Jun. 30, 2014 for U.S. Appl. No. 14/370,005, filed Dec. 28, 2012 and published as US 2014/0370505 on Dec. 18, 2014 (Telomere Diagnostics, Inc.; Inventor—Harley;) (3 pages).
Preliminary Amendment filed on Nov. 5, 2014 for U.S. Appl. No. 14/370,005, filed Dec. 28, 2012 and published as US 2014/0370505 on Dec. 18, 2014 (Telomere Diagnostics, Inc.; Inventor—Harley;) (6 pages).
Restriction Requirement dated Sep. 4, 2015 for U.S. Appl. No. 14/370,005, filed Dec. 28, 2012 and published as US 2014/0370505 on Dec. 18, 2014 (Telomere Diagnostics, Inc.; Inventor—Harley;) (9 pages).

(56) References Cited

OTHER PUBLICATIONS

Response to Restriction Requirement filed on Oct. 20, 2015 for U.S. Appl. No. 14/370,005, filed Dec. 28, 2012 and published as US 2014/0370505 on Dec. 18, 2014 (Telomere Diagnostics, Inc.; Inventor—Harley;) (9 pages).
Non-Final Office Action dated Nov. 19, 2015 for for U.S. Appl. No. 14/370,005, filed Dec. 28, 2012 and published as US 2014/0370505 on Dec. 18, 2014 (Telomere Diagnostics, Inc.; Inventor—Harley;) (11 pages).
International Search Report and Written Opinion dated Oct. 28, 2015 by the International Searching Authority for International Patent Application No. PCT/US2015/036991, which was filed on Jun. 22, 2015 (Inventor—Harley et al.; Applicant—Telome Health, Inc.;) (12 pages).
Office Action dated Sep. 2, 2014 for Japanese application No 2006-503063, which claims priority to PCT/US2004/002215, filed on Jan. 26, 2004. (Applicant—University of Utah; Inventor—Cawthon et al;) (4 pages).
Response to Office Action filed on Nov. 28, 2014 for Japanese application No. 2006-503063, which claims priority to PCT/US2004/002215, filed on Jan. 26, 2004, (Applicant—University of Utah; Inventor—Cawthon et al.;) (2 pages).
Certificate of Patent issued on Jan. 30, 2015 for Japanese application No. 2006-503063, which claims priority to PCT/US2004/002215, filed on Jan. 26, 2004. (Applicant—University of Utah; Inventor—Cawthon et al.;) (1 page).
International search report dated Nov. 18, 2004 for PCT/US2004/002215, which was filed on Jan. 26, 2004 and published as WO 2004/068110 on Aug. 12, 2004 (Applicant—University of Utah; Inventor—Cawthon et al.;) (4 pages).
Written opinion of international search report dated Jul. 24, 2005 for PCT/US2004/002215, which was filed on Jan. 26, 2004 and published as WO 2004/068110 on Aug. 12, 2004 (Applicant—University of Utah; Inventor—Cawthon et al.;) (5 pages).
International preliminary report on patentability dated on Jul. 29, 2005 for PCT/US2004/002215, which was filed on Jan. 26, 2004 and published as WO 2004/068110 on Aug. 12, 2004 (Applicant—University of Utah; Inventor—Cawthon et al.;) (6 pages).
Preliminary Amendment filed on Mar. 10, 2006 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (8 pages).
Non-Final Office Action dated Aug. 23, 2007 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (14 pages).
Response to Non-Final Office Action filed on Feb. 25, 2008 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (8 pages).
Non-Final Office Action dated May 12, 2008 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (10 pages).
Response to Non-Final Office Action filed on Nov. 12, 2008 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (6 pages).
Final Office Action dated Jan. 27, 2009 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (16 pages).
Response After Final Office Action filed on Nov. 25, 2009 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (13 pages).
Non-Final Office Action dated May 2, 2013 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (7 pages).
Response to Non-Final Office Action filed on Nov. 1, 2013 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (6 pages).
Final Office Action dated Jan. 10, 2014 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (12 pages).
Response to Final Office Action and request for Continued Examination filed on Jul. 10, 2014 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (11 pages).
Non-Final Office Action dated Jan. 8, 2015 for U.S. Appl. No. 10/543,111, filed Mar. 10, 2006 and issued as U.S. Pat. No. 9,169,516 on Oct. 27, 2015 (Applicant—University of Utah; Inventor—Cawthon et al.;) (10 pages).
Lin, K.W. et al., The Telomere Length Dynamic and Methods of Its Assessment. J Cell Mol Med. 2005; 9(4):977-89.
Sfelr, A.J. et al., Telomere—End Processing: the Terminal Nucleotides of Human Chromosomes. Mol Cell. 2005; 18(1):131-8.
Office Action dated Nov. 18, 2016 by the Canadian Intellectual Property Office for Canadian Patent Application No. 2,748,265, which was filed on Aug. 22, 2011 (Applicant—University of Utah; Inventor—Cawthon et al.;) (3 pages).
Third Office Action dated Aug. 30, 2016 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.;) (4 pages).
Notice of Grant and Notice of Registration dated Apr. 6, 2017 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.;) (3 pages).
Office Action dated Jun. 28, 2016 by the Japan Patent Office for Japanese Patent Application No. 2015-175632, which was filed on Dec. 22, 2009 and published on Dec. 10, 2015 (Applicant—University of Utah; Inventor—Cawthon et al.;) (2 pages).
Penultimate Rejection dated Apr. 14, 2017 by the Japan Patent Office for Japanese Patent Application No. 2011-543646, which was filed on Jun. 22, 2011 and Issued as 5840950 on Nov. 20, 2015 (Applicant—University of Utah; Inventor—Cawthon et al.;) (2 pages).
Notice of Allowance dated Dec. 11, 2015 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (16 pages).
Non-Final Office Action dated Apr. 22, 2016 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (12 pages).
Response to Non-Final Office Action filed on Oct. 12, 2016 with the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (10 pages).
Final Office Action dated Jan. 25, 2017 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (9 pages).
Response After Final Office Action filed on Mar. 10, 2017 with the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (14 pages).
Notice of Allowance dated Mar. 30, 2017 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (15 pages).
Notice of Allowance dated Apr. 25, 2017 by the U.S. Patent and Trademark Office for U.S. Appl. No. 13/141,429, filed Aug. 15,

(56) References Cited

OTHER PUBLICATIONS 2011 and published as US 2011/0294676 on Dec. 1, 2011 (Applicant—University of Utah; Inventor—Cawthon et al.;) (6 pages).
Notice of Allowance dated May 26, 2017 by the U.S. Patent and Trademark Office for U.S. Patent Application No. 13/141,429, filed Aug. 15, 2011 and published as US 2011/0294676 on Dec. 1, 2011 (Applicant—University of Utah; Inventor—Cawthon et al.;) (6 pages).
Issue Notification dated Jun. 7, 2017 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.;) (1 page).
Notice of Allowance dated Dec. 1, 2016 for Canadian Patent application No. 2,513,747, which claims priority to PCT/US2004/002215, filed on Jan. 26, 2004 (Applicant—University of Utah; Inventor—Cawthon et al.;) (1 page).
Certificate of Patent issued on Mar. 7, 2017 for Canadian Patent application No. 2,513,747, which claims priority to PCT/US2004/002215, filed on Jan. 26, 2004 (Applicant—University of Utah; Inventor—Cawthon et al.;) (1 page).
Communication Pursuant to 94(3) EPC dated Nov. 17, 2016 for European Patent application No. 12152681.8, which was filed on Jan. 26, 2012 and published as 2474822 on Jul. 11, 2012 (Applicant—University of Utah; Inventor—Cawthon et al.;) (5 pages).
Supplementary European Search Report dated Dec. 2, 2016 by the European Patent Office for European Patent Application No. 14800611.7, which was flied on May 22, 2014 and published as 2999800 on Mar. 30, 2016 (Inventor—Harvey et al.; Applicant—Telomere Diagnostics, Inc.;) (10 pages).
Preliminary Amendment filed on Nov. 19, 2015 with the U.S. Patent and Trademark Office for U.S. Appl. No. 14/892,395, filed Nov. 19, 2015 and published as US 2018/0090830 on Mar. 31, 2016 (Inventor—Harley et al.; Applicant—Telomere Diagnostics, Inc.;) (10 pages).
Fourth Office Action dated Sep. 27, 2016 by the State Intellectual Property Office of the People's Republic of China for Chinese Patent Application No. 201280068992.0, which was filed on Dec. 28, 2012 and published as 104105798 on Oct. 15, 2014 (Inventor—Harley; Applicant—Telome Health, Inc.;) (Original—4 pages/ Translation—6 pages).
Response to Non-Final Office Action filed on May 18, 2016 with the U.S. Patent and Trademark Office for U.S. Appl. No. 14/370,005, filed Dec. 28, 2012 and published as US 2014/0370505 on Dec. 18, 2014 (Telomere Diagnostics, Inc.; Inventor—Harley;) (15 pages).
Notice of Abandonment dated Jan. 26, 2017 by the U.S. Patent and Trademark Office for U.S. Appl. No. 14/370,005, filed Dec. 28, 2012 and published as US 2014/0370505 on Dec. 18, 2014 (Telomere Diagnostics, Inc.; Inventor—Harley;) (2 pages).
Preliminary Amendment filed on Oct. 6, 2016 with the U.S. Patent and Trademark Office for U.S. Appl. No. 15/287,099, filed Oct. 6, 2016 and published as US 2017/0023451 on Jan. 26, 2017 (Inventor—Harley et al.; Applicant—Telomere Diagnostics, Inc.;) (6 pages).
Notice of Reasons for Rejection dated Oct. 12, 2017 by the Japanese Patent Office for Patent Application No. 2015-175362, which was filed on Sep. 7, 2015 and published as JP 2015-221053 dated Dec. 10, 2015 (Inventor—Cawthon et al.; Applicant—University of Utah Research Foundation; (Original-3 pages// Translation—3 pages).
Non-Final Office Action dated Nov. 2, 2017 by the U.S. Patent and Trademark Office for U.S. Appl. No. 14/858,177, which was filed on Sep. 18, 2015 and published as US 2016/0194705 dated Jul. 7, 2016 (Inventor—Richard Cawthon; Applicant—University of Utah research Foundation; (9 pages).

\* cited by examiner

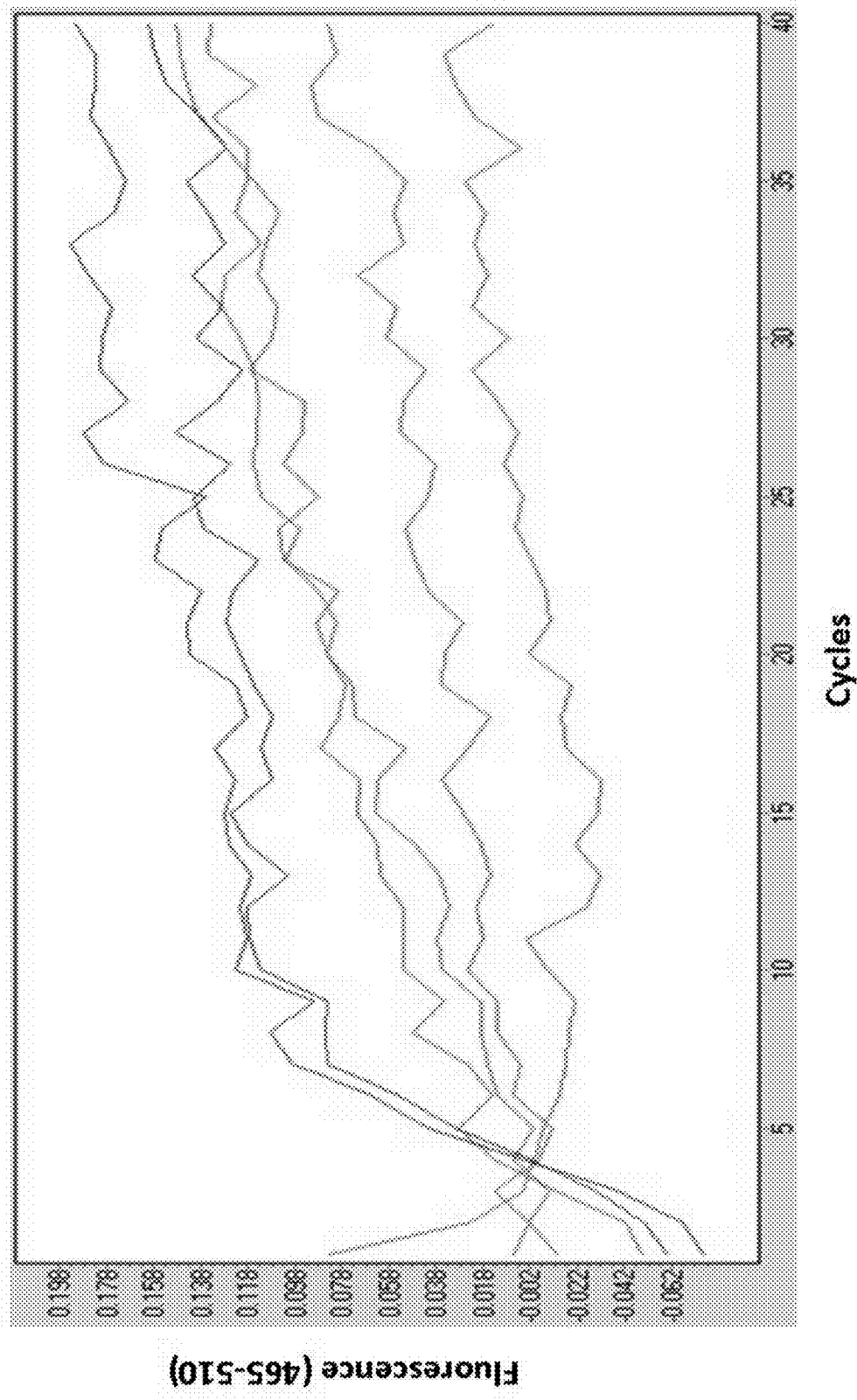

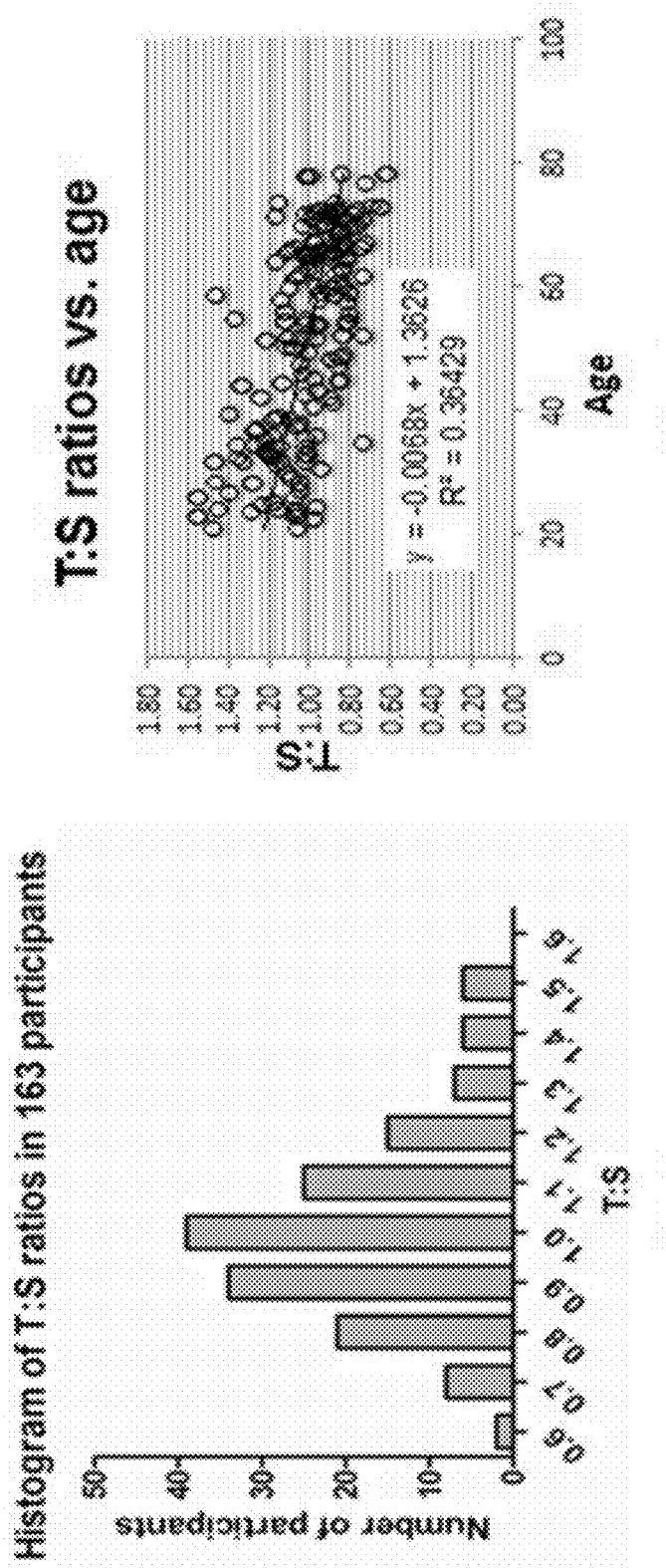

SEQUENCE LISTING

<160> NUMBER OF SEQ ID NOS: 30

<210> SEQ ID NO 1
<211> LENGTH: 45
<212> TYPE: DNA
<213> ORGANISM: Artificial Sequence
<220> FEATURE:
<223> OTHER INFORMATION: Synthetic

<400> SEQUENCE: 1
acacctcctc catggtttgg gtttgggttt gggtttgggt tagtg        45

<210> SEQ ID NO 2
<211> LENGTH: 43
<212> TYPE: DNA
<213> ORGANISM: Artificial Sequence
<220> FEATURE:
<223> OTHER INFORMATION: Synthetic

<400> SEQUENCE: 2
tgttagcgac gcgatatccc tatccctatc cctatcccta aca          43

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
ccagcagaga atggaaagtc aa                                 22

<210> SEQ ID NO 4
<211> LENGTH: 28
<212> TYPE: DNA

```
<213> ORGANISM: Artificial Sequence
<220> FEATURE:
<223> OTHER INFORMATION: Synthetic

<400> SEQUENCE: 4
tctctctcca ttcttcagta agtcaact                                         28

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
atgtgtctgg gtttcatcca tccgaca                                          27

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gttctctggg aactcacctc c                                                21

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
atgtcccttg ggaaggtctg                                                  20

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
cctaacaggg ctctccctga g                                                21

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tggccctagt ctcagacctt                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
cggagggaag ctcatcagtg                                                  20
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
ctgagtgcgt cctgtcac                                                   18

<210> SEQ ID NO 12
<211> LENGTH: 140
<212> TYPE: DNA
<213> ORGANISM: Artificial Sequence
<220> FEATURE:
<223> OTHER INFORMATION: Synthetic

<400> SEQUENCE: 12
cctaacctaa ccctaaccct aaccctaacc ctaaccctaa ccctaaccct aaccctaacc     60
ctaaccctaa ccctaaccct aaccctaacc ctaaccctaa ccctaaccct aaccctaacc    120
ctaaccctaa ccctaaccct                                                140

<210> SEQ ID NO 13
<211> LENGTH: 12
<212> TYPE: DNA
<213> ORGANISM: Artificial Sequence
<220> FEATURE:
<223> OTHER INFORMATION: Synthetic

<400> SEQUENCE: 13
ttagggttag gg                                                         12

<210> SEQ ID NO 14
<211> LENGTH: 45
<212> TYPE: DNA
<213> ORGANISM: Artificial Sequence
<220> FEATURE:
<223> OTHER INFORMATION: Synthetic

<400> SEQUENCE: 14
tgctcggccg atctggcatc cctaacccta accctaaccc taacc                     45

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
gatggatcct gagggtgagg gtgaggg                                         27

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gttgtaaaac gacggccagt                                                 20

<210> SEQ ID NO 17

```
<211> LENGTH: 21
<212> TYPE: DNA
<213> ORGANISM: Artificial Sequence
<220> FEATURE:
<223> OTHER INFORMATION: Synthetic

<400> SEQUENCE: 17
tcacacagga aacagctatg a                                             21

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tgctcggccg atctggcatc                                               20

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ccctaaccct aaccctaacc ctaa                                          24

<210> SEQ ID NO 20
<211> LENGTH: 39
<212> TYPE: DNA
<213> ORGANISM: Artificial Sequence
<220> FEATURE:
<223> OTHER INFORMATION: Synthetic

<400> SEQUENCE: 20
cggtttgttt gggtttgggt ttgggtttgg gtttgggtt                          39

<210> SEQ ID NO 21
<211> LENGTH: 39
<212> TYPE: DNA
<213> ORGANISM: Artificial Sequence
<220> FEATURE:
<223> OTHER INFORMATION: Synthetic

<400> SEQUENCE: 21
ggcttgcctt acccttaccc ttacccttac ccttaccct                          39

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
aagggaagcg ggtcgttatg                                               20

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
```

```
gcagaatttg atgcttggga c                                              21
```

```
<210> SEQ ID NO 24
<211> LENGTH: 19
<212> TYPE: DNA
<213> ORGANISM: Artificial Sequence
<220> FEATURE:
<223> OTHER INFORMATION: Synthetic

<400> SEQUENCE: 24
tcaccattgg caatgagcg                                                 19
```

```
<210> SEQ ID NO 25
<211> LENGTH: 22
<212> TYPE: DNA
<213> ORGANISM: Artificial Sequence
<220> FEATURE:
<223> OTHER INFORMATION: Synthetic

<400> SEQUENCE: 25
tggagttgaa ggtagtttcg tg                                             22
```

```
<210> SEQ ID NO 26
<211> LENGTH: 17
<212> TYPE: DNA
<213> ORGANISM: Artificial Sequence
<220> FEATURE:
<223> OTHER INFORMATION: Synthetic

<400> SEQUENCE: 26
tggacctgac ctgccgt                                                   17
```

```
<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
tggaggagtg ggtgtcgc                                                  18
```

```
<210> SEQ ID NO 28
<211> LENGTH: 90
<212> TYPE: DNA
<213> ORGANISM: Artificial Sequence
<220> FEATURE:
<223> OTHER INFORMATION: Synthetic

<400> SEQUENCE: 28
ccctaaccct aaccctaacc ctaaccctaa ccctaaccct aaccctaacc ctaaccctaa    60
ccctaaccct aaccctaacc ctaaccctaa                                     90
```

```
<210> SEQ ID NO 29
<211> LENGTH: 90
<212> TYPE: DNA
<213> ORGANISM: Artificial Sequence
<220> FEATURE:
<223> OTHER INFORMATION: Synthetic

<400> SEQUENCE: 29
ccctcaccct caccctcacc ctcaccctca ccctcaccct caccctcacc ctcaccctca    60
ccctcaccct caccctcacc ctcaccctca                                     90
```

```
<210> SEQ ID NO 30
<211> LENGTH: 90
<212> TYPE: DNA
<213> ORGANISM: Artificial Sequence
<220> FEATURE:
<223> OTHER INFORMATION: Synthetic

<400> SEQUENCE: 30
ccctgaccct gaccctgacc ctgaccctga ccctgaccct gaccctgacc ctgaccctga      60
ccctgaccct gaccctgacc ctgaccctga                                      90
```

MULTIPLEX QUANTITATIVE PCR

CROSS-REFERENCE TO RELATED APPLICATIONS

This application claims the benefit of U.S. Provisional Application Nos. 62/098,057, filed on Dec. 30, 2014, and 62/163,434, filed on May 19, 2015, each of which is incorporated herein by reference in its entirety.

REFERENCE TO A SEQUENCE LISTING SUBMITTED AS A TEXT FILE VIA EFS-WEB

The Sequence Listing submitted Jun. 22, 2015 as a text file named "37502_0004U3_updated_ST25.txt," created on Jun. 22, 2015, and having a size of 6,206 bytes is hereby incorporated by reference pursuant to 37 C.F.R. §1.52(e)(5).

BACKGROUND OF THE INVENTION

The statements in the Background are not necessarily meant to endorse the characterization in the cited references.

Telomeres, the tips of eukaryotic chromosomes, protect the chromosomes from nucleolytic degradation, end-to-end fusion, and recombination. Telomeres are structures at the ends of chromosomes characterized by repeats of the nucleotide sequence $(5'-TTAGGG-3')_n$. Telomeres shorten as a consequence of normal cell division and critically short telomeres lead to cellular senescence or apoptosis. A rich body of epidemiological and clinical studies in humans in the past decade has linked short telomere length to high risks of aging-related disease and all-cause mortality (Puterman, E. and E. Epel, Soc Personal Psychol Compass, 2012. 6(11) 807-825; Zhu, H., M. Belcher, and P. van der Harst, Clin Sci (Lond), 2011. 120(10) 427-40; and Fyhrquist, F. and O. Saijonmaa. Ann Med, 2012. 44 Suppl 1 S138-42). Genetic, environment, lifestyle, and behavioral factors collectively impact telomere length. Therefore, telomere length has become an index for overall health, disease, and mortality risk.

While average telomere length was measured in almost all the clinical studies published and has demonstrated utility in stratifying patient disease and mortality risk, recent work in mice has also shown that the population of short telomeres is the triggering signal to senescence or apoptosis (Hemann, M. T., et al. Cell, 2001. 107(1) 67-77), and thus disease and mortality risk. In a study reported by Hemann et al, 6th generation telomerase RNA knockout mice (mTR−/− G6) with short telomeres were crossed with mice heterozygous for telomerase (mTR+/−) with long telomeres. The phenotype of the telomerase null offspring mirrors that of the mTR−/− parent despite the fact that half of their telomeres are long, suggesting that the quantity of short telomeres, and not average telomere length, is critical for cell viability and chromosome stability. In people taking a natural product-derived telomerase activator (TA-65®), a significant reduction in the percentage of short (<3 or <4 kbp) telomeres (as measured by a quantitative FISH technology; see (Canela, A., et al. Proc Natl Acad Sci USA, 2007. 104(13) 5300-5) was detected in the leukocytes, although no change in mean telomere length was seen (Harley, C. B., et al., Rejuvenation Res. 2011. 14(1) 45-56). Changes in the percentage of short telomere abundance therefore is expected to be a more sensitive measurement of the effects of lifestyle and pharmacological or other interventions on telomeres. Another study (Vera et al., "The Rate of Increase of Short Telomeres Predicts Longevity in Mammals", Cell Reports (2012), world wide web URL: dx.doi.org/10.1016/.celrep.2012.08.023) found that "the rate of increase in the abundance of short telomeres was a predictor of lifespan".

Various methods have been developed for the measurement of telomere length, including Southern blotting (Kimura, M. et al., Nature Protocols, 2010, 5:1596-1607), Q-FISH (Rufer, N. et al., Nat. Biotechnol., 1998, 16:743-747), flow FISH (Baerlocher, G. M. et al., Cytometry, 2002, 47:89-99), a higher throughput modification of the Q-FISH assay (HTQ-FISH; see Canela, A. et al., PNAS, 2007, 104: 5300-5305), dual-label centromeres and telomeres FISH (Cen/Tel FISH) (Vander Griend D. J., et al. Prostate 2009 Oct. 1; 69(14):1557-64. doi: 10.1002/pros.21001), dot blot (Kimura M, Aviv A. 2011 NAR), and qPCR (Cawthon, R. M., Nucleic. Acids Res., 2002, 30(10):e47; and Cawthon R M. Nucleic Acids Res. 2009, 37(3):e21).

q-PCR-telomere length (qPCR-TL) measures the abundance of average telomeres normalized with a single copy gene, expressed as T/S ratios. To convert T/S ratios to absolute length in number of bp, telomere restriction fragment length (TRF) various methods have been reported. For example, it was previously reported that this conversion could be determined by Southern blot analysis and compared to T/S ratios (Cawthon, ibid). A linear regression formula was obtained and used to calculate the TRF length of an unknown sample based on its T/S ratio. One critical issue with this conversion is that TRF contains a region of non-telomeric sequence at its centromeric end (subtelomeric sequence). Because the length of subtelomeric sequence varies among individuals, the converted by from T/S ratios based on TRF is only an approximation.

Thus, despite advances in materials and methods for facile determination of relative telomere length or abundance, there remains a need for improved methods and materials for determining differences in telomere length or abundance in subjects compared to appropriate control populations. In particular, there remains a need to determine with great accuracy differences in the relative telomere length or abundance in a subject in order to improve clinical assessments and/or therapeutic regimens in those same subjects. These needs and other needs are addressed by the present invention.

SUMMARY OF THE INVENTION

In accordance with the purpose(s) of the invention, as embodied and broadly described herein, the invention, in one aspect, relates to methods and compositions for determining the average length or abundance of at least three target nucleic acid sequences in a single qPCR multiplexed reaction utilizing a different detection label for each target nucleic acid sequence. In one aspect, one of the three target nucleic acid sequences is a telomeric sequence and the other two target nucleic acid sequences are distinct low copy number genes known to rarely undergo copy number variations. In a further aspect, the ratio of the average telomere length or abundance to the average of the average abundance for the other two nucleic acid sequences, i.e., the T/S ratio can be used for associating the average telomere length or abundance with clinical risks or optimized therapeutic regimens. In a still further aspect, the low copy number genes are single copy genes.

Disclosed are methods for determining average telomere length, comprising: (a) contacting a first target nucleic acid with a first primer set, a second target nucleic acid with a second primer set, and a third target nucleic acid target with a third primer set; (i) wherein the first primer set comprises a first forward primer and a first reverse primer; (ii) wherein the second primer set comprises a second forward primer and a second reverse primer; (iii) wherein the third primer set comprises a third forward primer and a third reverse primer; and (iv) wherein the first target nucleic acid comprises a telomere repeat sequence; (b) selectively amplifying by polymerase chain reaction the first target nucleic acid with the first primer set to form a first amplicon, the second target nucleic acid with the second primer set to form a second amplicon, and the third target nucleic acid with the third primer set to form a third amplicon; (c) determining during one or more cycles of the polymerase chain reaction the amount of the first, second, and third amplicons; (i) wherein the first amplicon is detected using a first detection label; (ii) wherein the second amplicon is detected using a second detection label; and (iii) wherein the third amplicon is detected using a third detection label; and (d) determining the average length or abundance of the first amplicon.

Also disclosed are methods for allogeneic transplant hematopoietic stem cell donor selection, the method comprising: (a) obtaining samples from one or more HLA-matched potential donor subjects; (b) determining the average length or abundance of the first amplicon for each of the HLA-matched donor subjects by the disclosed methods; (c) identifying one or more donor subjects with a first amplicon average length or abundance that is in upper $25^{th}$ percentile for age-matched controls; (d) obtaining a transplantable hematopoietic stem cell sample from the identified donor subject; and (e) transplanting the hematopoietic stem cell sample to a recipient subject.

Also disclosed are methods for reclassification of cardiovascular disease risk, the method comprising: (a) obtaining a sample from a subject, wherein the subject has been diagnosed to meet 2013 ACC/AHA Guideline on the Treatment of Blood Cholesterol criteria for low-intensity statin therapy; (b) determining average length or abundance of the of the first amplicon in the sample by the disclosed methods; (c) diagnosing the subject at higher cardiovascular risk when the sample has been determined to have a first amplicon average length or abundance in the lower $25^{th}$ percentile for age-matched controls; and (d) administering to the subject diagnosed at higher cardiovascular risk: (i) a modified statin therapy; and/or (ii) a second therapeutic agent known to treat cardiovascular disease.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 1A shows the first cycle of amplification. Briefly, the TelG-modified primer ("Tel G modified") binds along native telomeres at multiple telomeric sites, whereas the TelC-modified primer ("Tel C modified") cannot bind along native telomere sites due to the mismatch at the terminal 3' end of the Tel C modified primer. Accordingly, the abundance of the Tel G modified extension products is proportional to the abundance of C-strand telomeric DNA. FIG. 1B shows that the Tel G modified and Tel C modified primers cannot form primer dimers due to the mismatches, particularly at the 3' end of each primer. Data from no-template controls (NTC) confirm that these primers do not amplify in the absence of telomeric DNA. FIG. 1C shows the second cycle of amplification. Briefly, the multiple extension products synthesized in the first amplification cycle 1 from the Tel G modified primer provide binding sites for the Tel C modified primer. The bound Tel C modified primer can be extended to the 5' end of the extension products from first amplification cycle that were primed by the Tel G modified primer. Accordingly, in cycle 3 and thereafter, an 86 bp duplex is preferentially amplified. The abundance of this amplicon is designed to be proportional to the abundance of double-stranded telomeric DNA in the genomic DNA sample.

FIG. 3A shows the Cp versus log (concentration) for the telomere target nucleic acid using the Tel G modified and Tel C modified primers. FIG. 3B shows the Cp versus log (concentration) for the RNase P target nucleic acid using the RNAP-F and RNAP-R primers. FIG. 3C shows the Cp versus log (concentration) for the β2-microglobulin target nucleic acid using the B2M-F and B2M-R primers. In the foregoing, the concentration used in the log (concentration) expression was in units of ng/µL.

FIG. 4A shows the amplification curve using the Tel G modified and Tel C modified primers. As shown in FIG. 4A, telomeric DNA typically amplifies with significant signal (Fluorescent signals >25 units) in the Cp range of 20-25, while the NTCs show essentially background noise (fluorescent units below 1, even at 30 cycles or more). This demonstrates the absence of non-specific amplifications throughout the relevant cycles of qPCR amplification. FIG. 4B shows the amplification curve using the RNAP-F and RNAP-R primers. FIG. 4C shows the amplification curve using the B2M-F and B2M-R primers.

FIG. 5A-FIG. 5C show representative amplification curves from amplification reactions carried out using without human genomic DNA (i.e., a non-template control reaction). FIG. 5A shows the amplification curve using the Tel G modified and Tel C modified primers without target genomic DNA. Note that there is essentially no amplification of any DNA until after cycle 30. FIG. 5B shows the amplification curve using the RNAP-F and RNAP-R primers. FIG. 5C shows the amplification curve using the B2M-F and B2M-R primers.

FIG. 6A shows a representative histogram of T/S ratios determined using the disclosed methods with the B2M-F, B2M-R, RNAP-F, RNAP-R, Tel G modified, and Tel C modified primers in reactions carried out on 163 independent samples from research subjects. The T/S ratio is determined by dividing the concentration of the telomeric DNA amplicon from the qPCR reaction, by the average concentration of the RNase P and β2-microglobulin amplicons from the qPCR reaction, where all three amplicons are in a single reaction well. The graph shows a log-normal distribution of T:S ratios, as expected for distribution of telomere lengths. FIG. 6B shows a representative graph of T/S ratios versus age using the disclosed methods with the B2M-F, B2M-R, RNAP-F, RNAP-R, Tel G modified, and Tel C modified primers in reactions carried out on 163 samples from healthy research participants.

FIG. 13A shows the results obtained for each primer in a reaction containing 1×DNA (1.67 ng/μL), whereas FIG. 13B under the same conditions except using 7×DNA (11.69 ng/μL). FIG. 13C and FIG. 13D show the calculated average telomere concentration using the data in FIGS. 13A and 13B, respectively.

FIG. 14A shows the results obtained for each primer in a reaction containing 1×DNA (1.67 ng/μL), whereas FIG. 14B under the same conditions except using 7×DNA (11.69 ng/μL). FIG. 14C shows the calculated average telomere concentration using the data in FIGS. 14A and 14B.

FIG. 15A shows the results obtained for each primer in a reaction containing 1×DNA (1.67 ng/μL), whereas FIG. 15B under the same conditions except using 7×DNA (11.69 ng/μL). FIG. 15C shows the calculated average telomere concentration using the data in FIGS. 15A and 15B.

Figure 1A:
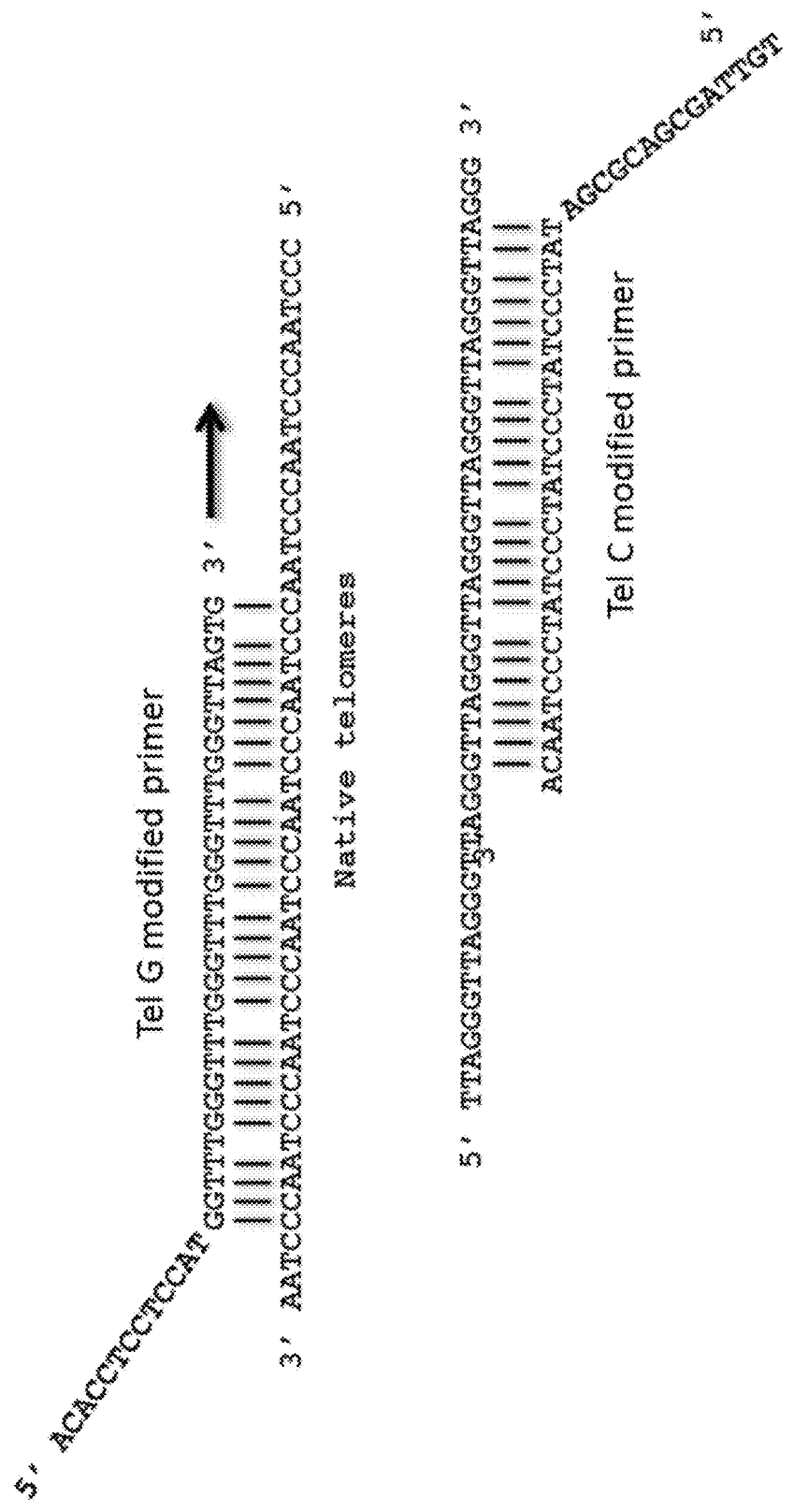
FIG. 1A-FIG. 1C show representative schematic schemes for the amplification of a telomere target sequence.
Figure 1B:
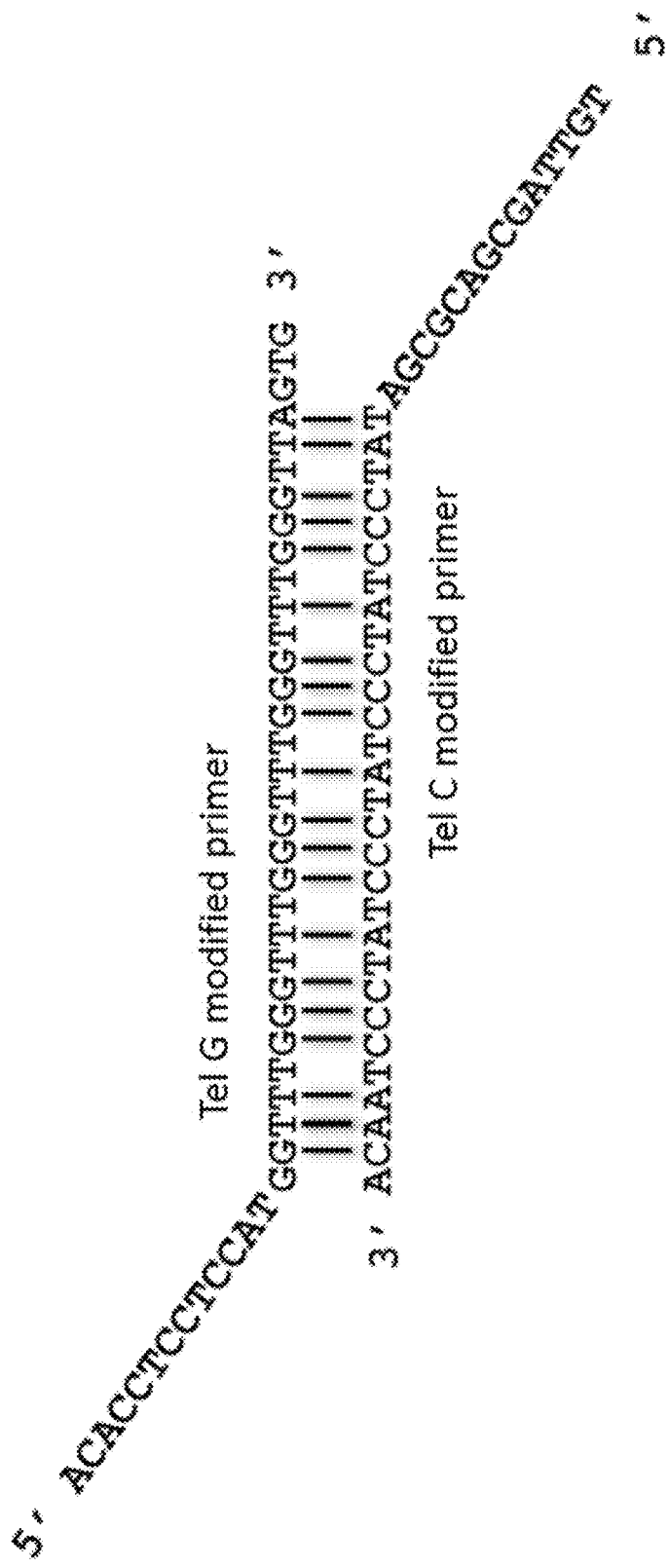
Figure 1C:
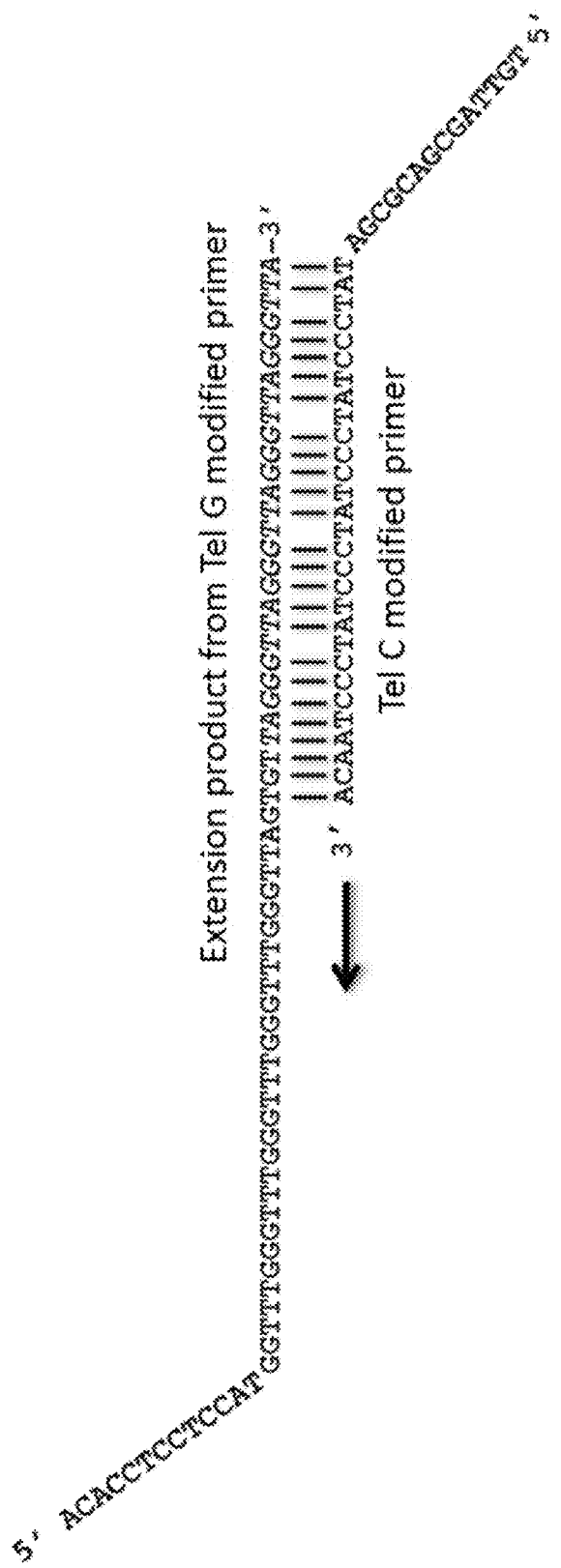
Figure 2A:
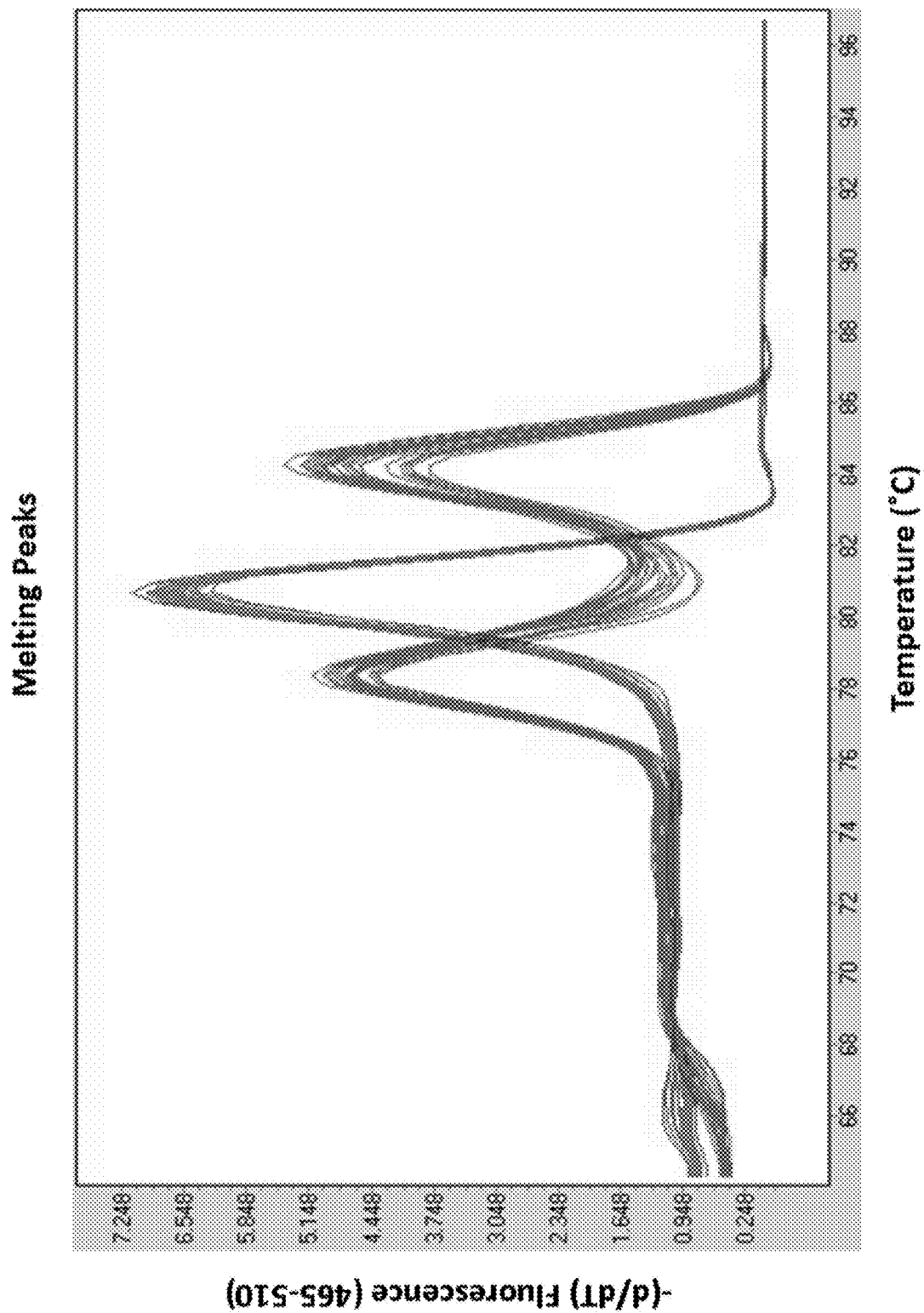
FIG. 2A-FIG. 2F show representative melting curve data for amplification with B2M-F, B2M-R, RNAP-F, RNAP-R, Tel G modified, and Tel C modified primers with human genomic target DNA (mosaic male genomic DNA). The concentration of the Tel G modified and Tel C modified primers were varied as indicated in the figures. The concentration of the B2M-F and B2M-R primers was held constant at 300 nM, and the B2M-probe was present at a concentration of 100 nM.
Figure 2B:
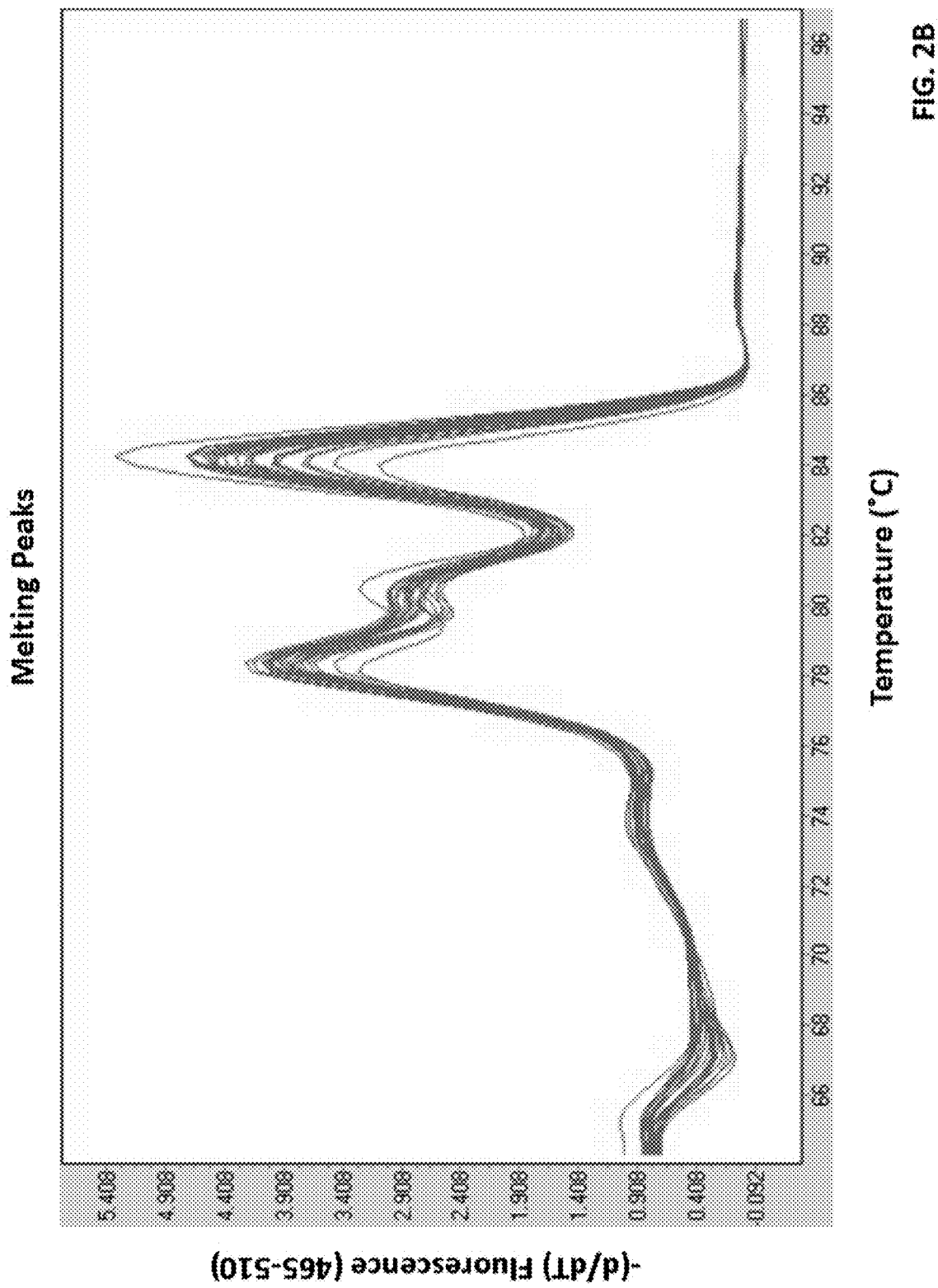
Figure 2C:
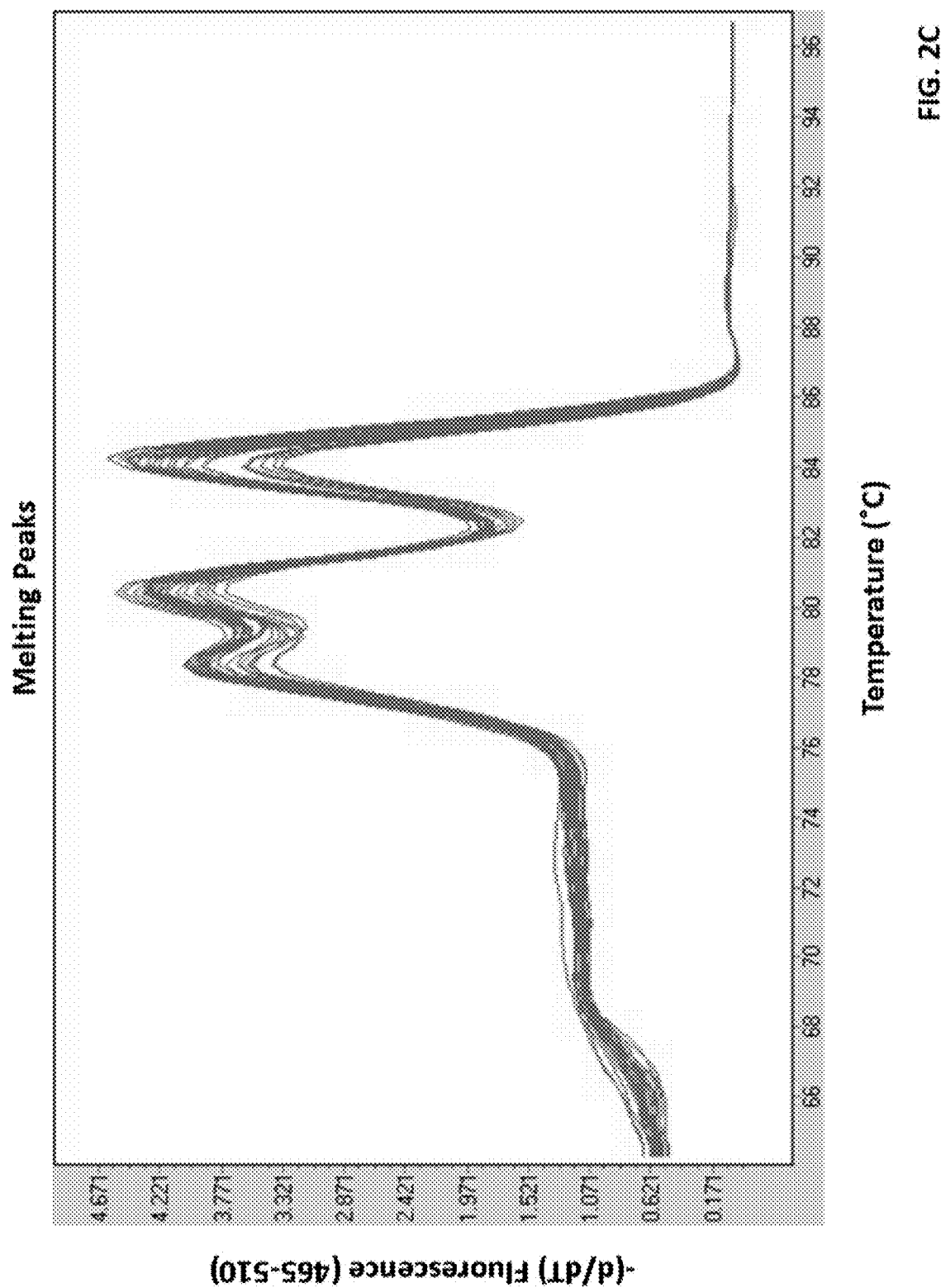
Figure 2D:
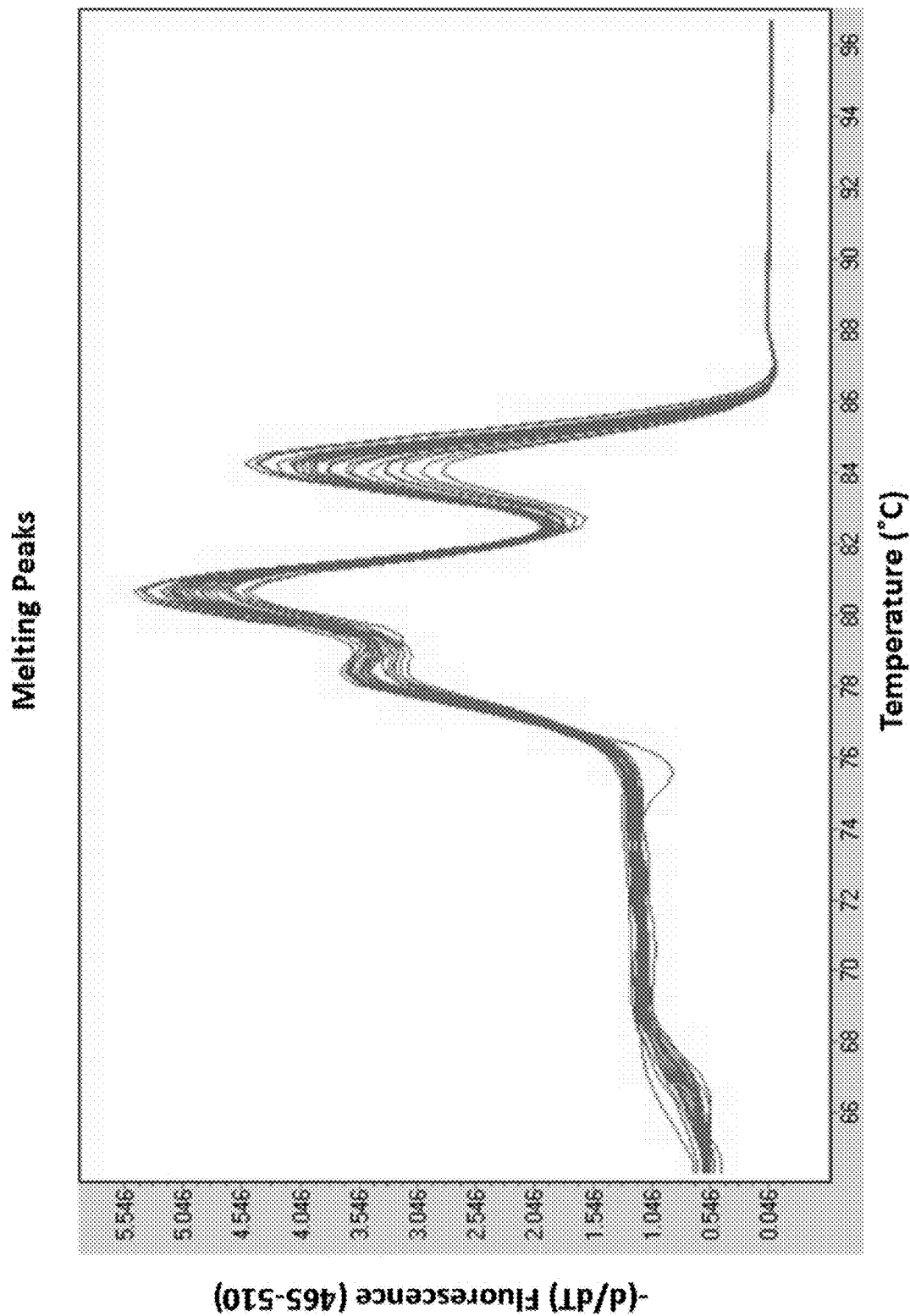
Figure 2E:
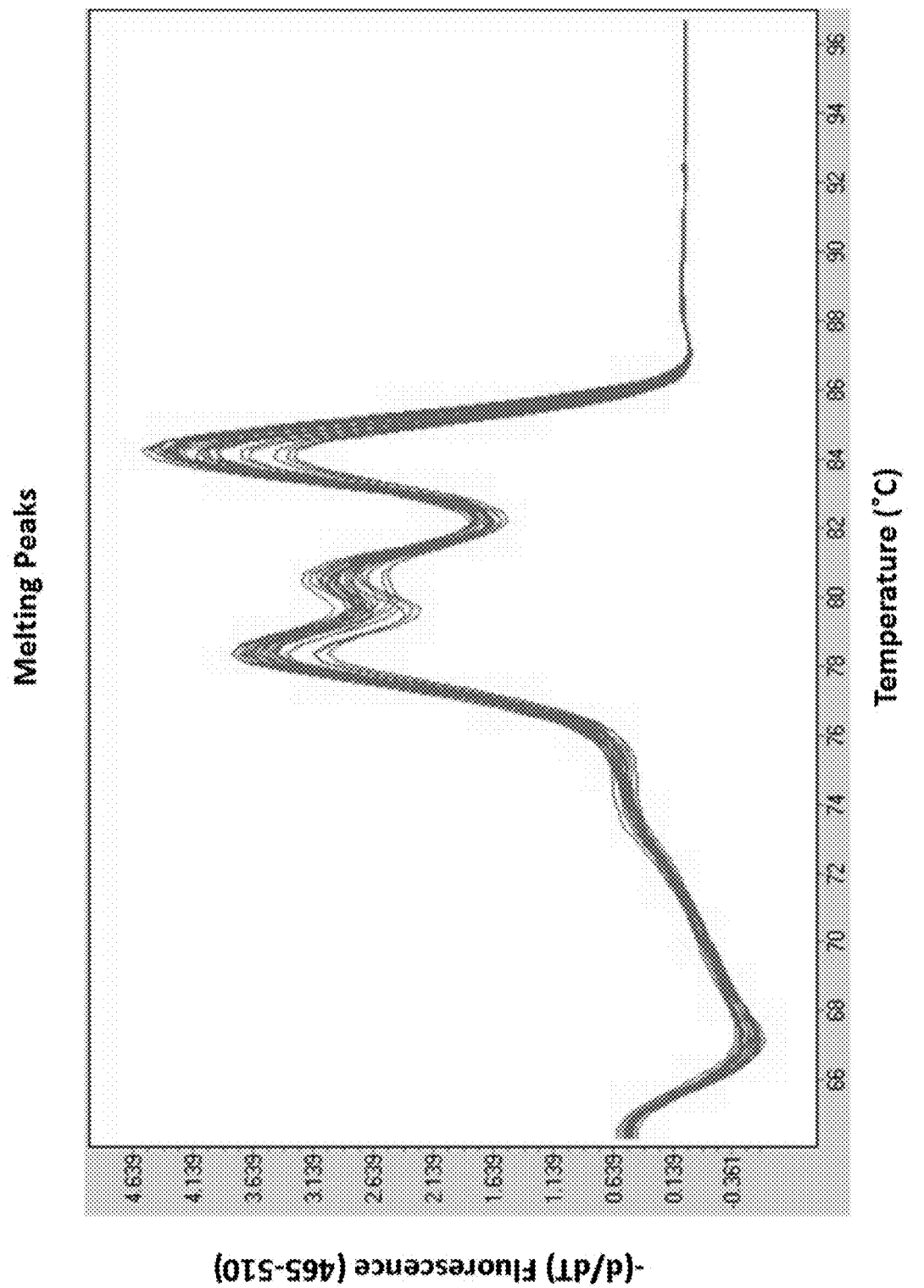
Figure 2F:
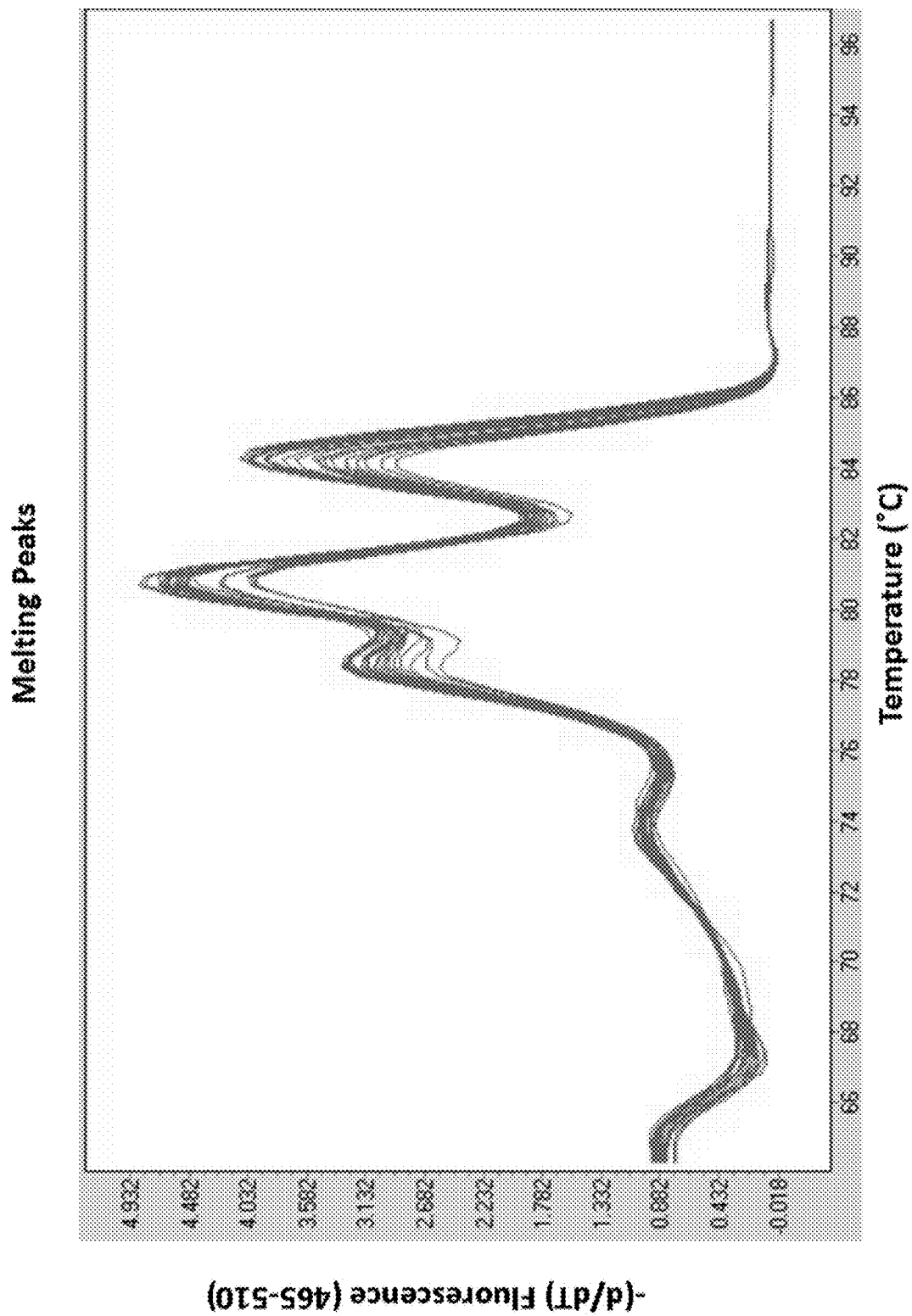

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

The present disclosure can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior invention. Further, the dates of publication provided herein can be different from the actual publication dates, which can require independent confirmation.

As used in the specification and in the claims, the term "comprising" can include the aspects "consisting of and" "consisting essentially of."

As used herein, nomenclature for compounds, including organic compounds, can be given using common names, IUPAC, IUBMB, or CAS recommendations for nomenclature. Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a cell," "a nucleotide," or "a primer" includes mixtures of two or more such cells, nucleotides, or primers, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "effective amount" refers to an amount that is sufficient to achieve the desired modification of a physical, chemical, or biological property of the composition or method.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a condition, disease or disorder. The term "patient" includes human and veterinary subjects. In some aspects of the disclosed methods, the subject has been diagnosed with a need for treatment of one or more conditions or diseases associated with altered telomere length. For example, a subject with a particular clinical condition can have cells with chromosomes having an altered telomere length resulting from a dysfunction in telomerase activity. In such conditions, the dysfunction in telomerase activity leads to critically short telomeres ("telomere disease").

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "extension primer" means an oligonucleotide primer used to perform the time-limited extension reaction step carried out by a DNA polymerase. The extension primer can comprise a 3' portion and a 5' portion. For example, the 3' portion can hybridize to a telomeric repeat sequence in the 3' overhang under annealing conditions, and a 5' portion can have an anchor sequence that does not hybridize to a telomeric repeat sequence in the 3' overhang under the annealing conditions.

As used herein, "telomeric region" means the double-stranded DNA segment at the ends of a chromosome with repeat telomeric sequence (TTAGGG:CCCTAA repeats).

As used herein, "sub-telomeric region" means the segment of DNA immediately adjacent to telomere at the centromeric side of telomeres. A sub-telomeric region often contains degenerate telomeric repeats. In the case of humans, repeats of TGAGGG and TCAGGG can be present in the sub-telomeric region.

As used herein, "anchor sequence" means a unique sequence segment within a primer that is not present in the template genome that can be used in the PCR reaction or present within 20 kb of the intended amplicon. For example, the 5' portion of an extension primer can be an anchor sequence that is configured not to hybridize under annealing conditions to a telomeric repeat sequence in the G-strand to which the 3' portion of the extension primer hybridizes and not to hybridize to any other sequence present in the template sequence within 20 kb of the telomeric repeat.

As used herein, the "G-strand of the chromosomal DNA" means the strand of the telomere having the 3' overhang, and includes the telomeric repeat sequence 5'-TTAGGG-3'. For example, "G-strand of the chromosomal DNA" can refer to the DNA strand in a chromosome comprising the $(TTAGGG)_n$ telomeric repeat sequence in humans and other vertebrates.

As used herein, the "C-strand of the chromosomal DNA" means the strand complementary to the G-strand of the chromosomal DNA, and comprises the (CCCTAA)n telomeric repeat sequence in humans and other vertebrates.

As used herein, "mosaic composition genomic DNA" means a genomic DNA sample that is a pooled sample comprising individual donor DNA samples. The pool comprises individual samples obtained from at least two unrelated sample donors. Typically, mosaic composition genomic DNA is a pooled sample comprising individual genomic DNA samples obtained from about 50-100 individual, unrelated sample donors. In some cases, the individual, unrelated sample donors are of a single gender, e.g., mosaic composition genomic DNA obtained only from individual, unrelated male donors. In other cases, the individual, unrelated sample donors are from both genders. "Mosaic composition genomic DNA" can be used interchangeably with other terms such as "mosaic template DNA," "mosaic genomic DNA," "mosaic DNA," and the like.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides in a sequence specific manner complementing the nucleic acid the primer is annealed to resulting in a double-stranded DNA molecule. Known DNA polymerases include, for example, *Pyrococcus furiosus* (Pfu) DNA polymerase (Lundberg et al., (1991) Gene 108:1), *E. coli* DNA polymerase I (Lecomte and Doubleday (1983) Nucleic Acids Res. 11:7505), T7 DNA polymerase (Nordstrom et al. (1981) J. Biol. Chem. 256:3112), *Thermus thermophilus* (Tth) DNA polymerase (Myers and Gelfand (1991) Biochemistry 30:7661), *Bacillus stearothermophilus* DNA polymerase (Stenesh and McGowan (1977) Biochim Biophys Acta 475:32), *Thermococcus litoralis* (Tli) DNA polymerase (also referred to as Vent DNA polymerase, Cariello et al. (1991) Nucleic Acids Res 19:4193), *Thermotoga maritima* (Tma) DNA polymerase (Diaz and Sabino (1998) Braz J. Med. Res 31:1239), and *Thermus aquaticus* (Taq) DNA polymerase (Chien et al., (1976) J. Bacteoriol 127:1550). The polymerase activity of any of the above enzymes can be determined by means well known in the art.

As used herein, "thermostable" DNA polymerase activity means DNA polymerase activity which is relatively stable to heat and functions at high temperatures, for example 45-100° C., preferably 55-100° C., 65-100° C., 75-100° C., 85-100° C. or 95-100° C., as compared, for example, to a non-thermostable form of DNA polymerase.

As used herein, "primer" refers to an oligonucleotide capable of acting as a point of initiation of DNA synthesis under conditions in which synthesis of a primer extension product complementary to a nucleic acid strand is induced, e.g., in the presence of four different nucleoside triphosphates and an agent for extension (e.g., a DNA polymerase or reverse transcriptase) in an appropriate buffer and at a suitable temperature. A primer need not reflect the exact sequence of the template nucleic acid, but must be sufficiently complementary to hybridize with the template. The design of suitable primers for the amplification of a given target sequence is well known in the art and described in the literature cited herein.

The terms "target," "target sequence," "target region," and "target nucleic acid," as used herein, are synonymous and refer to a region or subsequence of a nucleic acid which is to be amplified or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., (1989) Molecular Cloning—A Laboratory Manual (Cold Spring Harbor Laboratory, Cold Spring Harbor, N.Y.); and Wetmur (1991) Critical Review in Biochem. and Mol. Biol. 26 (3/4):227-259; both incorporated herein by reference).

The term "amplification reaction" refers to any chemical reaction, including an enzymatic reaction, which results in increased copies of a template nucleic acid sequence or results in transcription of a template nucleic acid.

Polymerase chain reaction (PCR) is a method that allows exponential amplification of DNA sequences within a longer double stranded DNA molecule. PCR entails the use of a pair of primers that are complementary to a defined sequence on each of the two strands of the DNA with one primer being complementary to one strand and the other primer being complementary to the other strand of the target sequence. These primers are extended by a DNA polymerase so that a copy is made of the designated sequence. After making this copy, the same primers can be used again, not only to make another copy of the input DNA strand but also of the short copy (PCR amplicon) made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 20 to 40) rounds of amplification, the PCR product is analyzed on an agarose gel and is abundant enough to be detected with an DNA intercalating or binding dye, e.g., ethidium bromide, SYBR® Green, or EvaGreen® dye.

It is understood that real-time PCR, also called quantitative real time PCR (qRT-PCR), quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample.

As used herein, a primer is "specific," for a target sequence if, when used in an under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "Tm" means the melting temperature, or annealing temperature, of a nucleic acid duplex at which, under specified conditions, half of the base pairs have disassociated. Those skilled in the art of nucleic acid technology can determine duplex stability empirically considering a number of variables including, for example, the length of the oligonucleotide, base composition and sequence of the oligonucleotide, ionic strength, and incidence of mismatched base pairs. The "predicted Tm," as used herein, means the temperature at which a primer and its complementary template sequence are predicted to be sufficiently stable to permit hybridization and extension by PCR, and can be determined using the nearest neighbor algorithm (Von-Ahsen N et al. (1999) Clinical Chemistry, 45(12):2094-2101). An exemplary software tool for determining the predicted Tm for oligonucleotides and primers is provided on the websites of many vendors selling oligonucleotides (e.g. Integrated DNA Technologies, Inc.).

The term "probe," as used herein, refers to a labeled oligonucleotide which forms a duplex structure with a sequence in the target nucleic acid, due to complementarity of at least one sequence in the probe with a sequence in the target region. The probe preferably does not contain a sequence complementary to sequence(s) used to prime the polymerase chain reaction.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

As used herein, "substantially complementary" means that the complementarity between a nucleic acid molecule that can form with another nucleic acid is sufficient that hybridization can occur under the desired or specified conditions. Thus, the two nucleic acid strands need not be complementary at each and every nucleotide of the two strands. When the term "substantially complementary" is used with primers, it means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. In some situations, it is desirable that the primers have exact complementarity to obtain the best detection results. However, there are other situations where it is desirable that the primers have random mismatches, or alternatively, specific mismatches are designed into the primers.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions.

The term "primer dimer," as used herein, refers to a template-independent non-specific amplification product, which is believed to result from primer extensions wherein another primer serves as a template. Although primer dimers frequently appear to be a concatemer of two primers, i.e., a dimer, concatemers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions or in "master mixes", each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

The abbreviations and terms described in Table 1 are used herein throughout.

TABLE 1

| Term | Definition |
| --- | --- |
| bp(s) | base pair(s) |
| nt(s) | nucleotide(s) |
| U | enzymatic units (as defined in the art for the indicated enzyme) |
| DNA | deoxyribonucleic acid |
| RNA | ribonucleic acid |
| qPCR-TL | qPCR telomere length |
| TRF | telomere restriction fragment length |
| aTL | absolute telomere length |
| ATL | average telomere length |
| T | telomere repeat sequence |
| R | RNase P single copy gene |
| B | B2M single copy gene |
| T/S ratio | Telomere length ratio based on the ratio of telomere products and the average of B2M and RNase P products |
| qPCR | Quantitative polymerase chain reaction |
| QC DNA | Quality control DNA |
| QC1 | Human genomic DNA obtained from pooled whole blood samples from female and male donors |
| QC2 | Human genomic DNA from 100 female donors |
| QC3 | Human genomic DNA obtained from placental tissue |
| Tel G modified | Telomere forward primer |
| Tel C modified | Telomere reverse primer |
| B2M-F | β2-microglobulin forward primer |
| B2M-R | β2-microglobulin reverse primer |
| B2M-P | β2-microglobulin amplicon detection probe that is a Cy5 ® dye-labeled, Iowa Black ® RQ quenched probe. |
| RNAP-F | RNase P forward primer, TaqMan ® Copy Number Reference Assay RNase P kit, Cat. No. 4403326 or 4403328 (Thermo Fisher Scientific Inc.). |
| RNAP-R | RNase P reverse primer, TaqMan ® Copy Number Reference Assay RNase P kit, Cat. No. 4403326 or 4403328 (Thermo Fisher Scientific Inc.). |
| RNAP-P | RNase P detection probe that is a VIC ® dye-labeled, TAMRA ™ dye-quenched probe, TaqMan ® Copy Number Reference Assay RNase P kit, Cat. No. 4403326 or 4403328 (Thermo Fisher Scientific Inc.). |
| Reference standard DNA | Mosaic M DNA used to establish standard curves for input DNA |
| Mosaic M DNA | NIST-calibrated human genomic DNA from 100 male donors. The genomic DNA is purified so that 90% of the material is greater than or equal to 50 kb. |
| Pulse spin | A short treatment of a sample in microcentrifuge in a microcentrifuge wherein the sample is spun for a period of about 5 seconds, then released. |

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

1. Triplex qPCR Assay Method

The present disclosure discloses methods and materials for determining measures of average telomere length or abundance in a population of chromosomes and of using these measures for determining measures of health or disease risk, or effects of interventions that increase or decrease telomere length and, hence, increase or decrease health, or conversely decrease or increase risk of future disease or death, respectively, or to improve the practice of medicine by providing added value through telomere-based guidance to physicians. The methods involve determining the average telomere length or abundance of at least three target nucleic acid sequences in a single qPCR multiplexed reaction utilizing a different detection label for each target nucleic acid sequence. In one aspect, one of the three target nucleic acid sequences is a telomeric sequence and the other two target nucleic acid sequences are distinct low copy number genes known to rarely undergo copy number variation. In a further aspect, the low copy number genes are single copy genes known to rarely undergo copy number variation. In a further aspect, the ratio of the average telomere length or abundance to average of the average length or abundance for the other two nucleic acid sequences, i.e., the T/S ratio, where "S" is the average of the two single low copy genes, can be used to determine a specific clinical risk. Alternatively, the T/S ratio can be used for optimizing therapeutic regimens.

In one aspect, the present disclosure pertains to methods for determining average telomere length, comprising: (a) contacting a first target nucleic acid with a first primer set, a second target nucleic acid with a second primer set, and a third target nucleic acid target with a third primer set; (i) wherein the first primer set comprises a first forward primer and a first reverse primer; (ii) wherein the second primer set comprises a second forward primer and a second reverse primer; (iii) wherein the third primer set comprises a third forward primer and a third reverse primer; and (iv) wherein the first target nucleic acid comprises a telomere repeat sequence; (b) amplifying by polymerase chain reaction the first target nucleic acid with the first primer set to form a first amplicon, the second target nucleic acid with the second primer set to form a second amplicon, and the third target nucleic acid with the third primer set to form a third amplicon; (c) determining during one or more cycles of the polymerase chain reaction the amount of the first, second, and third amplicons; (i) wherein the first amplicon is detected using a first detection label; (ii) wherein the second amplicon is detected using a second detection label; and (iii) wherein the third amplicon is detected using a third detection label; and (d) determining the average length or abundance of the first amplicon.

In various aspects, determining the average length or abundance of the first amplicon comprises the steps: (a) determining the concentration of the first, second, and third amplicon by comparison to a control polymerase chain reaction; (b) determine the ratio of the concentration of the first amplicon to the average or weighted concentration of the second and third amplicons; and (c) converting the ratio from step (b) to base pairs of telomere sequence per genome.

In one aspect, the present disclosure pertains to methods for determining average telomere length, comprising: (a) contacting a first target nucleic acid with a first primer set, a second target nucleic acid with a second primer set, a third target nucleic acid target with a third primer set; and a fourth target nucleic acid target with a fourth primer set; (i) wherein the first primer set comprises a first forward primer and a first reverse primer; (ii) wherein the second primer set comprises a second forward primer and a second reverse primer; (iii) wherein the third primer set comprises a third forward primer and a third reverse primer; (iv) wherein the fourth primer set comprises a fourth forward primer and a fourth reverse primer; and (v) wherein the first target nucleic acid comprises a telomere repeat sequence; (b) amplifying by polymerase chain reaction the first target nucleic acid with the first primer set to form a first amplicon, the second target nucleic acid with the second primer set to form a second amplicon, the third target nucleic acid with the third primer set to form a third amplicon, and the fourth target nucleic acid with the fourth primer set to form a fourth amplicon; (c) determining during one or more cycles of the polymerase chain reaction the amount of the first, second, and third amplicons; (i) wherein the first amplicon is detected using a first detection label; (ii) wherein the second amplicon is detected using a second detection label; (iii) wherein the third amplicon is detected using a third detection label; and (iv) wherein the fourth amplicon is detected using a fourth detection label; and (d) determining the average length or abundance of the first amplicon.

In various aspects, determining the average length or abundance of the first amplicon comprises the steps: (a) determining the concentration of the first, second, third, and fourth amplicon by comparison to a control polymerase chain reaction; (b) determine the ratio of the concentration of the first amplicon to the average or weighted concentration of the second, third, and fourth amplicons; and (c) converting the ratio from step (b) to base pairs of telomere sequence per genome.

In one aspect, the present disclosure pertains to methods for determining average telomere length, comprising: (a) contacting a first target nucleic acid with a first primer set, a second target nucleic acid with a second primer set, a third target nucleic acid target with a third primer set; a fourth target nucleic acid target with a fourth primer set, and a fifth target nucleic acid target with a fourth primer set; (i) wherein the first primer set comprises a first forward primer and a first reverse primer; (ii) wherein the second primer set comprises a second forward primer and a second reverse primer; (iii) wherein the third primer set comprises a third forward primer and a third reverse primer; (iv) wherein the fourth primer set comprises a fourth forward primer and a fourth reverse primer; (v) wherein the fifth primer set comprises a fifth forward primer and a fifth reverse primer; and (vi) wherein the first target nucleic acid comprises a telomere repeat sequence; (b) amplifying by polymerase chain reaction the first target nucleic acid with the first primer set to form a first amplicon, the second target nucleic acid with the second primer set to form a second amplicon, the third target nucleic acid with the third primer set to form a third amplicon, the fourth target nucleic acid with the fourth primer set to form a fourth amplicon, and the fifth target nucleic acid with the fifth primer set to form a fifth amplicon; (c) determining during one or more cycles of the polymerase chain reaction the amount of the first, second, and third amplicons; (i) wherein the first amplicon is detected using a first detection label; (ii) wherein the second amplicon is detected using a second detection label; (iii) wherein the third amplicon is detected using a third detection label; (iv) wherein the fourth amplicon is detected using a fourth detection label; and (v) wherein the fifth amplicon is detected using a fifth detection label; and (d) determining the average length or abundance of the first amplicon.

In various aspects, determining the average length or abundance of the first amplicon comprises the steps: (a) determining the concentration of the first, second, third, and fourth amplicon by comparison to a control polymerase chain reaction; (b) determine the ratio of the concentration of the first amplicon to the average or weighted concentration of the second, third, fourth, and fifth amplicons; and (c) converting the ratio from step (b) to base pairs of telomere sequence per genome.

In various aspects, each of the first forward primer and the first reverse primer comprise: (a) a 3' portion that hybridizes to a telomeric repeat sequence under annealing conditions; and (b) a 5' portion having an anchor sequence that does not hybridize to a telomeric repeat sequence. In a further aspect, the 3' ends of the primers of the first forward primer and the first reverse primer are complementary to each other. In a still further aspect, the first reverse primer is a mismatch primer comprising at least one mismatched nucleotide adjacent to or including the 3' end of the primer, wherein the at least one mismatched nucleotide is not complementary to the target nucleic acid, but is complementary to the 3' terminal nucleotide of the first forward primer. In a yet further aspect, the extension product of the first forward primer is capable of hybridizing to the first reverse prime. In an even further aspect, the extension product of the first forward primer is capable of hybridizing to the first reverse primer but will not form a primer dimer. In a still further aspect, the first forward primer comprises the sequence of SEQ ID NO.: 1; and wherein the first reverse primer comprises the sequence of SEQ ID NO.: 2. In a further aspect, the first reverse primer is blocked from priming the first target nucleic acid. In a still further aspect, the first reverse primer is blocked from priming the first target nucleic acid by a terminal 3' mismatched base.

In various aspects, the second target nucleic acid is within a gene of known copy number. In a further aspect, the second target nucleic acid is within a low copy number gene. In a still further aspect, the second target nucleic acid is within a single copy number gene.

In various aspects, the second target nucleic acid is within a gene of known copy number known to rarely undergo copy number variations. In a further aspect, the second target nucleic acid is within a low copy number gene known to rarely undergo copy number variations. In a still further aspect, the second target nucleic acid is within a single copy number gene known to rarely undergo copy number variations.

In a further aspect, the second target nucleic acid is within a single copy number gene, and the single copy gene is β2-microglobulin. In a further aspect, the second forward primer comprises SEQ ID NO.: 3. In a yet further aspect, the second reverse primer comprises SEQ ID NO.: 4. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon.

In a further aspect, the second target nucleic acid is within a single copy number gene, and the single copy gene is PGK. In a further aspect, the second forward primer comprises a sequence complementary to a sequence in the PGK gene, the second reverse primer comprises a sequence complementary to a sequence in the PGK gene, and the second forward primer and second reverse primer yield the second amplicon.

In a further aspect, the second target nucleic acid is within a single copy number gene, and the single copy gene is GAPDH. In a further aspect, the second forward primer comprises a sequence complementary to a sequence in the GAPDH gene, the second reverse primer comprises a sequence complementary to a sequence in the GAPDH gene, and the second forward primer and second reverse primer yield the second amplicon.

In a further aspect, the second target nucleic acid is within a single copy number gene, and the single copy gene is hTERT. In a further aspect, the second forward primer comprises a sequence complementary to a sequence in the hTERT gene, the second reverse primer comprises a sequence complementary to a sequence in the hTERT gene, and the second forward primer and second reverse primer yield the second amplicon.

In a further aspect, the second target nucleic acid is within a single copy number gene, and the single copy gene is ACTB. In a further aspect, the second forward primer comprises a sequence complementary to a sequence in the ACTB gene, the second reverse primer comprises a sequence complementary to a sequence in the ACTB gene, and the second forward primer and second reverse primer yield the second amplicon.

In various aspects, the second target nucleic acid is located within a human gene.

In various aspects, the third target nucleic acid is within a gene of known copy number. In a further aspect, the third target nucleic acid is within a low copy number gene. In a still further aspect, the third target nucleic acid is within a single copy number gene.

In various aspects, the third target nucleic acid is within a gene of known copy number known to rarely undergo copy number variations. In a further aspect, the third target nucleic acid is within a low copy number gene known to rarely undergo copy number variations. In a still further aspect, the third target nucleic acid is within a single copy number gene known to rarely undergo copy number variations.

In a further aspect, the second target nucleic acid is within a single copy number gene, and the single copy gene is β2-microglobulin, and the third target nucleic acid is within a single copy number gene, and the single copy gene is RNase P. In a further aspect, the second forward primer comprises SEQ ID NO.: 3. In a yet further aspect, the second reverse primer comprises SEQ ID NO.: 4. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon. In an even further aspect, third forward primer comprises SEQ ID NO.: 6. In a still further aspect, third reverse primer comprises SEQ ID NO.: 7. In yet further aspect, third forward primer comprises SEQ ID NO.: 9. In an even further aspect, third reverse primer comprises SEQ ID NO.: 10. In a still further aspect, the third forward primer comprises a sequence complementary to a sequence in RNase P, the third reverse primer comprises a sequence complementary to a sequence in RNase P, and the third forward primer and third reverse primer yield the third amplicon. Alternatively, primer and probe sequences target to RNase P, and suitable for use in the disclosed methods, are described by Fan et al. BMC Infectious Disease (2014) 14:541.

In a further aspect, the second target nucleic acid is within a single copy number gene, and the single copy gene is β2-microglobulin, and the third target nucleic acid is within a single copy number gene, and the single copy gene is GAPDH. In a further aspect, the second forward primer comprises SEQ ID NO.: 3. In a yet further aspect, the second reverse primer comprises SEQ ID NO.: 4. In a still further aspect, the third forward primer comprises SEQ ID NO.: 26. In an even further aspect, the third reverse primer comprises SEQ ID NO.: 27. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon. In an even further aspect, the third forward primer comprises a sequence complementary to a sequence in GAPDH, the third reverse primer comprises a sequence complementary to a sequence in GAPDH, and the third forward primer and third reverse primer yield the third amplicon.

In a further aspect, the second target nucleic acid is within a single copy number gene, and the single copy gene is β2-microglobulin, and the third target nucleic acid is within a single copy number gene, and the single copy gene is PGK. In a further aspect, the second forward primer comprises SEQ ID NO.: 3. In a yet further aspect, the second reverse primer comprises SEQ ID NO.: 4. In a still further aspect, the third forward primer comprises SEQ ID NO.: 22. In an even further aspect, the third reverse primer comprises SEQ ID NO.: 23. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon. In an even further aspect, the third forward primer comprises a sequence complementary to a sequence in PGK, the third reverse primer comprises a sequence complementary to a sequence in PGK, and the third forward primer and third reverse primer yield the third amplicon.

In a further aspect, the second target nucleic acid is within a single copy number gene, and the single copy gene is β2-microglobulin, and the third target nucleic acid is within a single copy number gene, and the single copy gene is hTERT. In a further aspect, the second forward primer comprises SEQ ID NO.: 3. In a yet further aspect, the second reverse primer comprises SEQ ID NO.: 4. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon. In an even further aspect, the third forward primer comprises a sequence complementary to a sequence in hTERT, the third reverse primer comprises a sequence complementary to a sequence in hTERT, and the third forward primer and third reverse primer yield the third amplicon.

In a further aspect, the second target nucleic acid is within a single copy number gene, and the single copy gene is β2-microglobulin, and the third target nucleic acid is within a single copy number gene, and the single copy gene is ACTB. In a further aspect, the second forward primer comprises SEQ ID NO.: 3. In a further aspect, the second reverse primer comprises SEQ ID NO.: 4. In a still further aspect, the third forward primer comprises SEQ ID NO.: 24. In an even further aspect, the third reverse primer comprises SEQ ID NO.: 25. In a still further aspect, the second forward primer comprises a sequence complementary to a sequence in the β2-microglobulin gene, the second reverse primer comprises a sequence complementary to a sequence in the β2-microglobulin gene, and the second forward primer and second reverse primer yield the second amplicon. In an even further aspect, the third forward primer comprises a sequence complementary to a sequence in ACTB, the third reverse primer comprises a sequence complementary to a sequence in ACTB, and the third forward primer and third reverse primer yield the third amplicon.

In a further aspect, the second target nucleic acid is within a single copy number gene, and the single copy gene is RNase P, and the third target nucleic acid is within a single copy number gene, and the single copy gene is GAPDH. In a further aspect, second forward primer comprises SEQ ID NO.: 6. In a still further aspect, second reverse primer comprises SEQ ID NO.: 7. In yet further aspect, second forward primer comprises SEQ ID NO.: 9. In an even further aspect, second reverse primer comprises SEQ ID NO.: 10. In a still further aspect, the third forward primer comprises SEQ ID NO.: 26. In an even further aspect, the third reverse primer comprises SEQ ID NO.: 27. In a still further aspect, the second forward primer comprises a sequence complementary to a sequence in RNase P, the second reverse primer comprises a sequence complementary to a sequence in RNase P, and the second forward primer and third reverse primer yield the third amplicon. Alternatively, primer and probe sequences target to RNase P, and suitable for use in the disclosed methods, are described by Fan et al. BMC Infectious Disease (2014) 14:541. In an even further aspect, the third forward primer comprises a sequence complementary to a sequence in GAPDH, the third reverse primer comprises a sequence complementary to a sequence in GAPDH, and the third forward primer and third reverse primer yield the third amplicon.

In a further aspect, the second target nucleic acid is within a single copy number gene, and the single copy gene is RNase P, and the third target nucleic acid is within a single copy number gene, and the single copy gene is PGK. In a further aspect, second forward primer comprises SEQ ID NO.: 6. In a still further aspect, second reverse primer comprises SEQ ID NO.: 7. In yet further aspect, second forward primer comprises SEQ ID NO.: 9. In an even further aspect, second reverse primer comprises SEQ ID NO.: 10. In a still further aspect, the third forward primer comprises SEQ ID NO.: 22. In an even further aspect, the third reverse primer comprises SEQ ID NO.: 23. In a still further aspect, the second forward primer comprises a sequence complementary to a sequence in RNase P, the second reverse primer comprises a sequence complementary to a sequence in RNase P, and the second forward primer and third reverse primer yield the third amplicon. Alternatively, primer and probe sequences target to RNase P, and suitable for use in the disclosed methods, are described by Fan et al. BMC Infectious Disease (2014) 14:541. In an even further aspect, the third forward primer comprises a sequence complementary to a sequence in PGK, the third reverse primer comprises a sequence complementary to a sequence in PGK, and the third forward primer and third reverse primer yield the third amplicon.

In a further aspect, the second target nucleic acid is within a single copy number gene, and the single copy gene is RNase P, and the third target nucleic acid is within a single copy number gene, and the single copy gene is hTERT. In a further aspect, second forward primer comprises SEQ ID NO.: 6. In a still further aspect, second reverse primer comprises SEQ ID NO.: 7. In yet further aspect, second forward primer comprises SEQ ID NO.: 9. In an even further aspect, second reverse primer comprises SEQ ID NO.: 10. In a still further aspect, the second forward primer comprises a sequence complementary to a sequence in RNase P, the second reverse primer comprises a sequence complementary to a sequence in RNase P, and the second forward primer and third reverse primer yield the third amplicon. Alternatively, primer and probe sequences target to RNase P, and suitable for use in the disclosed methods, are described by Fan et al. BMC Infectious Disease (2014) 14:541. In an even further aspect, the third forward primer comprises a sequence complementary to a sequence in hTERT, the third reverse primer comprises a sequence complementary to a sequence in hTERT, and the third forward primer and third reverse primer yield the third amplicon.

In a further aspect, the second target nucleic acid is within a single copy number gene, and the single copy gene is RNase P, and the third target nucleic acid is within a single copy number gene, and the single copy gene is ACTB. In a further aspect, second forward primer comprises SEQ ID NO.: 6. In a still further aspect, second reverse primer comprises SEQ ID NO.: 7. In yet further aspect, second forward primer comprises SEQ ID NO.: 9. In an even further aspect, second reverse primer comprises SEQ ID NO.: 10. In a still further aspect, the third forward primer comprises SEQ ID NO.: 24. In an even further aspect, the third reverse primer comprises SEQ ID NO.: 25. In a still further aspect, the second forward primer comprises a sequence complementary to a sequence in RNase P, the second reverse primer comprises a sequence complementary to a sequence in RNase P, and the second forward primer and third reverse primer yield the third amplicon. Alternatively, primer and probe sequences target to RNase P, and suitable for use in the disclosed methods, are described by Fan et al. BMC Infectious Disease (2014) 14:541. In an even further aspect, the third forward primer comprises a sequence complementary to a sequence in ACTB, the third reverse primer comprises a sequence complementary to a sequence in ACTB, and the third forward primer and third reverse primer yield the third amplicon.

In a further aspect, the second target nucleic acid is within a single copy number gene, and the single copy gene is GAPDH, and the third target nucleic acid is within a single copy number gene, and the single copy gene is PGK. In a still further aspect, the second forward primer comprises SEQ ID NO.: 26. In an even further aspect, the second reverse primer comprises SEQ ID NO.: 27. In a still further aspect, the third forward primer comprises SEQ ID NO.: 22. In an even further aspect, the third reverse primer comprises SEQ ID NO.: 23. In a further aspect, the second forward primer comprises a sequence complementary to a sequence in the GAPDH, the second reverse primer comprises a sequence complementary to a sequence in the GAPDH gene, and the second forward primer and second reverse primer yield the second amplicon. In an even further aspect, the third forward primer comprises a sequence complementary to a sequence in PGK, the third reverse primer comprises a sequence complementary to a sequence in PGK, and the third forward primer and third reverse primer yield the third amplicon.

In a further aspect, the second target nucleic acid is within a single copy number gene, and the single copy gene is GAPDH, and the third target nucleic acid is within a single copy number gene, and the single copy gene is hTERT. In a further aspect, the second forward primer comprises a sequence complementary to a sequence in the GAPDH, the second reverse primer comprises a sequence complementary to a sequence in the GAPDH gene, and the second forward primer and second reverse primer yield the second amplicon. In an even further aspect, the third forward primer comprises a sequence complementary to a sequence in hTERT, the third reverse primer comprises a sequence complementary to a sequence in hTERT, and the third forward primer and third reverse primer yield the third amplicon.

In a further aspect, the second target nucleic acid is within a single copy number gene, and the single copy gene is GAPDH, and the third target nucleic acid is within a single copy number gene, and the single copy gene is ACTB. In a still further aspect, the second forward primer comprises SEQ ID NO.: 26. In an even further aspect, the second reverse primer comprises SEQ ID NO.: 27. In a still further aspect, the third forward primer comprises SEQ ID NO.: 24. In an even further aspect, the third reverse primer comprises SEQ ID NO.: 25. In a further aspect, the second forward primer comprises a sequence complementary to a sequence in the GAPDH, the second reverse primer comprises a sequence complementary to a sequence in the GAPDH gene, and the second forward primer and second reverse primer yield the second amplicon. In an even further aspect, the third forward primer comprises a sequence complementary to a sequence in ACTB, the third reverse primer comprises a sequence complementary to a sequence in ACTB, and the third forward primer and third reverse primer yield the third amplicon.

In a further aspect, the second target nucleic acid is within a single copy number gene, and the single copy gene is PGK, and the third target nucleic acid is within a single copy number gene, and the single copy gene is hTERT. In a still further aspect, the second forward primer comprises SEQ ID NO.: 22. In an even further aspect, the second reverse primer comprises SEQ ID NO.: 23. In a further aspect, the second forward primer comprises a sequence complementary to a sequence in the PGK, the second reverse primer comprises a sequence complementary to a sequence in the PGK gene, and the second forward primer and second reverse primer yield the second amplicon. In an even further aspect, the third forward primer comprises a sequence complementary to a sequence in hTERT, the third reverse primer comprises a sequence complementary to a sequence in hTERT, and the third forward primer and third reverse primer yield the third amplicon.

In a further aspect, the second target nucleic acid is within a single copy number gene, and the single copy gene is PGK, and the third target nucleic acid is within a single copy number gene, and the single copy gene is ACTB. In a still further aspect, the second forward primer comprises SEQ ID NO.: 22. In an even further aspect, the second reverse primer comprises SEQ ID NO.: 23. In a still further aspect, the third forward primer comprises SEQ ID NO.: 24. In an even further aspect, the third reverse primer comprises SEQ ID NO.: 25. In a further aspect, the second forward primer comprises a sequence complementary to a sequence in the PGK, the second reverse primer comprises a sequence complementary to a sequence in the PGK gene, and the second forward primer and second reverse primer yield the second amplicon. In an even further aspect, the third forward primer comprises a sequence complementary to a sequence in ACTB, the third reverse primer comprises a sequence complementary to a sequence in ACTB, and the third forward primer and third reverse primer yield the third amplicon.

In a further aspect, the second target nucleic acid is within a single copy number gene, and the single copy gene is hTERT, and the third target nucleic acid is within a single copy number gene, and the single copy gene is ACTB. In a still further aspect, the third forward primer comprises SEQ ID NO.: 24. In an even further aspect, the third reverse primer comprises SEQ ID NO.: 25. In a further aspect, the second forward primer comprises a sequence complementary to a sequence in the hTERT, the second reverse primer comprises a sequence complementary to a sequence in the hTERT gene, and the second forward primer and second reverse primer yield the second amplicon. In an even further aspect, the third forward primer comprises a sequence complementary to a sequence in ACTB, the third reverse primer comprises a sequence complementary to a sequence in ACTB, and the third forward primer and third reverse primer yield the third amplicon.

In various aspects, the third target nucleic acid is located within a human gene.

In a further aspect, the first detection label, second detection label, and third detection label are detectable individually and simultaneously. In a still further aspect, the first detection label, second detection label, and third detection label are detectable individually and simultaneously, and each of the first detection label, second detection label, and third detection label independently comprise fluorogenic moieties.

In a further aspect, the first detection label, second detection label, third detection label, and fourth detection label are detectable individually and simultaneously. In a still further aspect, the first detection label, second detection label, third detection label, and fourth detection label are detectable individually and simultaneously, and each of the first detection label, second detection label, fourth detection label, and fourth detection label independently comprise fluorogenic moieties.

In a further aspect, the first detection label, second detection label, third detection label, fourth detection label, and fifth detection label are detectable individually and simultaneously. In a still further aspect, the first detection label, second detection label, third detection label, fourth detection label, and fifth detection label are detectable individually and simultaneously, and each of the first detection label, second detection label, fourth detection label, fourth detection label, and fifth detection label independently comprise fluorogenic moieties.

For example, the methods described herein can use fluorescent dyes that preferentially bind to double stranded nucleic acid amplification products during the PCR reaction, thereby providing continuous monitoring of product synthesis (see Higuchi, R. et al., Biotechnology 11: 1026-1030 (1993); Morrison, T. B. et al., Biotechniques 24: 954-962 (1998)).

In a further aspect, the first detection label further comprises a DNA binding dye. In a still further aspect, the fluorogenic DNA-binding dye is 2-methyl-4,6-bis(4-N,N-dimethylaminophenyl)pyrylium iodide, N',N'-dimethyl-N-[4-[(E)-3-methyl-1,3-benzothiazol-2-ylidene)methyl]-1-phenylquinolin-1-ium-2-yl]-N-propylpropane-1,3-diamine, 2-((2-(diethylamino)-1-phenyl-1,8a-dihydroquinolin-4-yl)methyl)-3-methylbenzo[d]thiazol-3-ium iodide, (Z)-4-((3',6-dimethyl-[2,6'-bibenzo[d]thiazol]-2'(3'H)-ylidene)methyl)-1-methylpyridin-1-ium iodide, or (Z)-4-((6-(benzo[d]oxazol-2-yl)-3-methylbenzo[d]thiazol-2(3H)-ylidene)methyl)-1-methylquinolin-1-ium iodide.

In a further aspect, the second detection label further comprises an oligonucleotide, a fluorogenic moiety, and a fluorogenic quenching moiety. In a still further aspect, the second detection label further comprises an oligonucleotide, a fluorogenic moiety linked to the 5' end of the oligonucleotide, and a fluorogenic quenching moiety at the 3' end of the oligonucleotide probe. In a yet further aspect, the second detection label further comprises an oligonucleotide comprising the sequence of SEQ ID NO.: 5. In an even further aspect, the second detection label further comprises an oligonucleotide comprising the sequence of SEQ ID NO.: 8. In a yet further aspect, the second detection label further comprises an oligonucleotide comprising the sequence of SEQ ID NO.: 11. In an even further aspect, the second detection label further comprises a fluorogenic moiety, and the fluorogenic moiety comprises a cyanine dye. In a still further aspect, the cyanine dye is Cy5. In a yet further aspect, the fluorogenic quenching moiety is a dark quencher.

Examples of additional suitable fluorescent labels include, but are not limited to, SYBR Green I (Invitrogen), fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenehoron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC. Fluorescent labels can be obtained from a variety of commercial sources, including Invitrogen, Carlsbad, Calif.; Amersham Pharmacia Biotech, Piscataway, N.J.; Molecular Probes, Eugene, Oreg.; and Research Organics, Cleveland, Ohio.

In a further aspect, the third detection label further comprises an oligonucleotide, a fluorogenic moiety, and a fluorogenic quenching moiety. In a still further aspect, the third detection label further comprises an oligonucleotide, a fluorogenic moiety linked to the 5' end of the oligonucleotide, and a fluorogenic quenching moiety 3' end of the oligonucleotide probe. In a yet further aspect, the third detection label further comprises an oligonucleotide comprising the sequence of SEQ ID NO.: 8. In a still further aspect, the third detection label further comprises an oligonucleotide comprising the sequence of SEQ ID NO.: 11. In an even further aspect, the fluorogenic moiety comprises a VIC. In a yet further aspect, the fluorogenic quenching moiety is a dark quencher. In an even further aspect, the fluorogenic quenching moiety is a dark quencher, and the dark quencher is TAMRA.

In a further aspect, the fourth detection label further comprises an oligonucleotide, a fluorogenic moiety, and a fluorogenic quenching moiety. In a still further aspect, the fourth detection label further comprises an oligonucleotide, a fluorogenic moiety linked to the 5' end of the oligonucleotide, and a fluorogenic quenching moiety 3' end of the oligonucleotide probe.

In a further aspect, the fifth detection label further comprises an oligonucleotide, a fluorogenic moiety, and a fluorogenic quenching moiety. In a still further aspect, the fifth detection label further comprises an oligonucleotide, a fluorogenic moiety linked to the 5' end of the oligonucleotide, and a fluorogenic quenching moiety 3' end of the oligonucleotide probe.

In a further aspect, the second amplicon is at greater than or equal to about 50 bp in length. In a still further aspect, the second amplicon is at less than or equal to about 250 bp in length. In a yet further aspect, the second amplicon is from about 50 to about 60 bp in length. In an even further aspect, the second amplicon is from about 50 to about 70 bp in length. In a still further aspect, the second amplicon is from about 50 to about 80 bp in length. In a yet further aspect, the second amplicon is from about 50 to about 90 bp in length. In an even further aspect, the second amplicon is from about 50 to about 100 bp in length. In a still further aspect, the second amplicon is from about 50 to about 125 bp in length. In a yet further aspect, the second amplicon is from about 50 to about 150 bp in length. In an even further aspect, the second amplicon is from about 50 to about 175 bp in length. In a still further aspect, the second amplicon is from about 50 to about 200 bp in length. In a yet further aspect, the second amplicon is from about 50 to about 250 bp in length.

In a further aspect, the third amplicon is at greater than or equal to about 50 bp in length. In a still further aspect, the third amplicon is at less than or equal to about 250 bp in length. In a yet further aspect, the third amplicon is from about 50 to about 60 bp in length. In an even further aspect, the third amplicon is from about 50 to about 70 bp in length. In a still further aspect, the third amplicon is from about 50 to about 80 bp in length. In a yet further aspect, the third amplicon is from about 50 to about 90 bp in length. In an even further aspect, the third amplicon is from about 50 to about 100 bp in length. In a still further aspect, the third amplicon is from about 50 to about 125 bp in length. In a yet further aspect, the third amplicon is from about 50 to about 150 bp in length. In an even further aspect, the third amplicon is from about 50 to about 175 bp in length. In a still further aspect, the third amplicon is from about 50 to about 200 bp in length. In a yet further aspect, the third amplicon is from about 50 to about 250 bp in length.

In various aspects, the concentration of first, second, and third amplicon are determined by comparison to a control target DNA.

In a further aspect, the concentration of first, second, and third amplicon are determined by comparison to a control target DNA, wherein the control target DNA is a control synthetic target DNA. In a still further aspect, the control synthetic target DNA comprises $(TTAGGG)_m$, wherein m is an integer from 15 to 34. In a yet further aspect, the control synthetic target DNA comprises $(CCCTAA)_m$, wherein m is an integer from 15 to 34. In an even further aspect, the control synthetic target DNA is SEQ ID NO.: 12.

In a further aspect, the control synthetic target DNA is at least 90 base pairs in length. In a still further aspect, the control synthetic target DNA is at least 100 base pairs in length. In a yet further aspect, the control synthetic target DNA is at least 110 base pairs in length. In an even further aspect, the control synthetic target DNA is at least 120 base pairs in length. In a still further aspect, the control synthetic target DNA is at least 130 base pairs in length. In a yet further aspect, the control synthetic target DNA is at least 140 base pairs in length. In an even further aspect, the control synthetic target DNA is at least 150 base pairs in length. In a still further aspect, the control synthetic target DNA is at least 160 base pairs in length. In a yet further aspect, the control synthetic target DNA is at least 170 base pairs in length. In an even further aspect, the control synthetic target DNA is at least 180 base pairs in length.

In a further aspect, the control synthetic target DNA is from about 90 base pairs to about 200 base pairs in length. In a yet further aspect, the control synthetic target DNA is SEQ ID NO.: 12. In a still further aspect, the control synthetic target DNA is from about 100 base pairs to about 200 base pairs in length. In a yet further aspect, the control synthetic target DNA is from about 110 base pairs to about 200 base pairs in length. In an even further aspect, the control synthetic target DNA is from about 120 base pairs to about 200 base pairs in length. In a still further aspect, the control synthetic target DNA is from about 130 base pairs to about 200 base pairs in length. In a yet further aspect, the control synthetic target DNA is from about 140 base pairs to about 200 base pairs in length. In an even further aspect, the control synthetic target DNA is from about 150 base pairs to about 200 base pairs in length. In an even further aspect, the control synthetic target DNA is from about 175 base pairs to about 200 base pairs in length.

In an even further aspect, the control synthetic target DNA is from about 90 base pairs to about 150 base pairs in length. In a still further aspect, the control synthetic target DNA is from about 90 base pairs to about 125 base pairs in length. In a yet further aspect, the control synthetic target DNA is from about 90 base pairs to about 110 base pairs in length. In an even further aspect, the control synthetic target DNA is from about 90 base pairs to about 175 base pairs in length.

In a further aspect, the concentration of first, second, and third amplicon are determined by comparison to a control target DNA, wherein is human genomic DNA. In a yet further aspect, the human genomic DNA comprises DNA obtained from male or female donors. In an even further aspect, the human genomic DNA is a mosaic composition of male and female donors together, or a mosaic composition of male only or female only donors.

Amplification reactions are carried out according to procedures well known in the art. Procedures for PCR are widely used and described (see for example, U.S. Pat. Nos. 4,683,195 and 4,683,202). In brief, a double stranded target nucleic acid is denatured, generally by incubating at a temperature high enough to denature the strands, and then incubated in the presence of excess primers, which hybridize (anneal) to the single-stranded target nucleic acids. A DNA polymerase extends the hybridized primer, generating a new copy of the target nucleic acid. The resulting duplex is denatured and the hybridization and extension steps are repeated. By reiterating the steps of denaturation, annealing, and extension in the presence of a second primer for the complementary target strand, the target nucleic acid encompassed by the two primers is exponentially amplified. The time and temperature of the primer extension step will depend on the polymerase, length and sequence composition of the target nucleic acid being amplified, and primer sequence employed for the amplification. The number of reiterative steps required to sufficiently amplify the target nucleic acid will depend on the efficiency of the amplification. One skilled in the art will understand that the present disclosure is not limited by variations in times, temperatures, buffer conditions, and amplification cycles applied in the amplification process.

A denaturation step is typically the first step in the repeating cycle of the PCR and consists of heating the reaction to a denaturation temperature of 90-98° C., e.g. 91, 92, 93, 94, 95, 96, 97, or 98° C. for 1-35 seconds, preferably 15 16, 17, 18, 19, 20, 21, 22, 23, 24, 25, 26, 27, 28, 29, 30, 31, 32, 33, 34, or 35 seconds. The denaturation step melts the DNA template by disrupting the hydrogen bonds between complementary bases, yielding single strands of DNA.

An annealing step is typically the second step in the repeating cycle of the PCR and consists of lowering the temperature to an annealing temperature of 45, 46, 47, 48, 49, 50, 51, 52, 53, 54, 55, 56, 57, 58, 59, 60, 61, 62, 63, 64, 65, 66, 67, 68, 69, or 70° C. for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 seconds allowing annealing of the primers in a primer set to hybridize with a target nucleic acid. The annealing temperature can be about 0, 1, 2, 3, 4, 5, 6, 7, 8, 9, or 10 or up to 15° C. below the melting temperature of the duplex Tm for the primers used. Stable DNA-DNA hydrogen bonds are formed when the primer sequence very closely matches or is identical at the 3' end of the primer to a portion of the complement to the template sequence. The polymerase binds to the primer-template hybrid and begins DNA synthesis.

The extension/elongation step is the step where the nucleic acid polymerase synthesizes a new nucleic acid strand complementary to the target nucleic acid strand by adding dNTPs that are complementary to the target nucleic acid in 5' to 3' direction, condensing the 5'-phosphate group of the dNTPs with the 3'-hydroxyl group at the end of the nascent (extending) target nucleic acid strand. The extension time depends both on the nucleic acid polymerase used and on the length of the target nucleic acid to be amplified. As a rule-of-thumb, at its optimum temperature, the nucleic acid polymerase will polymerize up to a thousand bases per minute. Under optimum conditions, i.e., if there are no limitations due to limiting substrates or reagents, at each extension step, the amount of target nucleic acid is doubled, leading to exponential (geometric) amplification of the specific target nucleic acid. The elongation temperature at this step depends on the nucleic acid polymerase used. For example; Taq polymerase has its optimum activity temperature at 75-80° C., and commonly a temperature of 72° C. is used with this enzyme PCR can also comprise a final elongation step. The final elongation can be performed at a final elongation temperature of 68, 69, 70, 71, 72, 73, 74 or 75° C. for 1, 2, 3, 4, 5, 6, 7, 8, 9, 10, 11, 12, 13, 14, or 15 minutes after the last PCR cycle to ensure that any remaining single-stranded DNA is fully copied to make a double-stranded DNA product.

PCR can also comprise a signal acquisition step wherein the amount of a detection label can be determined. The signal acquisition step can be carried out during the amplification of the target sequence. In some aspects the signal acquisition step follows a denaturation step, an annealing step and an elongation steps. The signal acquisition step is carried out at a signal acquisition temperature. The signal acquisition temperature can be any temperature and can be carried out at one or more times during PCR. When the copy number of two or more target nucleic acids are being determined as described herein, the signal acquisition temperature should be different for detection of the detection label of each amplicon. For example, the temperatures for the two or more signal acquisition temperature should be selected such that the first signal acquisition temperature is below the Tm of the first amplicon and the second signal acquisition temperature is above said first Tm and below the Tm of the second amplicon. The difference between the two or more signal acquisition temperatures can be 3, 4, 5, 6, 7, 8, 9, or 10° C. A Signal Acquisition Step can be carried out for 1, 2, 3, 4, 5, 6, 7, 8, 9, 10, 11, 12, 13, 14, or 15 seconds at the acquisition temperature.

PCR can also comprise a final hold step. The final hold step can be at a final hold temperature of about 4, 5, 6, 7, 8, 9, 10, 11, 12, 13, 14, or 15° C. for an indefinite time. The final hold step can be employed for short-term storage of the reaction.

The polymerase chain reaction can also comprise consecutive stages of cycles. Each consecutive stage of cycles can comprise one or more of the PCR steps described above. Each consecutive stage of cycles can also be referred to a "cycle" of the PCR. Each consecutive stage of cycles can be carried out under the same or different temperatures for each cycle of the PCR. A PCR can be run where the annealing temperature is changed for one or more of the cycles of PCR. For example, the PCR can be run for a total of 40 cycles, wherein the annealing temperature is the same for a first stage of cycles, then the annealing temperature is raised for a second stage of cycles and the annealing temperature is lowered for the third stage of cycles.

The methods described herein allow for the quantitation of multiple amplicons in one or more amplification cycle by a discrete signal for each amplicon, i.e., multiplex signal detection. In various aspects, collecting signals from multiple amplicons in each cycle consists of using multiple fluorophores which are detected at different wave-lengths by the optical system of the PCR instrument. In a further aspects, the disclosed methods utilize a double-stranded DNA binding or intercalating dye, e.g., ethidium bromide, SYBR® Green, or EvaGreen® dye, and probes for the second and third amplicons (and fourth, fifth, etc., if more than three amplicons are to be amplified). The probes are oligonucleotides with a reporter dye covalently linked to one terminus of the oligonucleotide, and a quencher dye covalently linked to the other terminus of the oligonucleotide. In various aspects, the probe is an oligonucleotide with a reporter dye attached to the 5' end and a quencher dye attached to the 3' end. In a further aspect, all amplicons in the reaction can generate a signal with the DNA binding or intercalating dye, therefore the first amplicon should reach cycle threshold at least five amplification cycles before the second and third (and fourth, fifth, etc., if more than three amplicons are to be amplified) amplicons reach cycle threshold.

The methods described herein can also be carried out using other approaches for the quantitation of multiple amplicons in each amplification cycle by a discrete signal for each amplicon. In a further aspect, a third primer for each amplicon can be linked to a quenching dye, and the quenching agent is cleaved by the polymerase in the reaction during the extension reaction (i.e., a q-PCR probe). In a still further aspect, a fluorophore can be linked to an oligo that hybridizes to the amplicon and is not quenched when hybridized to the DNA strand (i.e., a molecular beacon), and a different molecular beacon can be used for each amplicon. In a yet further aspect, the polymerase chain reaction can comprise a DNA binding or intercalating fluorescent dyes. The signal for DNA binding or intercalating dye is collected at the end of the extension cycle when all amplicons are double-stranded.

In various aspects, the methods described herein present a strategy that allows the signals from multiple amplicons to be collected separately. In a further aspect, the cycle thresholds (Cts) for the first amplicon are collected at earlier cycles, when the signal from the second and third amplicons are still at baseline. The Cts for the second and third amplicons (and fourth, fifth, etc. amplicons if more than three amplicons are amplified together) are collected at a temperature well above the melting temperature (Tm) of the first amplicon, rendering the first amplicon single-stranded and sending its signal to baseline. Primers are designed to make both amplicons small, and the second and third amplicons can be GC-rich, raising its Tm. Pairs of templates that occur in biological samples as high and low abundance species with no overlap in copy number ranges are natural targets for such an approach The products of the amplification are detected and analyzed by methods well known in the art. Amplified products may be analyzed following separation and/or purification of the products, or by direct measurement of product formed in the amplification reaction. For detection, the product may be identified indirectly with fluorescent compounds, e.g., ethidium bromide, SYBR® Green, or EvaGreen®, or by hybridization with labeled nucleic acid probes. Alternatively, labeled primers or labeled nucleotides are used in the amplification reaction to label the amplification product. The label comprises any detectable moiety, including fluorescent labels, radioactive labels, electronic labels, and indirect labels such as biotin or digoxigenin.

Instrumentation suitable for conducting the qPCR reactions of the present disclosure are available from a number of commercial sources (ABI Prism 7700, Applied Biosystems, Carlsbad, Calif.; LIGHTCYCLER 480, Roche Applied Science, Indianapolis, Ind.; Eco Real-Time PCR System, Illumina, Inc., San Diego, Calif.; RoboCycler 40, Stratagene, Cedar Creek, Tex.).

When real time quantitative PCR is used to detect and measure the amplification products, various algorithms are used to calculate the number of target telomeres in the samples. (For example, see ABI Prism 7700 Software Version 1.7; Lightcycler Software Version 3). Quantitation may involve use of standard samples with known copy number of the telomere nucleic acids and generation of standard curves from the logarithms of the standards and the cycle of threshold ($C_t$). In general, $C_t$ is the PCR cycle or fractional PCR cycle where the fluorescence generated by the amplification product is several deviations above the baseline fluorescence.

2. Target Samples

Target samples can be derived from any source that has, or is suspected of having, target molecules. Target samples can contain, for example, a target molecule(s) such as nucleic acids. A target sample can be the source of target nucleic acids. A target sample can include natural target nucleic acids, chemically synthesized target nucleic acids, or both. A target sample can be, for example, a sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Types of useful target samples include blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, forensic samples, archeological samples, infection samples, nosocomial infection samples, production samples, drug preparation samples, biological molecule production samples, protein preparation samples, lipid preparation samples, and/or carbohydrate preparation samples.

3. Target Nucleic Acids

Nucleic acid samples can be derived from any source that has, or is suspected of having, target nucleic acids. A nucleic acid sample is the source of nucleic acid molecules and nucleic acid sequences such as target nucleic acids. The nucleic acid sample can contain RNA or DNA or both. The target nucleic acid can also be cDNA. In addition, mRNA can be reverse transcribed to form cDNA which can then serve as a target nucleic acid for use in the methods described herein. For example, chromosomal DNA in its native, double-stranded state, can be obtained from a target sample as described herein above. The chromosomal DNA can be obtained using any DNA purification method which yields high molecular weight genomic DNA (greater than 20 kb) including phenol/chloroform extraction, cesium chloride gradient, and commercial kits that use silicone membrane binding technology, selective detergent-mediated DNA precipitation method. Examples of DNA purification commercial kits include Agencourt DNAdvance and Agencourt Genfind (Beckman Coulter), QIAamp kit (QIAGEN, Valencia, Calif.), QIAamp blood kit (QIAGEN), QIAamp FFPE tissue kit QIAGEN), AHPrep kit (QIAGEN), Puregene kit (QIAGEN), PureLink and GeneCatcher (Invitrogen) and Wizard (Promega).

A "target nucleic acid" or "target sequence" is meant a nucleic acid sequence on a double or single stranded nucleic acid. By "nucleic acid" or "oligonucleotide" or grammatical equivalents herein is meant at least two nucleotides covalently linked together. A nucleic acid of the present invention will generally contain phosphodiester bonds, although in some cases, nucleic acid analogs are included that may have alternate backbones, comprising, for example, phosphoramide (Beaucage, S. L. et al., Tetrahedron 49: 1925-63 (1993), and references therein; Letsinger, R. L. et al., J. Org. Chem. 35: 3800-03 (1970); Sprinzl, M. et al., Eur. J. Biochem. 81: 579-89 (1977); Letsinger, R. L. et al., Nucleic Acids Res. 14:3487-99 (1986); Sawai et al, Chem. Lett. 805 (1984); Letsinger, R. L. et al., J. Am. Chem. Soc. 110: 4470 (1988); and Pauwels et al., Chemica Scripta 26:141-49 (1986)), phosphorothioate (Mag, M. et al., Nucleic Acids Res. 19:1437-41 (1991); and U.S. Pat. No. 5,644,048), phosphorodithioate (Briu et al., J. Am. Chem. Soc. 111:2321 (1989)), O-methylphophoroamidite linkages (see Eckstein, Oligonucleotides and Analogues: A Practical Approach, Oxford University Press, 1991), and peptide nucleic acid backbones and linkages (Egholm, M., Am. Chem. Soc. 114:1895-97 (1992); Meier et al., Chem. Int. Ed. Engl. 31:1008 (1992); Egholm, M., Nature 365: 566-68 (1993); Carlsson, C. et al., Nature 380: 207 (1996), all of which are incorporated by reference). Other analog nucleic acids include those with positive backbones (Dempcy, R. O. et al., Proc. Natl. Acad. Sci. USA 92:6097-101 (1995)); non-ionic backbones (U.S. Pat. Nos. 5,386,023; 5,637,684; 5,602,240; 5,216,141; and 4,469,863; Kiedrowshi et al., Angew. Chem. Intl. Ed. English 30:423 (1991); Letsinger, R. L. et al., J. Am. Chem. Soc. 110: 4470 (1988); Letsinger, R. L. et al., Nucleoside & Nucleotide 13: 1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4: 395 (1994); Jeffs et al., J. Biomolecular NMR 34:17 (1994)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. 169-176 (1995)); all references are hereby expressly incorporated by reference.

Any nucleic acid sequence sought to be measured, identified, detected or whose copy number is sought to be determined can serve as a target nucleic acid sequence. In the methods described herein, there can be more than one target nucleic acid sequence. In the event that two target nucleic acid sequences are present, they will be referred to as a first and second target nucleic acid sequence, respectfully. In the event that three target nucleic acid sequences are present, they will be referred to as a first, a second and a third target nucleic acid sequence, respectfully and so on. The target nucleic acids described in the methods herein can have the same, similar or different copy numbers. For example, the first target nucleic acid is a nucleic acid sequence of multiple copy numbers and the second target nucleic acid is a single copy gene. For example, the first target nucleic acid can be telomeric repeat sequences, mtDNA, rDNA or Alu repeat DNA. For example, the first target nucleic acid can be cDNA reverse-transcribed from a high copy number mRNA, and the second target nucleic acid can be cDNA reverse-transcribed from a low copy number mRNA.

Single copy genes are genes that have a single copy per haploid genome. Single copy genes therefore have two copies per cell. Single copy genes include, but are not limited to, the RNase P gene, the β2-microglobulin gene, the albumin gene, the glyceraldehyde 3-phosphate dehydrogenase (GAPDH) gene, the human telomerase reverse transcriptase, β-actin (ACTB) gene, and the β-globin gene.

Telomeres are specialized structures found at the ends of linear chromosomes of eukaryotes. Telomeres are generally composed of short tandem repeats, with a repeat sequence unit specified by the telomerase enzyme particular to that organism. Telomere repeat sequences are known for a variety of organisms. For vertebrates, plants, certain types of molds, and some protozoans, the sequences are perfect repeats. For example, in humans the sequence, TTAGGG (SEQ ID NO.: 13), occurs as a sequence repeat unit, (TTAGGG)n, where n can be in the range of 1-1000 or more. In other organisms, the repeat sequences are irregular, such as those of *Saccharomyces cerevisiae* where the sequence is variable G1-3T/C1-3A. In some eukaryotic organisms, telomeres lack the short tandem sequence repeats but have sequence elements that function as telomeres. For example, in the fruit fly *Drosophila melanogaster*, the telomere is a composite of retrotransposon elements HeT-A and TART while in the mosquito *Anopheles gambiae* the telomeres are arrays of complex sequence tandem repeats. For the purposes of the present invention, telomeres of different structures are encompassed within the scope of the present invention.

In addition to the repeat sequences, the 3' end of some telomeres contains a single stranded region, which for humans is located on the G rich strand. The single strand is composed of (TTAGGG)n repeats, with n being about 50, although it can be significantly less than or more than 50. As used herein, the length of the 3' single stranded region can also be correlated with mortality or disease risk.

Typically, the DNA replicative machinery acts in the 5' to 3' direction, and synthesis of the lagging strand occurs discontinuously by use of short RNA primers that are degraded following strand synthesis. Since sequences at the 3' end of a linear DNA are not available to complete synthesis of the region previously occupied by the RNA primer, the terminal 3' region of the linear chromosome is not replicated. This "end replication problem" is solved by the action of telomerase, a telomere specific ribonucleoprotein reverse transcriptase. The telomerase enzyme has an integral RNA component that acts as a template for extending the 3' end of the telomere. Repeated extensions by telomerase activity results in the generation of telomere repeats copied from the telomerase-bound RNA template. Following elongation by telomerase, lagging strand synthesis by DNA polymerase completes formation of the double stranded telomeric structure.

In normal human somatic cells, telomerase is not expressed or expressed at low levels. Consequently, telomeres shorten by about 50-200 bp with each cell division until the cells reach replicative senescence, at which point the cells lose the capacity to proliferate. This limited capacity of cells to replicate is generally referred to as the Hayflick limit, and may provide cells with a counting mechanism, i.e., a mitotic clock, to count cell divisions and regulate cellular development. Correspondingly, activation of telomerase in cells lacking telomerase activity, for example by expressing telomerase from a constitute retroviral promoter or activation of endogenous polymerase, allows the cells to maintain proliferative capacity and leads to immortalization of the cell.

Interestingly, cells with very short telomeres often become extended. This phenomenon suggests that the telomerase enzyme protects short telomeres from further shortening while extending those that have fallen below a certain threshold length. Thus, presence of telomerase activity does not appear to be necessary when telomeres are a certain length, but becomes critical to maintenance of telomere integrity when the length falls below a critical limit.

In the methods described herein, the abundance or average length of a telomere may be determined for a single chromosome in a cell. In an aspect, the average copy number of a telomere or mean telomere copy number is measured for a single cell. In another embodiment, the average copy number of a telomere or mean telomere copy number is measured for a population of cells. A change in telomere copy number is an increase or decrease in telomere copy number, in particular an increase or decrease in the average telomere copy number. The change may be relative to a particular time point, i.e., telomere copy number of an organism at time, t1, as compared to telomere length at some later time (t2). A change or difference in telomere copy number may also be compared as against the average or mean telomere copy number of a particular cell population or organism population. In some aspects, a change or difference in telomere copy number may also be compared as against the average or mean telomere copy number of a population not suffering from a disease condition. In certain embodiments, change in telomere copy number is measured against a population existing at different time periods.

Although, telomere copy number may be determined for all eukaryotes, in a one aspect, telomere copy numbers are determined for vertebrates, including without limitation, amphibians, birds, and mammals, for example rodents, ungulates, and primates, particularly humans. Telomere copy numbers can also be determined for organisms in which longevity is a desirable trait or where longevity and susceptibility to disease are correlated with telomere length. In another aspect, the telomeres may be measured for cloned organisms in order to assess the probability of short or long term mortality risk, or disease susceptibility associated with altered telomere integrity in these organisms.

Telomeric nucleic acid sequences, such as those described above can serve as a target sequence. Telomeric nucleic acid sequences, or any other repetitive or non-repetitive target nucleic acid, may be any length, with the understanding that longer sequences can be more specific. In some embodiments, it may be desirable to fragment or cleave the sample nucleic acid into fragments of 100-10,000 base pairs. In one aspect, fragments of roughly 500 bp can be used. Fragmentation or cleavage may be done in any number of ways well known to those skilled in the art, including mechanical, chemical, and enzymatic methods. Thus, the nucleic acids may be subjected to sonication, French press, shearing, or treated with nucleases (e.g., DNase, restriction enzymes, RNase etc.), or chemical cleavage agents (e.g., acid/piperidine, hydrazine/piperidine, iron-EDTA complexes, 1,10-phenanthroline-copper complexes, etc.). Fragmentation of DNA may reduce secondary structure formation which may impede accurate measurement of the target sequence length or abundance.

In various aspects, the disclosed methods further comprise the step of obtaining a chromosomal DNA sample prior to contacting the first, second, and third target nucleic acids with the first, second, and third primer sets, respectively; and wherein the chromosomal DNA sample contains or comprises at least portions of the first, second, and third target nucleic acids. In a further aspect, the chromosomal DNA is obtained from a solid, fluid, semisolid or gaseous sample. In a still further aspect, the chromosomal DNA is obtained from a liquid sample; and wherein the liquid sample is from blood, saliva, urine, plasma, serum, cerebrospinal fluid ("CSF") sputum, or bronchial lavage fluid. In a yet further aspect, the liquid sample is from blood, serum, or plasma. In an even further aspect, the chromosomal DNA is obtained from a solid sample; and wherein the solid sample is from tissue sample. In a still further aspect, the tissue sample is a tissue biopsy. In a yet further aspect, the tissue biopsy is from lung, muscle, or skin. In an even further aspect, the chromosomal DNA is obtained from bone marrow. In a still further aspect, the chromosomal DNA is obtained from a vertebrate. In a yet further aspect, the vertebrate is a mammal. In an even further aspect, the mammal is a primate. In a still further aspect, the primate is human. In other aspects, the chromosomal DNA can be from non-vertebrate animals, for example plants.

In various aspects, the disclosed methods further comprise the step of obtaining a chromosomal DNA sample prior to contacting the first, second, and third target nucleic acids with the first, second, and third primer sets, respectively; and wherein the chromosomal DNA sample comprises the first, second, and third target nucleic acids.

In a further aspect, the disclosed methods further comprise the step of obtaining a chromosomal DNA sample from blood, saliva, urine, plasma, serum, cerebrospinal fluid ("CSF") sputum or bronchial lavage fluid prior to contacting the first, second, and third target nucleic acids with the first, second, and third primer sets, respectively; and wherein the chromosomal DNA sample comprises the first, second, and third target nucleic acids; and wherein the chromosomal DNA is obtained.

In a further aspect, the disclosed methods further comprise the step of obtaining a chromosomal DNA sample from one or more cell types isolated from blood, saliva, urine, plasma, serum, cerebrospinal fluid ("CSF") sputum or bronchial lavage fluid prior to contacting the first, second, and third target nucleic acids with the first, second, and third primer sets, respectively; wherein the chromosomal DNA sample comprises the first, second, and third target nucleic acids; and wherein the chromosomal DNA is obtained; and wherein the cell types isolated comprise circulating tumor cells, circulating stem cells, lymphocytes, granulocytes, myeloid cells, neutrophils, monocytes, macrophages, and leukocytes.

In a further aspect, the disclosed methods further comprise the step of isolating a circulating DNA fragment sample from the blood prior to contacting the first, second, and third target nucleic acids with the first, second, and third primer sets, respectively; and wherein the circulating DNA fragment sample comprises the first, second, and third target nucleic acids;

The telomere products of the disclosed methods can be generated from a single telomere, a single chromosome, a population of chromosomes from a single cell or a population of chromosomes from a plurality of cells.

4. Polymerases

In the methods described herein, an amplification enzyme is required. For example, following contacting the primers to the target nucleic acids, the reaction can be treated with an amplification enzyme. Amplification enzymes are generally polymerases, such as DNA polymerases. A variety of suitable polymerases are well known in the art, including, but not limited to, Taq DNA polymerase, KlenTaq, Tfl polymerase, DynaZyme, etc. Generally, all polymerases are applicable to the present invention. In one aspect, polymerases are thermostable polymerases lacking 3' to 5' exonuclease activity, or polymerases engineered to have reduced or non-functional 3' to 5' exonuclease activities (e.g., Pfu(exo-), Vent(exo-), Pyra(exo-), etc.), since use of polymerases with strong 3' to 5' exonuclease activity tends to remove the mismatched 3' terminal nucleotides that are needed in some applications to prevent or delay primer dimer amplifications, and in other applications to carry out allele-specific amplifications. Also applicable are mixtures of polymerases used to optimally extend hybridized primers. In another aspect, polymerase enzymes useful for the present invention are formulated to become active only at temperatures suitable for amplification.

Presence of polymerase inhibiting antibodies, which become inactivated at amplification temperatures, or sequestering the enzymes in a form rendering it unavailable until amplification temperatures are reached, are all suitable. These polymerase formulations allow mixing all components in a single reaction vessel while preventing priming of non-target nucleic acid sequences.

In addition, those skilled in the art will appreciate that various agents may be added to the reaction to increase processivity of the polymerase, stabilize the polymerase from inactivation, decrease non-specific hybridization of the primers, or increase efficiency of replication. Such additives include, but are not limited to, dimethyl sulfoxide, formamide, acetamide, glycerol, polyethylene glycol, or proteinacious agents such as *E. coli*. single stranded DNA binding protein, T4 gene 32 protein, bovine serum albumin, gelatin, etc. In another aspect, the person skilled in the art can use various nucleotide analogs for amplification of particular types of sequences, for example GC rich or repeating sequences. These analogs include, among others, c7-dGTP, hydroxymethyl-dUTP, dITP, 7-deaza-dGTP, etc.

5. Primers

In some aspects, a primer can be designed to block the primer from priming extension of the target nucleic acid in all but one configuration. For example, one of the primers in a primer set can be designed to block the primer from priming the extension of the target nucleic acid by creating a mismatched base at the 3' end of the primer. By designing and utilizing such a primer, the primer is still able to hybridize to its complementary sequence; however, it will only prime DNA synthesis in a single confirmation, thus giving predictability to the amplicon size and therefore predictability to the Tm of the amplicon.

For example, disclosed herein are primers and primer sets, wherein one primer of the first primer set comprises at least one nucleotide adjacent to the 3' end of the primer, wherein said nucleotide is mismatched against, not complementary to, the target nucleic acid, but complementary to the 3' terminal nucleotide of the other primer in the primer set.

Also disclosed herein are primers and primer sets, wherein one primer of a primer set comprises at least one nucleotide adjacent to the 3' end of the primer, wherein said nucleotide is mismatched against, not complementary to, the target nucleic acid, but complementary to the 3' terminal nucleotide of the other primer in the primer set, wherein the extension product of the mismatch-containing primer of the primer set can be hybridized by the other primer in the primer set, allowing said other primer to prime DNA synthesis along said extension product. In some aspects, the methodology can be used to assess telomere length or abundance on a particular strand of the duplex DNA (e.g., the "C" strand or the "G" strand of the chromosome).

To ensure that a blocked primer will only prime in a single, specific configuration, a primer set including the blocked primer can be designed such that the primers of the primer set overlap with perfect complementarity over the region of the mismatched base present in the blocked primer. Such a design can be performed so as to prevent primer dimer formation and to minimize the ability of the two primers to prime each other. Such a design can be utilized when the target nucleic acid sequence is a sequence comprising multiple repeats such as the repeats found in a telomere (telomeric sequence). An example of such a method is described elsewhere herein, including the Examples below.

As described herein, the primers for direct amplification of telomere repeats can comprise a first primer which hybridizes to a first single strand of the target nucleic acid and a second primer which hybridizes to a second single strand of the target nucleic acid, where the first and second strands are substantially complementary. The primers are capable of primer extension by polymerase when hybridized to their respective strands. That is, the primers hybridized to the target nucleic acid have their 3' terminal nucleotide residues complementary to the nucleotide residue on the target nucleic acid such that the primers are extendable by polymerase. Selected primers are complementary to repetitive units of the repetitive region. For example, at least one nucleotide residue of at least one of the primers can be altered to produce mismatches with a nucleotide residue of at least one repetitive unit to which the primer hybridizes, wherein the altered nucleotide residue also produces a mismatch with the 3' terminal nucleotide residue of the other primer when the primers hybridize to each other. The inclusion of a mismatch prevents or limits primer extension and primer-primer hybrids (primer dimers).

A primer set for direct amplification of telomere repeats can comprise a primer set wherein at least one nucleotide residue of the first primer is altered to produce a mismatch between the altered residue and a nucleotide residue of at least one repetitive unit of the first strand to which the primer hybridizes, wherein the altered nucleotide residue also produces a mismatch with the 3' terminal nucleotide residue of the second primer when the first and second primers hybridize to each other. The altered nucleotide residue can be one or more nucleotide residues from the 3' terminal nucleotide to allow efficient extension by polymerase when the altered primer hybridizes to target nucleic acids. For example, the altered nucleotide residue can be at least 1 nucleotide residue, at least 2 nucleotide residues, or at least 3 nucleotide residues from the 3' terminal nucleotide to allow efficient extension by polymerase when the altered primer hybridizes to target nucleic acids.

As discussed elsewhere herein, the primers of the primer sets can be designed to have similar melting temperatures ("Tms") to limit generation of undesirable amplification products and to permit amplification and detection of several target nucleic acids in a single reaction volume. In addition, since the telomeres of various organisms have differing repetitive unit sequences, amplifying telomeres of a specific organism will employ primers specific to the repetitive unit of each different organism. Human telomeric sequences are used herein to illustrate practice of the present invention for direct amplification and quantitation of tandemly repeated nucleic acid sequences, but the invention is not limited to the disclosed specific embodiment.

Also disclosed are primers to increase the melting temperature (Tm) of the resultant amplicon above that of the other amplicon of the methods described herein. These primers can be referred to as primers comprising a "GC-clamp". "GC-clamps" typically refers to the presence of G or C bases within the last five bases from the 3' end of primers that helps promote specific binding at the 3' end due to the stronger bonding of G and C bases. Typically, more than 3 G's or C's should be avoided in the last 5 bases at the 3' end of the primer. However, in the methods described herein primers comprising a "GC-clamp" are primers that comprise a 5' tag sequence (GC-clamp) that confers a higher melting temperature on the resulting PCR product (amplicon) than the melting temperature without the GC-clamp. The 5' tag sequence of primers comprising a "GC-clamp" comprise a GC-clamp on the 5' end of the primer sequence that is not complementary to any part of the target nucleic acid sequence. A "GC-clamp" is a series of G and C nucleotides that can be linked to the 5' end of a primer in order to increase the melting temperature of the amplicon. A GC-clamp can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more nucleotides long. A GC-clamp can also be referred to a GC-rich region or GC-rich tag.

GC-clamps can be used in the methods described herein to increase the Tm of one of the amplicons. By increasing the Tm of the amplicon, a fluorescent signal can be acquired at a temperature high enough to completely melt the other amplicon, thus allowing for the acquisition of a fluorescent signal for two or more different amplicons at two or more different temperatures. GC-clamped primers can be designed for use in the same amplification reaction such that the GC-clamps on different primers are different from one another so as to prevent hairpin formation or primer dimers that could result in a cessation of the amplification reaction.

Since primers hybridized to target nucleic acids must be capable of primer extension, alterations of the first and second primers must be on non-complementary nucleotides of the repetitive unit. Thus, in one aspect, when both the first and second primers comprise altered residues, the alterations are at nucleotide positions adjacent to the repetitive unit. In another aspect, the alterations are situated on nucleotide positions non-adjacent to the repetitive unit. In general, mismatches at adjacent nucleotide positions provide for the greatest number of base paired or complementary residues between the altered nucleotide and the 3' terminal nucleotide, which may be important for efficiently amplifying short repetitive sequences (i.e., 3-6 bp repeat).

Primers can be designed to be substantially complementary to the repeats. In some aspects, the first primer can contain three repeats complementary to the repetitive target sequence and multiple mismatches can be accordingly introduced into the first primer. In a further aspect, the second primer is can also be designed to contain mismatches with respect to the repeat sequence, but it is designed such that there no mismatches to the first several nucleotides (e.g., 5-7 nucleotides) of the first primer. Thus, an amplicon of defined length can be amplified using the above-described first and second primers. Accordingly, the amplicon produced will be the sum of the length of primer 1 plus primer 2 minus the overlap between the 2 primers. This strategy eliminates the multiple amplicon lengths that were generated in the original design (Cawthon R. M. (2002). Nucleic Acids Res. 30, e47. doi:10.1093/nar/30.10.e47), Complementarity of the primers to the target nucleic acid need not be perfect. In various aspects, non-perfect complementary sequence can be used to avoid primer-dimers. Thus, by "complementary" or "substantially complementary" herein is meant that the probes are sufficiently complementary to the target sequences to hybridize under normal reaction conditions but not generate false-positive signals such as primer dimers. Deviations from perfect complementary are permissible so long as deviations are not sufficient to completely preclude hybridization. However, if the number of alterations or mutations is sufficient such that no hybridization can occur under the least stringent of hybridization conditions, as defined below, the sequence is not a complementary target sequence.

Although primers are generally single stranded, the nucleic acids as described herein may be single stranded or double stranded, as specified, or contain portions of both double stranded or single stranded sequence. The nucleic acid may be DNA, RNA, or hybrid, where the nucleic acid contains any combination of deoxyribo- and ribonucleotides, and any combination of bases, including uracil, adenine, thymine, cytosine, guanine, xanthine hypoxanthine, isocytosine, isoguanine, inosine, etc. As used herein, the term "nucleoside" includes nucleotides as well as nucleoside and nucleotide analogs, and modified nucleosides such as amino modified nucleosides. In addition, "nucleoside" includes non-naturally occurring analog structures. Thus, for example, the individual units of a peptide nucleic acid, each containing a base, are referred herein as a nucleotide.

The size of the primer nucleic acid may vary, as will be appreciated by those in the art, in general varying from 5 to 500 nucleotides in length. For example, with primers of between 10 and 100 nucleotides, between 12 and 75 nucleotides, and from 15 to 50 nucleotides can be used, depending on the use, required specificity, and the amplification technique.

For any primer pair, the ability of the primers to hybridize to each other may be examined by aligning the sequence of the first primer to the second primer. The stability of the hybrids, especially the thermal melting temperature (Tm), may be determined by the methods described below and by methods well known in the art. These include, but are not limited to, nearest-neighbor thermodynamic calculations (Breslauer, T. et al., Proc. Natl. Acad. Sci. USA 83:8893-97 (1986); Wetmur, J. G., Crit. Rev. Biochem. Mol. Biol. 26:227-59 (1991); Rychlik, W. et al., J. NIH Res. 6:78 (1994)), Wallace Rule estimations (Suggs, S. V. et al "Use of Synthetic oligodeoxribonucleotides for the isolation of specific cloned DNA sequences," Developmental biology using purified genes, D. B. Brown, ed., pp 683-693, Academic Press, New York (1981), and Tm estimations based on Bolton and McCarthy (see Baldino, F. J. et al., Methods Enzymol. 168: 761-77 (1989); Sambrook, J. et al., Molecular Cloning: A Laboratory Manual, Chapter 10, Cold Spring Harbor Laboratory Press, Cold Spring Harbor, N.Y., (2001)). All references are hereby expressly incorporated by reference. The effect of various parameters, including, but not limited to, ionic strength, probe length, G/C content, and mismatches are taken into consideration when assessing hybrid stability. Consideration of these factors are well known to those skilled in the art (see, e.g., Sambrook, J., supra).

The primers that can be used in the methods described herein can be used to amplify various target nucleic acids. A single primer set, for example a primer pair, may be used to amplify a single target nucleic acid. In another embodiment, multiple primer sets may be used to amplify a plurality of target nucleic acids. Amplifications may be conducted separately for each unique primer set, or in a single reaction vessel using combinations of primer sets, generally known in the art as multiplexing. When multiple primer sets are used in a single reaction, primers are designed to limit formation of undesirable products and limit interference between primers of each primer set.

The general PCR amplification reactions can be carried out according to procedures well known in the art, as discussed above (see, e.g., U.S. Pat. Nos. 4,683,195 and 4,683,202). The time and temperature of the primer extension step will depend on the polymerase, length of target nucleic acid being amplified, and primer sequence employed for the amplification. The number of reiterative steps required to sufficiently amplify the target nucleic acid will depend on the efficiency of amplification for each cycle and the starting copy number of the target nucleic acid. As is well known in the art, these parameters can be adjusted by the skilled artisan to effectuate a desired level of amplification. Those skilled in the art will understand that the present invention is not limited by variations in times, temperatures, buffer conditions, and the amplification cycles applied in the amplification process.

In hybridizing the primers to the target nucleic acids and in the disclosed amplification reactions, the assays are generally done under stringency conditions that allow formation of the hybrids in the presence of target nucleic acid. Those skilled in the art can alter the parameters of temperature, salt concentration, pH, organic solvent, chaotropic agents, or other variables to control the stringency of hybridization and also minimize hybridization of primers to non-specific targets (i.e., by use of "hot start" PCR or "touchdown" PCR).

In some aspects, the primers can comprise a detectable label. In some aspects, one primer or both primers of a primer pair or primer set can comprise a detectable label.

Also disclosed herein are kits for implementing the methods described herein. For example, disclosed herein are kits comprising one or more of the primer sets described herein. In some aspects the kits can comprise a first forward primer and a first reverse primer wherein the first forward primer comprises a 3' portion that hybridizes to a telomeric repeat sequence under annealing conditions; and wherein the first reverse primer comprises a 5' portion having an anchor sequence that does not hybridize to a telomeric repeat sequence.

The kits may also comprise buffers, enzymes, and containers for performing the amplification and analysis of the amplification products.

In some aspects, the kits can comprise one or more of the detection labels, polymerases or target nucleic acids described herein.

Additionally, the kits described herein can comprise any of the products and reagents required to carry out the methods described herein as well as instructions.

6. Correlations of Telomere Length with Clinical Condition or Optimal Therapeutic Regimen Average telomere length per chromosome end determined from genomic DNA is a measure of overall telomere abundance, and this has been shown to correlate with several important biological indices. These indices include, for example, risk of various disease conditions, e.g., cardiovascular risk, cancer risk, pulmonary fibrosis risk, infectious disease risk, and risk of mortality. Abundance of telomeres also correlates with chronological age, body-mass index, hip/weight ratio, and perceived stress. One measurement of the average telomere length or abundance is the telomere/single copy ("T/S") ratio. Such ratios in a given population can be divided into quantiles, e.g., into tertiles or quartiles. It has been found that individuals with telomere abundance by T/S ratios in the lower two tertiles are at significantly higher risk for cardiovascular disease than those in the top tertile for telomere length.

In the disclosed methods, "S" in the T/S ratio represents the average of the average length or abundance of at least two low copy number genes. In a further aspect, "S" in the T/S ratio represents the average of the average length or abundance of at least two single copy genes. In a still further aspect, "S" in the T/S ratio represents the average of the average length or abundance of two low copy number genes. In a further aspect, "S" in the T/S ratio represents the average of the average length or abundance of two single copy genes.

In general, percentile value of measure of average telomere length or abundance, e.g., T/S values represented as a percentage of the reference population (typically the highest tertile or quartile of telomere lengths), in a population correlates negatively with risk of disease, i.e. increased average telomere length or abundance is associated with lower disease or mortality risk or improved measures of health, while lower percentile scores are generally associated with decreased measures of health, and increased mortality and disease risk, including presence of "telomere disease" where telomeres are genetically short due to mutations or alternations in genes that negatively impact telomerase activity or function.

In a population, telomere length generally decreases with age. Accordingly, measures of average telomere length or abundance for an individual can be compared with measures for persons in the same age range in the population, that is, an age-matched population. For example, a person at age 30 might have a measure of telomere abundance about equal to the population average for age 30, or equal to the population average for age 20 or age 40. Correlations of a measure of average telomere length or abundance with measures of health can be more useful when compared with the measure for an age and gender-matched population. The range for an age matched population can be, for example, one year, two years, three years, four years, 5 years, 7 years or 10 years or up to 80 or more years.

Altered average telomere length or abundance determined from subject samples by the method of the present disclosure can be correlated with measures of health. Of particular interest are measures of health involving perceived stress. Apparent telomere shortening can be accelerated by genetic and environmental factors, including multiple forms of stress such as oxidative damage, biochemical stressors, chronic inflammation and viral infections (Epel, E. S. et al., *Proc. Natl. Acad. Sci. USA,* 2004, 49:17312-15). A convenient measure of general health status is the SF-36® Health Survey developed by John Ware (see, e.g., world wide web URL sf-36.org/tools/SF36.shtml). The SF-36 is a multi-purpose, short-form health survey with only 36 questions to be posed to patients, preferably by trained individuals. It provides an 8-scale profile of functional health and well-being scores as well as psychometrically-based physical and mental health summary measures and a preference-based health utility index. The SF-36 survey is used to estimate disease burden and compare disease-specific benchmarks with general population norms. The most frequently studied diseases and conditions include arthritis, back pain, cancer, cardiovascular disease, chronic obstructive pulmonary disease, depression, diabetes, gastro-intestinal disease, migraine headache, HIV/aids, hypertension, irritable bowel syndrome, kidney disease, low back pain, multiple sclerosis, musculoskeletal conditions, neuromuscular conditions, osteoarthritis, psychiatric diagnoses, rheumatoid arthritis, sleep disorders, spinal injuries, stroke, substance abuse, surgical procedures, transplantation and trauma (Turner-Bowker et al., *SF-36® Health Survey & "SF" Bibliography: Third Edition* (1988-2000), QualityMetric Incorporated, Lincoln, R.I., 2002). One skilled in the art will appreciate that other survey methods of general health status, for example, the RAND-36, may find use in the present disclosure.

In one aspect of the present disclosure, subject samples are collected over time and measurements of altered average telomere length or abundance are determined from the samples. Appropriate time periods for collection of a plurality of samples include, but are not limited to, 1 month, 3 months, 6 months, 1 year, 2 years, 5 years and 10 years (for example, the time between the earliest and the last sample can be about these time periods). This method allows for monitoring of patient efforts to improve their general health status and/or to monitor their health status and/or disease risk. Since shortened telomeres can trigger cell death or genomic instability which can contribute to cancer initiation or progress, a finding that the percentage of shortened telomere length is lowered or maintained with time within an individual indicates a health improvement, while increase of percentage of shortened telomeres overtime represents a decrease or worsening in health.

Measuring the number of repetitive units of telomeres has a wide variety of applications in medical diagnosis, e.g., for disease risk, disease prognosis, and therapeutics. In particular, measurement of telomere length finds application in assessing pathological conditions leading to the risk of disease. In one aspect of the disclosure, the disease is one associated with aging, for example but not limited to, cardiovascular disease, diabetes, cancer, liver fibrosis, and depression.

In one aspect, the present disclosure pertains to methods for allogeneic transplant hematopoietic stem cell donor selection, the method comprising: (a) obtaining samples from one or more HLA-matched potential donor subjects; (b) determining the average telomere length or abundance of the first amplicon for each of the HLA-matched donor subjects by the disclosed methods; (c) identifying one or more donor subjects from with average telomere length or abundance that is in upper $25^{th}$ percentile, upper $50^{th}$ percentile, or upper $75^{th}$ percentile for age-matched controls; (d) obtaining a transplantable hematopoietic stem cell sample from the identified donor subject; and (e) transplanting the hematopoietic stem cell sample to a recipient subject.

In one aspect, the present disclosure pertains to methods for allogeneic transplant hematopoietic stem cell donor selection, the method comprising: (a) obtaining samples from one or more HLA-matched potential donor subjects; (b) determining the average telomere length or abundance of the first amplicon for each of the HLA-matched donor subjects by the disclosed methods; (c) identifying one or more donor subjects from with average telomere length or abundance that is in upper $25^{th}$ percentile for age-matched controls; (d) obtaining a transplantable hematopoietic stem cell sample from the identified donor subject; and (e) transplanting the hematopoietic stem cell sample to a recipient subject.

In one aspect, the present disclosure pertains to methods for allogeneic transplant hematopoietic stem cell donor selection, the method comprising: (a) obtaining samples from one or more HLA-matched potential donor subjects; (b) determining the average telomere length or abundance of the first amplicon for each of the HLA-matched donor subjects by the disclosed methods; (c) identifying one or more donor subjects from with average telomere length or abundance that is in upper $50^{th}$ percentile for age-matched controls; (d) obtaining a transplantable hematopoietic stem cell sample from the identified donor subject; and (e) transplanting the hematopoietic stem cell sample to a recipient subject.

In one aspect, the present disclosure pertains to methods for allogeneic transplant hematopoietic stem cell donor selection, the method comprising: (a) obtaining samples from one or more HLA-matched potential donor subjects; (b) determining the average telomere length or abundance of the first amplicon for each of the HLA-matched donor subjects by the disclosed methods; (c) identifying one or more donor subjects from with average telomere length or abundance that is in upper $75^{th}$ percentile for age-matched controls; (d) obtaining a transplantable hematopoietic stem cell sample from the identified donor subject; and (e) transplanting the hematopoietic stem cell sample to a recipient subject.

In a further aspect, the recipient subject has been diagnosed with a cancer, cardiovascular disease, or with a need for a bone marrow transplant.

In a further aspect, the recipient subject has been diagnosed with a cancer. In a still further aspect, the cancer is a leukemia or lymphoma. In a yet further aspect, the cancer is a neuroblastoma. In an even further aspect, the cancer is multiple myeloma.

In a further aspect, the recipient subject has received radiation therapy and/or chemotherapy treatment. In a still further aspect, the recipient subject is in remission.

In a further aspect, the hematopoietic stem cell sample comprises bone marrow obtained from the identified donor subject. In a still further aspect, the hematopoietic stem cell sample comprises peripheral blood stem cells obtained from the identified donor subject.

In one aspect, the present disclosure finds use in the assessment and monitoring of cardiovascular disease. Telomere length in white blood cells has been shown to be shorter in patients with severe triple vessel coronary artery disease than it is in individuals with normal coronary arteries as determined by angiography (Samani, N. J. et al., *Lancet*, 2001, 358:472-73), and also in patients who experiencing a premature myocardial infarction before age 50 years as compared with age- and sex-matched individuals without such a history (Brouilette S. et al., *Arterioscler. Thromb. Vasc. Biol.*, 2003, 23:842-46). Brouilette et al. (*Lancet*, 2007, 369:107-14) has suggested that shorter leucocyte telomeres in people prone to coronary heart disease could indicate the cumulative effect of other cardiovascular risk factors on telomere length. Increased oxidative stress also contributes to atherosclerosis, and increased oxidant stress has been shown to increase rates of telomere attrition in vitro (Harrison, D., *Can. J. Cardiol.*, 1998, 14(suppl D):30D-32D; von Zglinicki, T., *Ann. N. Y. Acad. Sci.*, 2000, 908:99-110). In cross-sectional studies, smoking, body-mass index, and type 1 diabetes mellitus have also been reported to be associated with shorter leucocyte telomere length (Valdes, A., et al., *Lancet*, 2005, 366:662-64; Jeanclos, E. et al., *Diabetes*, 1998, 47:482-86). Increased life stress, a factor known to increase the risk of coronary heart disease, has been shown to be associated with shorter telomeres, possibly as a consequence of increased oxidative stress (Epel, 2004, ibid.). Thus, smokers and patients with a high body-mass index, diabetes and/or increased life stress would all benefit from determination and continued monitoring of their telomere abundance according to the method of the disclosure.

Type 2 diabetes is characterized by shorter telomeres (Salpea, K. and Humphries, S. E., *Atherosclerosis*, 2010, 209(1):35-38). Shorter telomeres have also been observed in type 1 diabetes patients (Uziel O. et al., *Exper. Gerontology*, 2007, 42:971-978). The etiology of the disease in type 1 diabetes is somewhat different from that in type 2, although in both cases, beta cell failure is the final trigger for full-blown disease. Telomere length is thus a useful marker for diabetes since it is associated with the disease progression. Adaikalakoteswari et al. (*Atherosclerosis*, 2007, 195: 83-89) have shown that telomeres are shorter in patients with pre-diabetic impaired glucose tolerance compared to controls. In addition, telomere shortening has been linked to diabetes complications, such as diabetic nephropathy (Verzola D. et al., *Am. J. Physiol.*, 2008, 295:F1563-1573), microalbuminuria (Tentolouris, N. et al., *Diabetes Care*, 2007, 30:2909-2915), and epithelial cancers (Sampson, M. J. et al., *Diabetologia*, 2006, 49:1726-1731) while telomere shortening seems to be attenuated in patients with well-controlled diabetes (Uziel, 2007, ibid.). The method of the present disclosure is particularly useful in monitoring the status of pre-diabetic and diabetic patients to provide an early warning for these complications and others.

The present disclosure is useful for determining telomere lengths of various types of cancer cells because activation of telomerase activity is associated with immortalization of cells. While normal human somatic cells do not or only transiently express telomerase and therefore shorten their telomeres with each cell division, most human cancer cells typically express high levels of telomerase and show unlimited cell proliferation. High telomerase expression allows cells to proliferate and expand long term and therefore supports tumor growth (Roth, A. et al., in *Small Molecules in Oncology, Recent Results in Cancer Research*, U. M. Martens (ed.), Springer Verlag, 2010, pp. 221-234). Shorter telomeres are significantly associated with risk of cancer, especially cancers of the bladder and lung, smoking-related, the digestive system and the urogenital system. Excessive telomere shortening likely plays a role in accelerating tumor onset and progression (Ma H. et al., *PLoS ONE*, 2011, 6(6): e20466. doi:10.1371/journal.pone.0020466). Studies have further shown that the effect of shortened telomeres on breast cancer risk is significant for certain population subgroups, such as premenopausal women and women with a poor antioxidative capacity (Shen J., et al., *Int. J. Cancer*, 2009, 124:1637-1643). In addition to the assessing and monitoring cancers in general, the present disclosure is particularly useful for the monitoring of oral cancers if genomic DNA derived from saliva samples is utilized.

Cirrhosis of the liver is characterized by increasing fibrosis of the organ often associated with significant inflammatory infiltration. Wiemann et al. (*FASEB Journal*, 2002, 16(9):935-982) have shown that telomere shortening is a disease- and age-independent sign of liver cirrhosis in humans. Telomere shortening is present in cirrhosis induced by viral hepatitis (chronic hepatitis A and B), toxic liver damage (alcoholism), autoimmunity, and cholestasis (PBC and PSC); telomeres are uniformly short in cirrhosis independent of the age of the patients. Telomere shortening and senescence specifically affect hepatocytes in the cirrhotic liver and both parameters strongly correlate with progression of fibrosis during cirrhosis. Thus, the method of the present disclosure finds use in diagnosing and monitoring liver fibrosis.

Depression has been likened to a state of "accelerated aging," and depressed individuals have a higher incidence of various diseases of aging, such as cardiovascular and cerebrovascular diseases, metabolic syndrome, and dementia. People with recurrent depressions or those exposed to chronic stress exhibit shorter telomeres in white blood cells. Shorter telomere length is associated with both recurrent depression and cortisol levels indicative of exposure to chronic stress (Wikgren, M. et al., *Biol. Psych.*, 2011, DOI: 10.1016/j.biopsych.2011.09.015). However, not all depressed individuals show shortened telomeres equally because of a large variance in depressive episodes over a lifetime. Those who suffered from depression for long durations have significantly shorter telomeres due to longer exposure to oxidative stress and inflammation induced by psychological stress when compared with control populations (Wolkowitz et al., *PLoS One*, 2011, 6(3):e17837). Thus, the method of the present disclosure may find use in monitoring depression.

Abnormal telomere length is associated with chronic infection including HIV (Effros R B et al, AIDS. 1996 July; 10(8):F17-22, Pommier et al Virology. 1997, 231(1):148-54), and HBV, HCV and CMV (Telomere/telomerase dynamics within the human immune system: effect of chronic infection and stress. (Effros R B, Exp Gerontol. 2011 February-March; 46(2-3):135-40. Rejuvenation Res. 2011 February; 14(1):45-56. doi: 10.1089rej.2010.1085. Epub 2010 Sep. 7.)

In Harley et al. ("A natural product telomerase activator as part of a health maintenance program", Harley C B, Liu W, Blasco M, Vera E, Andrews W H, Briggs L A, Raffaele J M, Rejuvenation Res. 2011 February; 14(1):45-56), it was found that individuals who were CMV seropositive had shorter telomeres than those who were CMV negative, and moreover, the CMV positive subjects were more likely to respond to a nutritional supplement program of TA-65, a natural product-derived telomerase activator along with other supplements, in reducing the abundance of senescent CD8+/CD28− cells, suggesting a companion diagnostics application for measuring average telomere length or abundance of short telomeres, in conjunction with administration of telomerase activators or other agents that lead to longer telomeres.

Measurement of average telomere length can be used as indicator of prognosis disease progression and treatment outcome.

One study reported that telomere length in CD4+ cells is related to inflammatory grade, fibrosis stage, laboratory indices of severity, subsequent hepatic decompensation and treatment outcome in patients with chronic HCV infection (Hoare et al, *J. Hepatol.*, 2010, 53(2):252-260).

In another report, longer leukocyte telomere length predicts increased risk of hepatitis B virus-related hepatocellular carcinoma (Liu et al, 2011, 117(18):4247-56.)

In the case of HIV, telomere shortening is caused by viral infection. In addition, the nucleoside analog reverse-transcriptase inhibitors used to treat HIV are telomerase inhibitors (Strahl and Blackburn, *Mol Cell Biol.*, 1996, 16(1):53-65; Hukezalie et al, *PLoS One*, 2012, 7(11):e47505). Measurement of short telomere abundance might help determine the side effects and efficacy of HAART treatment.

The present disclosure also finds use in diagnosis of diseases related to early onset of aging. For example, individuals with Hutchinson Gilford progeria disease show premature aging and reduction in proliferative potential in fibroblasts associated with loss of telomeric length (Allsopp, R. C. et al, *Proc. Natl. Acad. Sci. USA*, 1992, 89:10114-10118). Amplification and quantitation of the number of telomeric repeats according to the method of this disclosure is useful for determining disease risk or prognosis and taking appropriate interventional steps as described above.

In one aspect of the present disclosure, both the presence and the progress of telomeric-specific diseases may be determined using samples. Telomeric diseases are associated with an abnormal or premature shortening of telomeres, which can, for example, result from defects in telomerase activity. Telomerase is a ribonucleoprotein complex required for the replication and protection of telomeric DNA in eukaryotes. Cells lacking telomerase undergo a progressive loss of telomeric DNA that results in loss of viability and a concomitant increase in genome instability. These diseases may be inherited and include certain forms of congenital aplastic anemia, in which insufficient cell divisions in the stem cells of the bone marrow lead to severe anemia. Certain inherited diseases of the skin and the lungs are also caused by telomerase defects. For telomere diseases, a threshold for T/S<0.5 is appropriate for some conditions. Also, a commonly used metric is an age-adjusted percentile telomere score less than <10% or preferably <1% relative to a normal population.

Dyskeratosis congenita (DKC), also known as Zinsser-Engman-Cole syndrome, is a rare, progressive bone marrow failure syndrome characterized by mucocutaneous abnormalities: reticulated skin hyperpigmentation, nail dystrophy, and oral leukoplakia (Jyonouchi S. et al., *Pediatr. Allergy Immunol.*, 2011, 22(3):313-9; Bessler M., et al., *Haematologica*, 2007, 92(8):1009-12). Evidence exists for telomerase dysfunction, ribosome deficiency, and protein synthesis dysfunction in this disorder. Early mortality is often associated with bone marrow failure, infections, fatal pulmonary complications, or malignancy. The disease is inherited in one of three types: autosomal dominant, autosomal recessive, or the most common form, X-linked recessive (where the gene responsible for DC is carried on the X-chromosome). Early diagnosis and measurement of disease progress using the method of this disclosure is very beneficial for families with these genetic characteristics so that early treatment with anabolic steroids or bone-marrow-stimulating drugs can help prevent bone marrow failure. The non-invasive, patient friendly saliva-testing method of the present disclosure is particularly useful for DKC because babies and small children need testing and continued monitoring.

Idiopathic interstitial pneumonias are characterized by damage to the lung parenchyma by a combination of fibrosis and inflammation. Idiopathic pulmonary fibrosis (IPF) is an example of these diseases that causes progressive scarring of the lungs. Fibrous scar tissue builds up in the lungs over time, affecting their ability to provide the body with enough oxygen. Heterozygous mutations in the coding regions of the telomerase genes, TERT and TERC, have been found in familial and sporadic cases of idiopathic interstitial pneumonia. All affected patients with mutations have short telomeres. A significant fraction of individuals with IPF have short telomere lengths that cannot be explained by coding mutations in telomerase (Cronkhite, J. T., et al., *Am. J. Resp. Crit. Care Med.*, 2008, 178:729-737). Thus, telomere shortening can be used as a marker for an increased predisposition toward this age-associated disease (Alder, J. K., et al., *Proc. Natl. Acad. Sci. USA,* 2008, 105(35):13051-13056). Further, the course of IPF varies from person to person. For some, the disease may progress slowly and gradually over years, while for others it may progress rapidly. The method of the present may be conveniently used to monitor the course of pulmonary fibrosis and taking appropriate interventional steps as described above.

Aplastic anemia is a disease in which bone marrow stops making enough red blood cells, white blood cells and platelets for the body. Any blood cells that the marrow does make are normal, but there are not enough of them. Aplastic anemia can be moderate, severe or very severe. People with severe or very severe aplastic anemia are at risk for life-threatening infections or bleeding. Patients with aplastic anemia who have short telomeres, or are carrying telomerase mutations, have an increased risk of developing myelodysplasia and genomic instability leading to chromosomal aberrations and cancer (Calado et al. Leukemia (2011), 1-8).

Telomerase deficiency may cause variable degrees of telomere shortening in hematopoietic stem cells and lead to chromosomal instability and malignant transformation (Calado, R. T. and Young, N. S., *The Hematologist,* 2010 world wide web URL hematology.org/Publications/Hematologist/2010/4849.aspx). Aplastic anemia patients with shorter telomeres have a lower survival rate and are much more likely to relapse after immunotherapy than those with longer telomeres. Scheinberg et al. (*JAMA,* 2010, 304(12):1358-1364) found that relapse rates dropped as telomere lengths increased. The group of patients with the shortest telomeres was also at greater risk for a conversion to bone marrow cancer and had the lowest overall survival rates. The method of the present disclosure can be used in aplastic anemia patients to monitor the risk of developing major complications so that the clinical management of an individual may be tailored accordingly.

In another aspect, the present disclosure is useful in monitoring effectiveness of therapeutics or in screening for drug candidates affecting telomere length or telomerase activity. The ability to monitor telomere characteristics can provide a window for examining the effectiveness of particular therapies and pharmacological agents. The drug responsiveness of a disease state to a particular therapy in an individual can be determined by the method of the present disclosure. For example, the present disclosure finds use in monitoring the effectiveness of cancer therapy since the proliferative potential of cells is related to the maintenance of telomere integrity. As described above, while normal human somatic cells do not or only transiently express telomerase and therefore shorten their telomeres with each cell division, most human cancer cells typically express high levels of telomerase and show unlimited cell proliferation. Roth et al., (ibid., 2010) have suggested that individuals with cancer who have very short telomeres in their tumors (in which the shortest telomeres in most cells are near to telomere dysfunction) and high telomerase activity might benefit the most from anti-cancer telomerase-inhibiting drugs. Because telomerase is either not expressed or expressed transiently and at very low levels in most normal cells, telomerase inhibition therapies may be less toxic to normal cells than conventional chemotherapy. An example of such drugs is the short oligonucleotide-based telomerase inhibitor imetelstat (previously named GRN163L). Imetelstat is a novel lipid-based conjugate of the first-generation oligonucleotide GRN163 (Asai, A. et al., *Cancer Res.,* 2003, 63:3931-3939). However, cancer patients having very short telomeres in normal blood cells (particularly their granulocytes) are at higher risk of adverse effects of imetelstat on proliferative tissues such as the bone marrow. Rattain et al. (2008) found that such subjects with short granulocyte telomere length were more likely to have bone marrow failure symptoms such as neutropenia or thrombocytopenia. In this situation, a doctor might prescribe a lower dose of imetelstat, a different drug, or more frequent monitoring for bone marrow problems.

In other aspects, drug efficacy in the treatment of diseases of aging, for example but not limited to, cardiovascular disease, diabetes, pulmonary fibrosis, liver fibrosis, interstitial pneumonia and depression. In the case of cardiovascular disease, Brouilette et al. reported that middle-aged men with shorter telomere lengths than control groups benefit the most from lipid-lowering therapy with pravastatin (Brouilette, S. W. et al., *Lancet,* 2007, 369:107-114). Satoh et al. (*Clin. Sci.,* 2009, 116:827-835) indicating that intensive lipid-lowering therapy protected telomeres from erosion better in patients treated with atorvastatin when compared with patients treated with moderate pravastatin therapy. The method of the present disclosure can be used to monitor the efficacy of statins in treated patients, wherein shorter telomere length correlates with better drug efficacy. Since subjects with the longest telomeres did not on average benefit from prophylactic statins, a doctor might suggest that the patient be especially compliant with good lifestyle habits as part of their treatment program. Conversely, patients with short telomeres who fear side effects of chronic statin usage might be persuaded to take statins based on their higher probability of benefiting from statins. Examples of statins that can be used include niacin (ADVICOR, SIMCOR), lovastatin (ALTOPREV, MEVACOR), amolopidine (CADUET), rosuvastatin (CRESTOR), sitagliptin/simvastatin (JUVISYNC), fluvastatin (LESCOL), pravastatin (PRAVACHOL), atorvastatin (LIPITOR), pitavastatin (LIVALO), and ezetimibe/simvastatin (VYTORIN).

In one aspect, the present disclosure pertains to methods for reclassification of cardiovascular disease risk, the method comprising: (a) obtaining a sample a subject, wherein the subject has been diagnosed to meet 2013 ACC/AHA Guideline on the Treatment of Blood Cholesterol criteria for low-intensity statin therapy; (b) determining the average length or abundance of the first amplicon relative to the average abundance of the second and third amplicon in the sample by the disclosed methods; (c) diagnosing the subject at higher cardiovascular risk when the sample has been determined to have a first amplicon average length or abundance relative to the average abundance of the second and third amplicon in the lower $25^{th}$ percentile, lower $50^{th}$ percentile, or lower $75^{th}$ percentile for age-matched controls; and (d) administering to the subject diagnosed at higher cardiovascular risk: (i) a modified statin therapy; and/or (ii) a second therapeutic agent known to treat cardiovascular disease.

In one aspect, the present disclosure pertains to methods for reclassification of cardiovascular disease risk, the method comprising: (a) obtaining a sample a subject, wherein the subject has been diagnosed to meet 2013 ACC/AHA Guideline on the Treatment of Blood Cholesterol criteria for low-intensity statin therapy; (b) determining the average length or abundance of the first amplicon relative to the average abundance of the second and third amplicon in the sample by the disclosed methods; (c) diagnosing the subject at higher cardiovascular risk when the sample has been determined to have a first amplicon average length or abundance relative to the average abundance of the second and third amplicon in the lower $25^{th}$ percentile for age-matched controls; and (d) administering to the subject diagnosed at higher cardiovascular risk: (i) a modified statin therapy; and/or (ii) a second therapeutic agent known to treat cardiovascular disease.

In one aspect, the present disclosure pertains to methods for reclassification of cardiovascular disease risk, the method comprising: (a) obtaining a sample a subject, wherein the subject has been diagnosed to meet 2013 ACC/AHA Guideline on the Treatment of Blood Cholesterol criteria for low-intensity statin therapy; (b) determining the average length or abundance of the first amplicon relative to the average abundance of the second and third amplicon in the sample by the disclosed methods; (c) diagnosing the subject at higher cardiovascular risk when the sample has been determined to have a first amplicon average length or abundance relative to the average abundance of the second and third amplicon in the lower $50^{th}$ percentile for age-matched controls; and (d) administering to the subject diagnosed at higher cardiovascular risk: (i) a modified statin therapy; and/or (ii) a second therapeutic agent known to treat cardiovascular disease.

In one aspect, the present disclosure pertains to methods for reclassification of cardiovascular disease risk, the method comprising: (a) obtaining a sample a subject, wherein the subject has been diagnosed to meet 2013 ACC/AHA Guideline on the Treatment of Blood Cholesterol criteria for low-intensity statin therapy; (b) determining the average length or abundance of the first amplicon relative to the average abundance of the second and third amplicon in the sample by the disclosed methods; (c) diagnosing the subject at higher cardiovascular risk when the sample has been determined to have a first amplicon average length or abundance relative to the average abundance of the second and third amplicon in the lower $75^{th}$ percentile for age-matched controls; and (d) administering to the subject diagnosed at higher cardiovascular risk: (i) a modified statin therapy; and/or (ii) a second therapeutic agent known to treat cardiovascular disease.

In further aspects, drug effectiveness in the treatment of telomeric diseases, for example but not limited to, Dyskeratosis congenita, pulmonary fibrosis, and aplastic anemia, may be measured. For example, dyskeratosis congenita and pulmonary fibrosis are both treated with high-dose steroids, which are well known to have numerous deleterious side effects. Use of the lowest possible steroid dose is thus highly desirable, making the method of the present disclosure a valuable tool for monitoring these patients.

In another aspect, the present disclosure finds use as a general method of screening for candidate drugs, dietary supplements, and other interventions including lifestyle changes which affect biological pathways regulating telomere length, such as telomerase activity. Ability to rapidly and specifically amplify telomere repeats in a quantitative manner provides a high throughput screening method for identifying small molecules, candidate nucleic acids, and peptides agents and other products or interventions affecting telomere dynamics in a cell. Drug or other product candidates that have a positive, telomere lengthening effect on normal cells would be preferred in the treatment of degenerative, or cell senescence related conditions over those with telomere shortening (or telomerase inhibiting) effects, everything else being equal. In the case of treatment of cancer, drugs that have a negative, telomere shortening effect, especially in cancer cells would be preferred.

EXAMPLES

Example 1—Triplex qPCR Assay

Each PCR reaction was carried out in a total volume of 10 µL per well of a standard 384 well assay plate. The standard reaction mix contained the following components: 5 ng target DNA, 1.0 µM EvaGreen® Dye (Biotium, Hayward, Calif.), 300 nM Tel G modified primer, 300 nM Tel C modified primer, 300 nM B2M-F primer, 300 nM B2M-R primer, 100 nM B2M probe, 1× RNase P Mix (TaqMan® Copy Number Reference Assay RNase P, Thermo Fisher Scientific, Inc.), 1× Quantifast Probe PCR Master Mix (QIAGEN, Inc., Germantown, Md.). Table 2 below provides various primer sequences.

TABLE 2

| Oligo | Length (nucleotides) | SEQ ID NO. | Sequence |
|---|---|---|---|
| Tel G modified | 45 | 1 | 5'-ACACCTCCTCCATGGTTTGGGTT TGGGTTTGGGTTTGGGTTAGTG-3' |
| Tel C modified | 43 | 2 | 5'-TGTTAGCGACGCGATATCCCTAT CCCTATCCCTATCCCTAACA-3' |
| B2M-F | 22 | 3 | 5'-CCAGCAGAGAATGGAAAGTCAA-3' |
| B2M-R | 28 | 4 | 5'-TCTCTCTCCATTCTTCAGTAAGT CAACT-3' |
| B2M-P* | 27 | 5 | 5'-ATGTGTCTGGGTTTCATCCATC CGACA3-3' |

*The B2M-P probe oligonucleotide has a Cy5 group covalently linked to the 5' terminus of the primer sequence and an Iowa Black ® RQ moiety covalently linked to the 3' terminus of the primer sequence.

The standard cycling conditions for the disclosed triplex qPCR assay are those shown in Table 3.

TABLE 3

| Cycling Step | Temp (° C.) | Time | # Cycles |
|---|---|---|---|
| Cycle 1 | 96 | 2 min | 1 |
|  | 49 | 15 sec |  |
| Cycle 2 | 96 | 2 min | 1 |
|  | 49 | 30 sec |  |
| Denaturation | 90 | 10 sec | 40 |
| Annealing | 62 | 30 sec |  |
| Extension | 70* | 30 sec |  |
| Melt Curve | 95 | 5 sec | 1 |
|  | 65 | 1 min | 1 |
|  | 97 | Continuous | 1 |

*Signal data acquisition during this step.

The primers, target nucleic acids, and detection channels for the various amplicons in the disclosed triplex qPCR assay are given in Table 4 below. Each of the targets was quantified using the absolute quantification method in Roche LC480 with the second derivative method. An 8-point, 2-fold dilution of the mosaic male genomic DNA was used to generate the standard curve, from which the concentration of each of three targets for each sample was calculated. The 8 point standard curve used the following genomic DNA concentrations was as shown in Table 4. The concentrations of T, B and R were used to calculate the average telomere length.

TABLE 4

| Primer/probe | Tel C modified/Tel G modified/EvaGreen | B2M-F/B2M-R/B2M-P | RNAP-F/RNAP-R/RNAP-P |
|---|---|---|---|
| Target nucleic acid | Telomere | β2-microglobulin | RNase P |
| Detection channel | FAM (465-510 nm) | Cy5 (618-660 nm) | VIC (533-580 nm) |

Example 2—Assessment of the Effect of Tel G Modified and Tel C Modified Primer Concentration The standard reaction conditions described above were used, except that the concentration of the Tel G modified and Tel C modified were varied. The following concentrations were examined: 400 nM Tel G modified and 400 nM Tel C modified; 300 nM Tel G modified and 100 nM Tel C modified; 600 nM Tel G modified and 100 nM Tel C modified; 300 nM Tel G modified and 300 nM Tel C modified; and 600 nM Tel G modified and 300 nM Tel C modified. The melting curves for the reactions with the foregoing Tel G modified/Tel C modified primer concentrations are shown in FIG. 2A-FIG. 2F. The data show that when the reaction was carried out with 300 nM Tel G modified and 300 nM Tel C modified, all three targets have similar amplification amplitude, suggesting that all three PCR reactions generate approximately similar amounts of products and the assay reaches the desired balance for the three targets. Comparable amounts of the three amplicons at the end of the PCR reaction when equilibrium is reached is an indicator that the none of the PCR reagents (enzyme, nucleotides, primers) are limiting for any of the three PCR products.

Example 3—Amplification Efficiency

An 8-point 2-fold serial dilution of the Mosaic Male genomic DNA was used to calculate the PCR efficiencies. The DNA concentration in the final PCR reaction for each point is shown in Table 5. The PCR efficiencies of each of the target for each primer combination tested were obtained with absolute quantification method in the Roche LC480 program and are summarized in Table 6.

TABLE 5

| Standard point | Final concentration in PCR (ng/μl) |
|---|---|
| Std1 | 5 |
| Std2 | 2.5 |
| Std3 | 1.25 |
| Std4 | 0.625 |
| Std5 | 0.3125 |
| Std6 | 0.1563 |
| Std7 | 0.0781 |
| Std8 | 0.0391 |

TABLE 6

| | PCR Amplification Efficiencies | | |
|---|---|---|---|
| | T | RNaseP | B2M |
| T only | 104.0% | — | — |
| S only | — | 98.6% | 96.3% |
| 300 nM TelG | 97.5% | 106.8% | 97.4% |

TABLE 6-continued

| | PCR Amplification Efficiencies | | |
|---|---|---|---|
| | T | RNaseP | B2M |
| 100 nM TelC 300 nM TelG | 95.4% | 107.9% | 96.3% |
| 300 nM TelC 400 nM TelG | 97.4% | 105.9% | 96.6% |
| 400 nM TelC 600 nM TelG | 95.1% | 105.2% | 97.5% |
| 100 nM TelC | | | |

Example 4—Amplification Efficiency

Figure 3A:
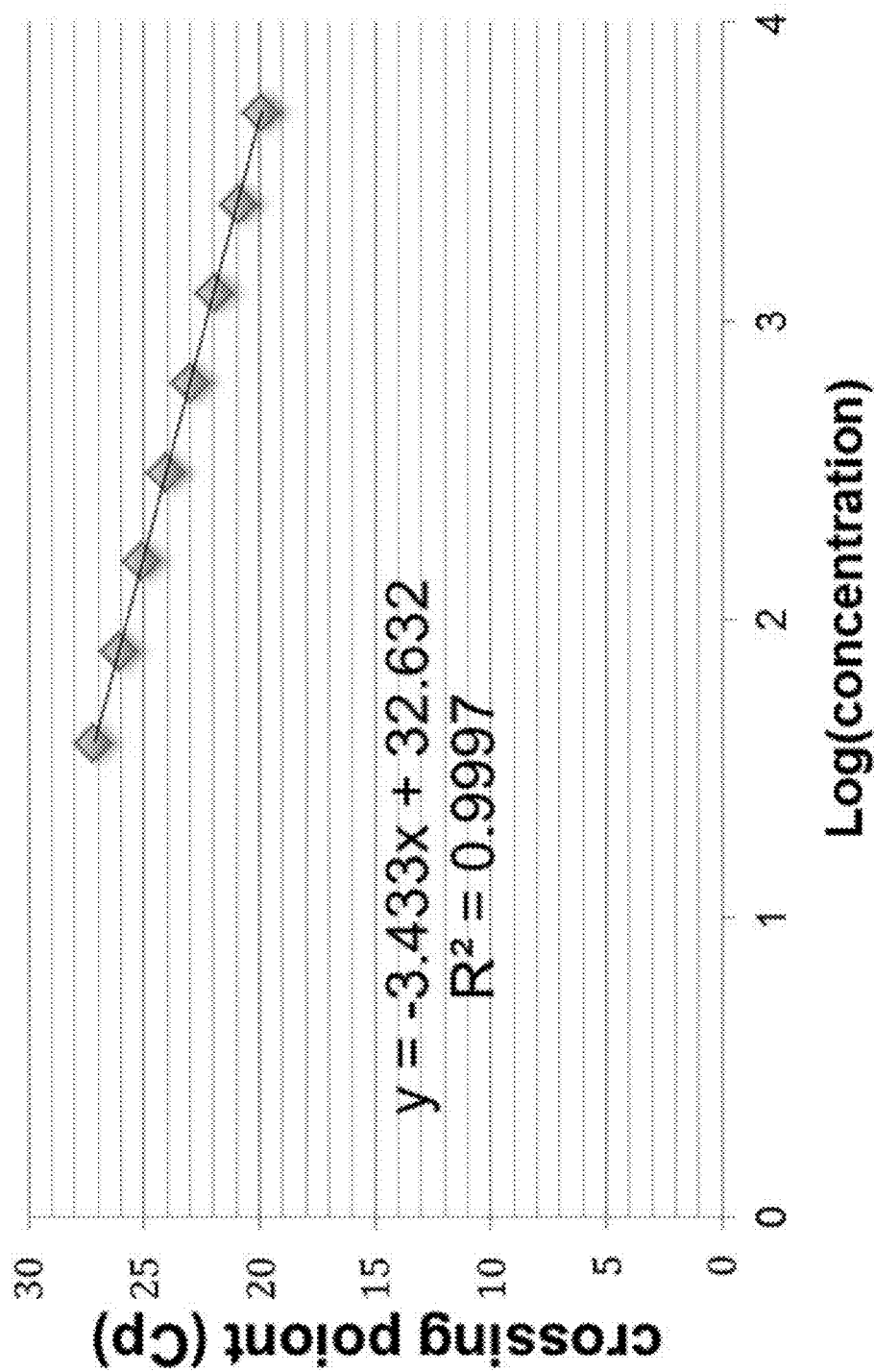
FIG. 3A-FIG. 3C show representative linear regression lines of crossing point ("Cp") versus the log (concentration) of target DNA for the human genomic target DNA (mosaic male genomic DNA), which comprises the target nucleic acid sequences for telomere sequences, the RNase P gene, and the β2-microglobulin gene. The Cp was calculated using the second derivative program of the Roche LC480 Light Cycler instrument.
Figure 3B:
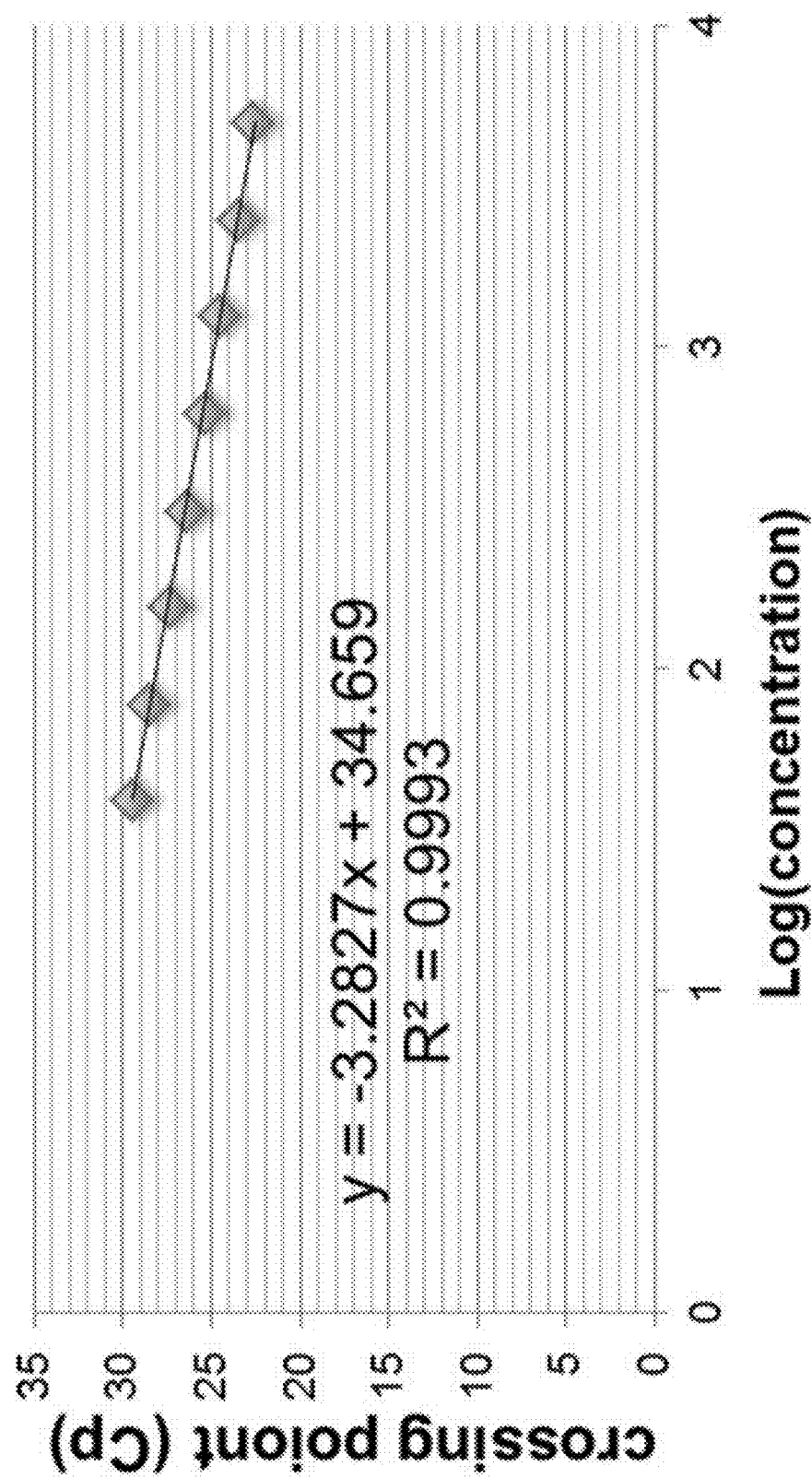
Figure 3C:
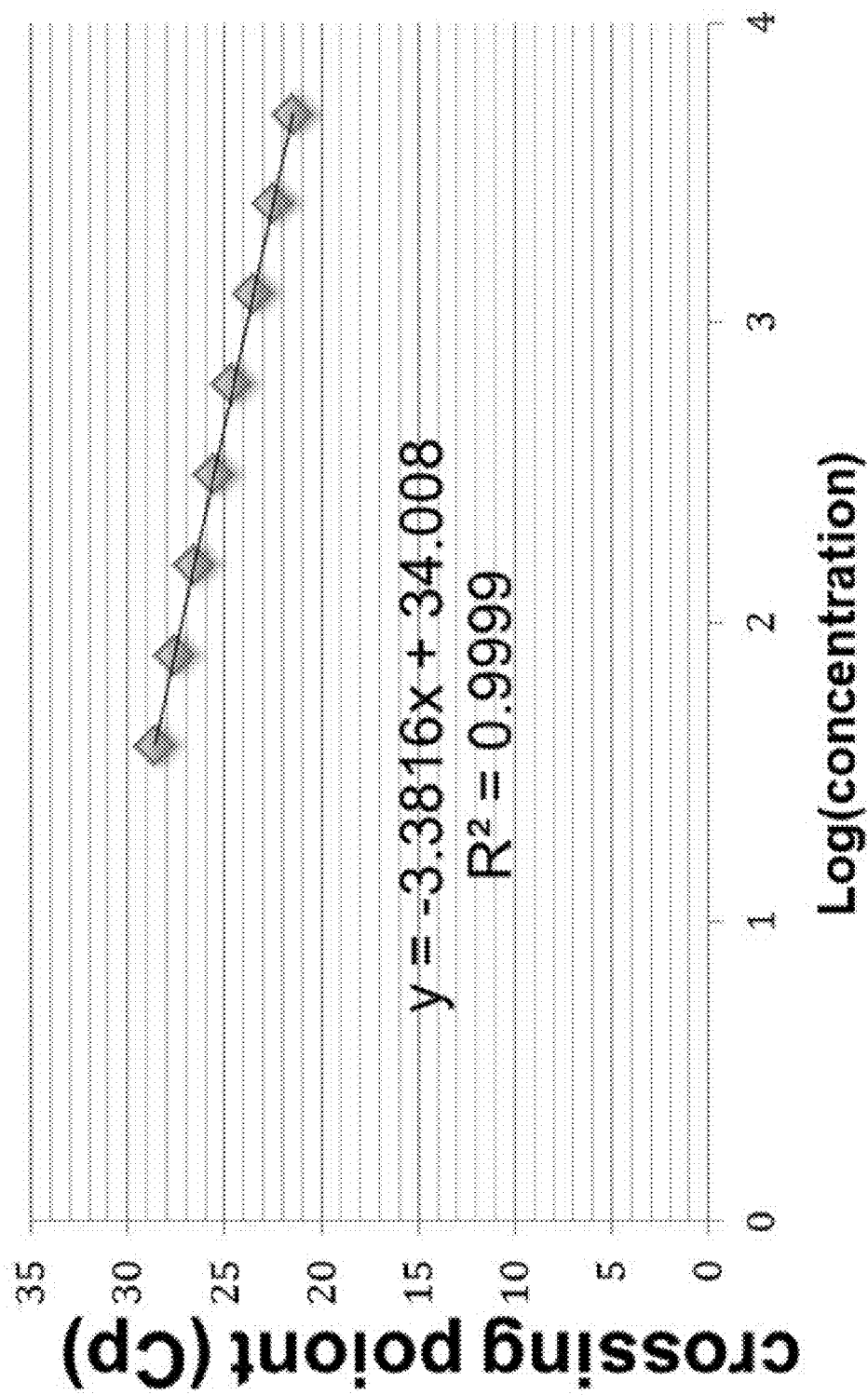
Figure 4A:
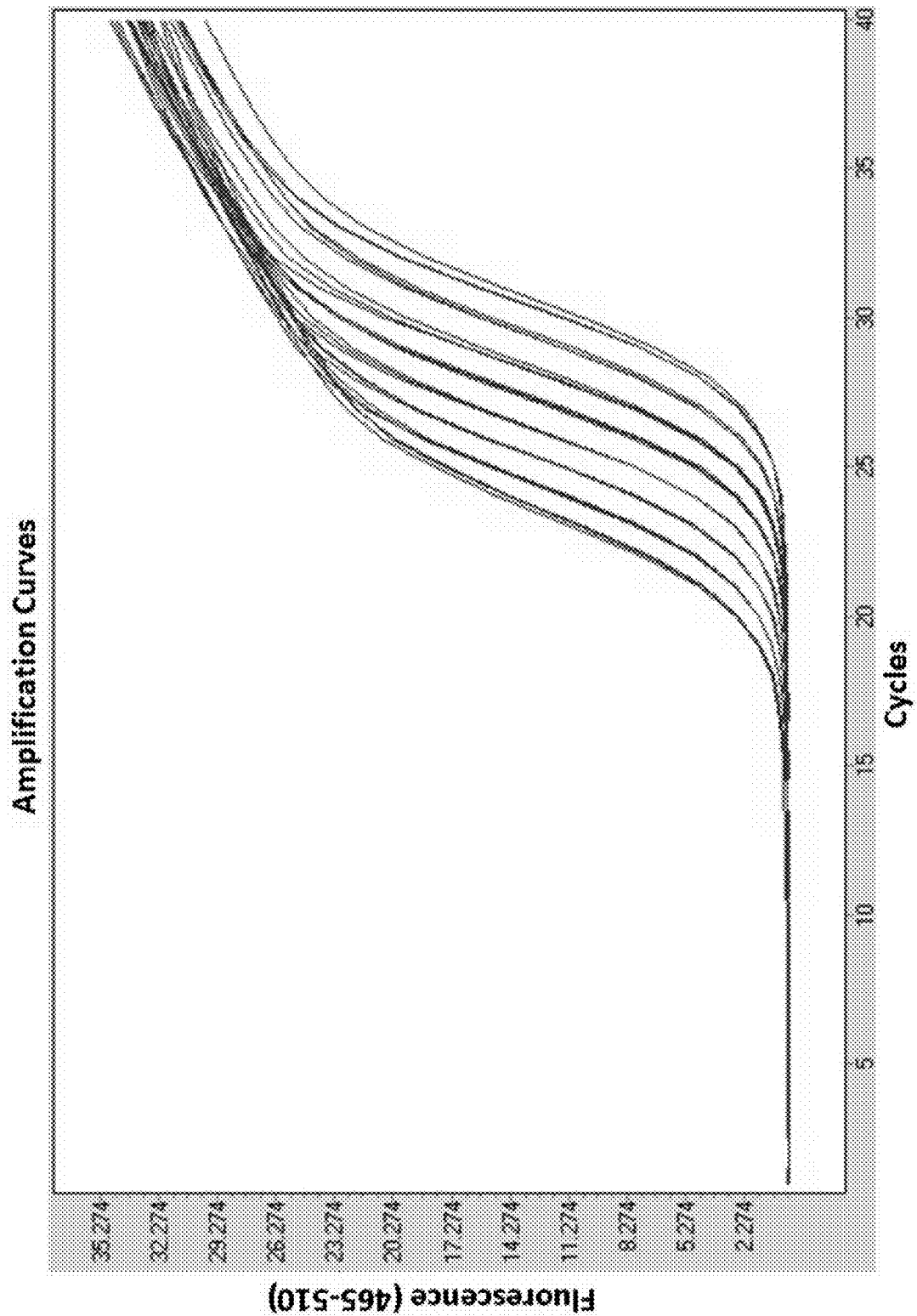
FIG. 4A-FIG. 4C show representative amplification curves amplification reactions carried out using human genomic target DNA (mosaic male genomic DNA).
Figure 4B:
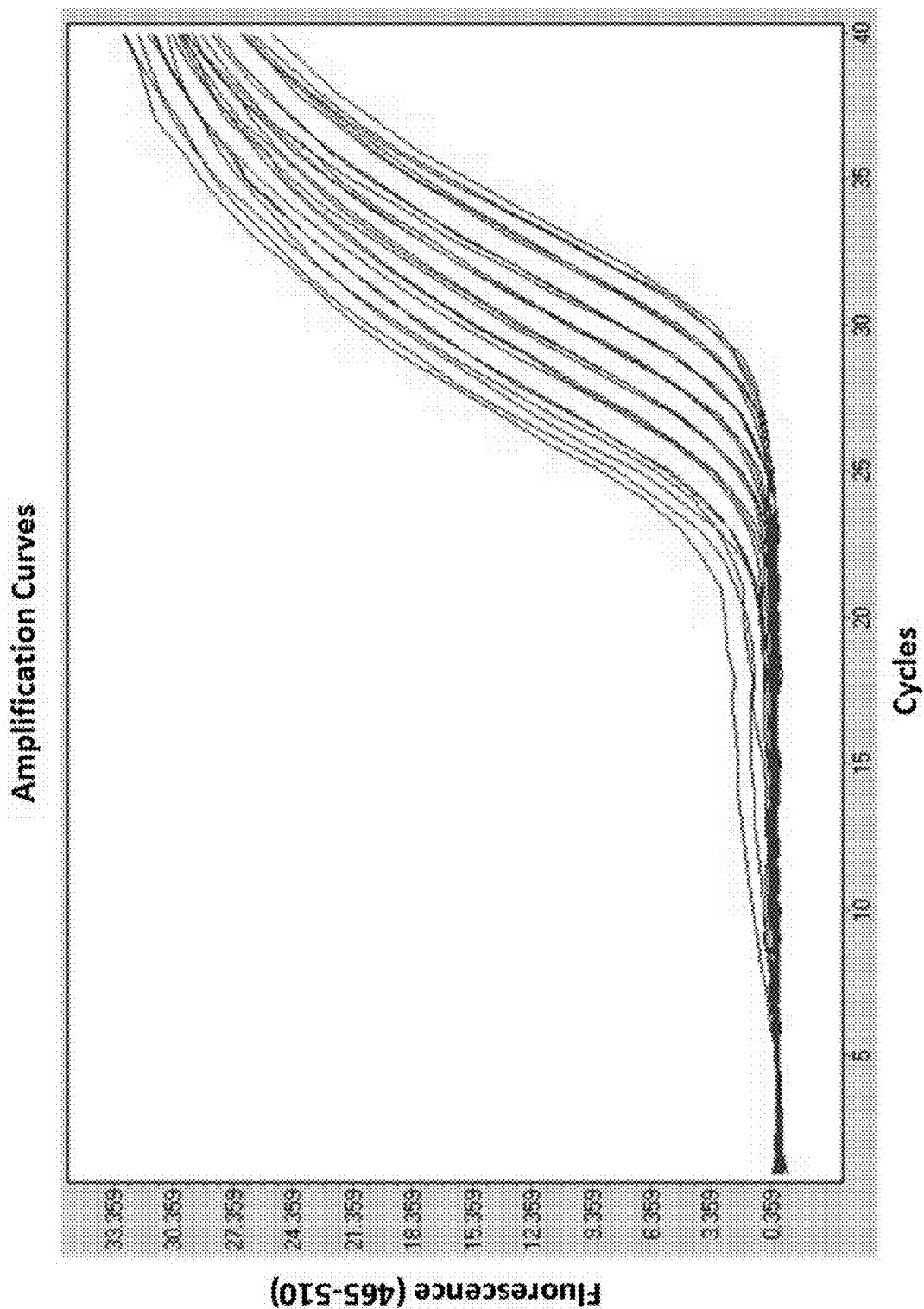
Figure 4C:
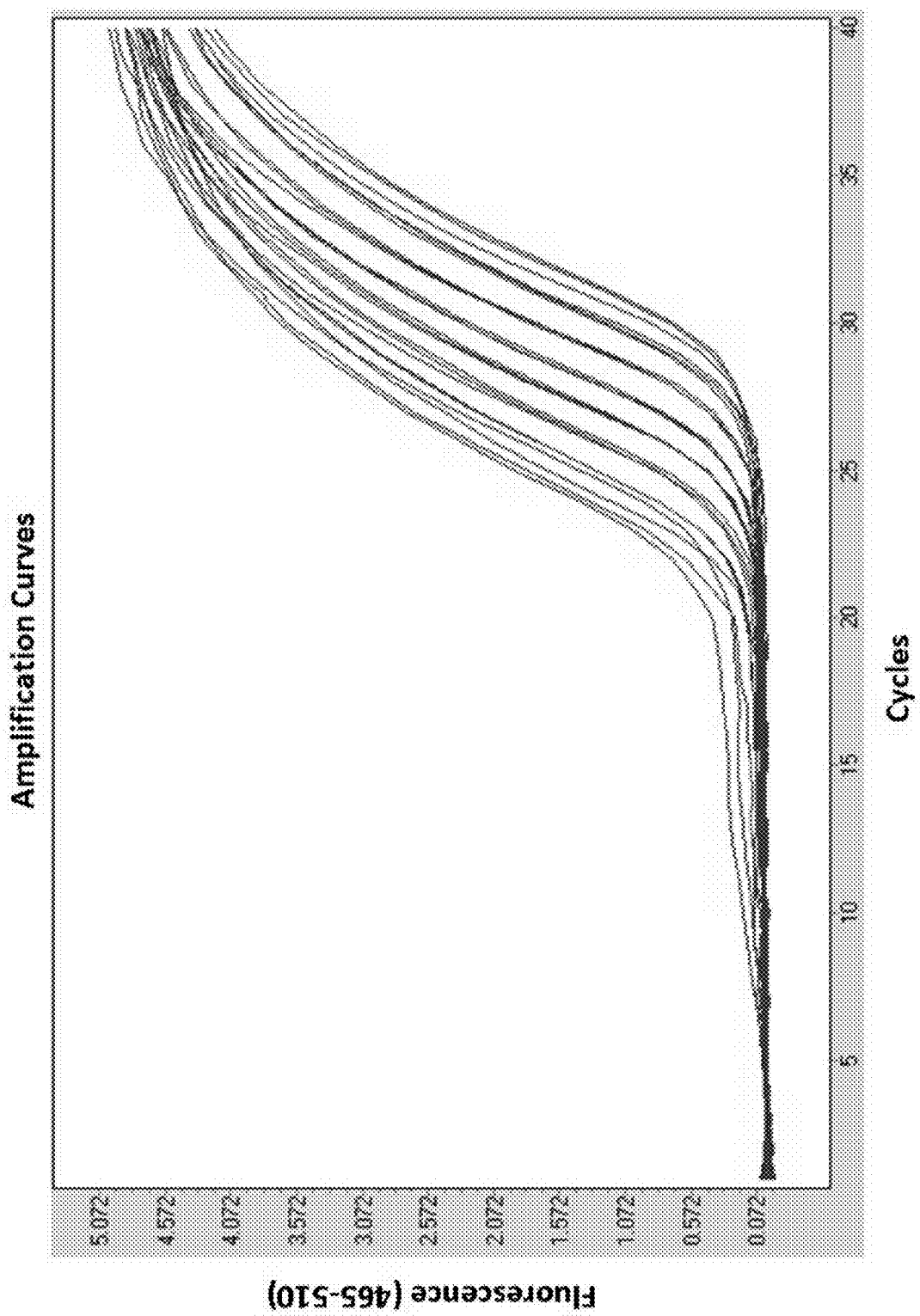

The disclosed triplex qPCR assay was carried out with varied concentrations of target DNA (mosaic M DNA). The linear regression lines of crossing point (Cp) (calculated by the Roche LC480 program by the second derivative method) vs. the log(concentration) of input DNA for the telomere, RNase P and β2-microglobulin targets, and the data are shown in FIG. 3A-FIG. 3C. An $R^2 > 0.999$ was achieved for each of the three targets at 0.0391 ng/μL to 5 ng/μL target DNA, i.e., a 128-fold range. Since 3 μL of target DNA was used in a 10 μL PCR reaction, this corresponds to a range of 0.13 ng/μL to 16.7 ng/μL of target DNA in the 3 μL volume added to the reaction. Thus, the assay can detect and quantify target DNA at least as low as 0.13 ng/μL, although it is possible that lower concentrations target DNA can be detected under the conditions of the disclosed triplex qPCR assay. The highest genomic DNA final reaction concentration used in this study was 5 ng/μL. It was observed that baseline of the amplification curves for the RNase P and β2-microglobulin targets are higher than the rest of the standard curve points at the highest genomic DNA concentrations (mosaic M DNA) used (see FIG. 4A-FIG. 4C).

Example 5—Assay Carried Out with Non-Template Controls

Figure 5A:
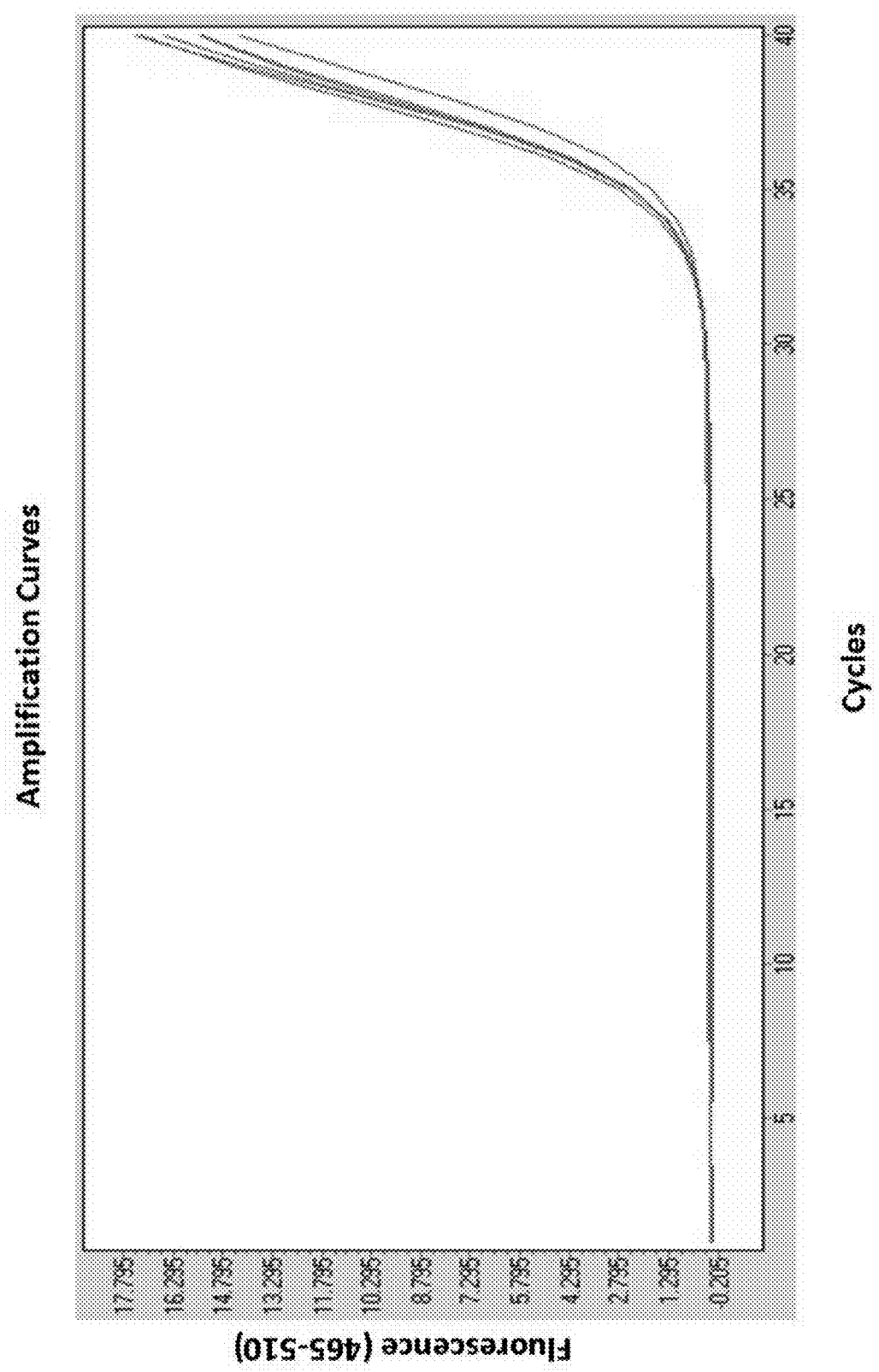
Figure 5B:
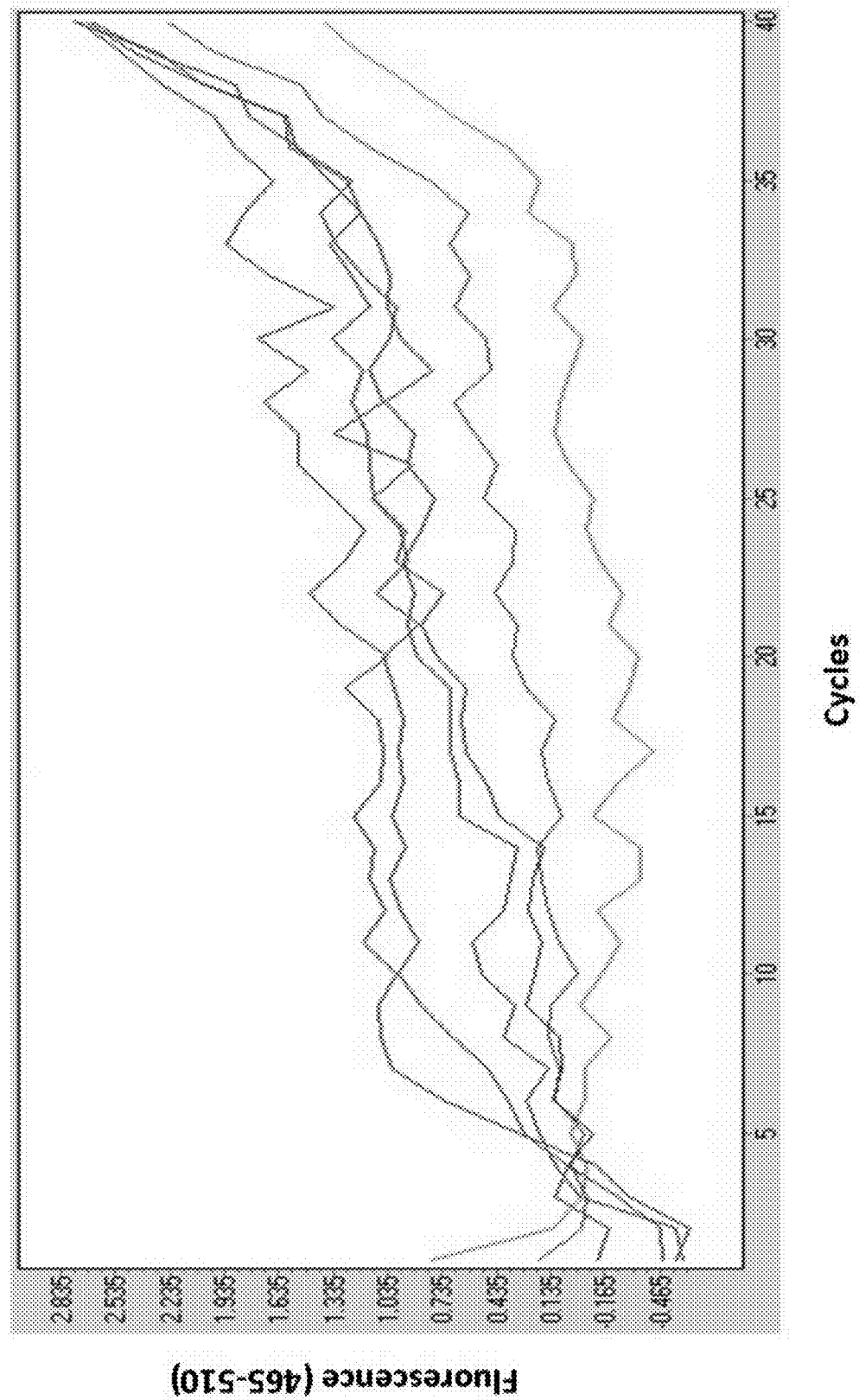

The disclosed triplex qPCR assay was carried out using nine non-template control ("NTC") samples. The experiment was carried out with the nine NTC samples in a single assay plate. The NTC Cp for the telomere and the RNase P targets were all greater than 35; whereas three of the 9 wells for B2M have an artifactual NTC Cp calling of 5, and the other 6 wells didn't have Cp calling. It should be noted that although the B2M wells had an artifactual Cp calling of 5, the data shown in FIG. 5C show minimal amplification was observed from the amplification curve. These data suggest that under the conditions of the disclosed triplex qPCR assay there was little or no risk of NTC signal interference with calculation of sample Cp values.

Example 6—PCR Efficiency

The PCR efficiencies of three quality control DNA samples, male mosaic reference DNA, and four patient DNA samples were obtained by carrying out the disclosed triplex qPCR assay using an 8-point, 2-fold serial dilution for each of the samples, with the highest concentration in the final PCR reaction as 3 ng/μL (see Table 7). The diluted DNA samples were run twice and the PCR efficiencies are summarized in Table 8. There is significant amount of variation in the PCR efficiency when the two runs are compared. Despite the difference in the PCR efficiencies an average CV of 3.4% for RNase P and 3.1% for β2M was obtained when the two runs were compared. Table 8 shows the CV values obtained for RNase P target, and Table 9 shows the CV values obtained for the β2-microglobulin target. The data in Tables 8 and 9 show that the CVs are higher at the lower concentrations target DNA. When the lowest concentration points were removed, the average CV decreased to 2.9% for RNase P and 2.5% for β2-microglobulin. Based on the CV values for β2-microglobulin, an optimal concentration in the final PCR reaction may be 0.5 ng/μL (between standard 3 and 4). Therefore, the normalized source DNA for patient samples should optimally be about 1.7 ng/μL.

TABLE 7

| Standard point | Final concentration in reaction(ng/μl) |
|---|---|
| Std1 | 3 |
| Std2 | 1.5 |
| Std3 | 0.75 |
| Std4 | 0.375 |
| Std5 | 0.1875 |
| Std6 | 0.09375 |
| Std7 | 0.04688 |
| Std8 | 0.02344 |

TABLE 8

| | Amplification Efficiencies* | | | | | |
|---|---|---|---|---|---|---|
| | T1 | T2 | R1 | R2 | B1 | B2 |
| QC1 | 89.6% | 90.0% | 96.0% | 88.9% | 95.6% | 94.9% |
| QC2 | 89.7% | 93.9% | 99.1% | 97.7% | 96.3% | 97.4% |
| QC3 | 87.2% | 88.4% | 94.9% | 94.9% | 88.2% | 94.8% |
| MM | 92.6% | 95.6% | 97.8% | 98.1% | 93.6% | 98.7% |
| PT1 | 94.6% | 97.7% | 94.1% | 94.4% | 92.3% | 94.8% |
| PT2 | 90.3% | 93.1% | 89.3% | 90.3% | 90.2% | 93.3% |
| PT3 | 87.8% | 93.1% | 94.1% | 93.3% | 90.6% | 94.3% |
| PT4 | 90.9% | 93.7% | 92.8% | 92.9% | 87.9% | 93.0% |

*T1 and T2 represent two independent reactions carried out using the Tel G modified and Tel C modified primers; R1 and R2 represent two independent reactions carried out using the RNase P primer; and B1 and B2 represent two independent reactions carried out using the β2-microglobulin primers.

TABLE 9

| | QC1 | QC2 | QC3 | PT1 | PT2 | PT3 | PT4 |
|---|---|---|---|---|---|---|---|
| Std1 | 1.9% | 1.2% | 2.8% | 1.9% | 1.9% | 4.6% | 2.6% |
| Std2 | 3.1% | 5.5% | 2.9% | 2.3% | 2.9% | 1.9% | 2.8% |
| Std3 | 1.5% | 1.7% | 5.4% | 1.9% | 1.6% | 2.1% | 2.8% |
| Std4 | 3.0% | 1.5% | 1.9% | 1.4% | 1.1% | 2.7% | 3.7% |
| Std5 | 3.4% | 3.9% | 2.9% | 4.1% | 1.4% | 5.1% | 3.3% |
| Std6 | 3.9% | 3.1% | 2.2% | 0.9% | 4.0% | 3.3% | 3.4% |
| Std7 | 3.0% | 3.8% | 4.0% | 5.1% | 3.0% | 2.7% | 6.1% |
| Std8 | 7.1% | 8.9% | 2.1% | 8.0% | 8.4% | 2.3% | 7.9% |

TABLE 10

| | QC1 | QC2 | QC3 | PT1 | PT2 | PT3 | PT4 |
|---|---|---|---|---|---|---|---|
| Std1 | 0.8% | 1.5% | 1.6% | 2.5% | 1.3% | 1.0% | 0.6% |
| Std2 | 1.8% | 1.4% | 1.6% | 1.7% | 2.3% | 0.9% | 1.4% |
| Std3 | 1.6% | 2.1% | 1.4% | 1.2% | 2.9% | 2.7% | 0.9% |
| Std4 | 1.7% | 1.4% | 1.5% | 1.3% | 2.1% | 1.6% | 2.6% |
| Std5 | 2.5% | 4.4% | 3.6% | 2.2% | 4.2% | 1.9% | 4.1% |
| Std6 | 1.9% | 2.8% | 1.9% | 2.6% | 5.4% | 1.0% | 2.8% |
| Std7 | 5.0% | 3.2% | 9.4% | 3.7% | 2.5% | 7.9% | 4.2% |
| Std8 | 11.3% | 4.4% | 10.3% | 5.0% | 6.0% | 7.7% | 4.9% |

Figure 7B:
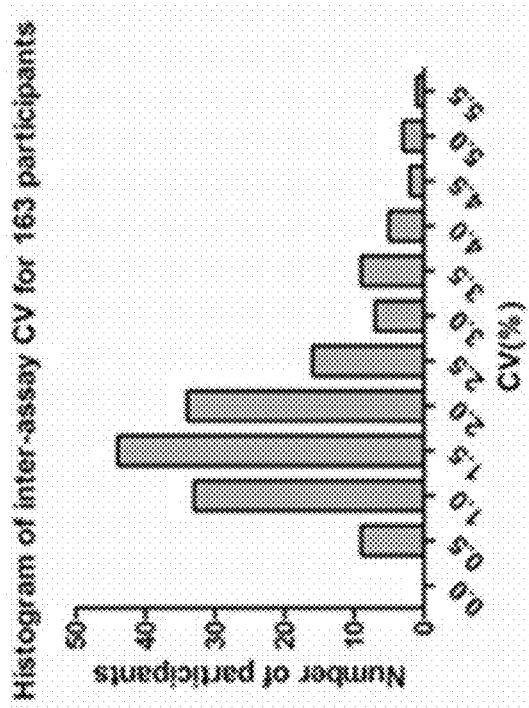
FIG. 7B shows a representative histogram of the inter-assay CV versus T:S ratios for the results obtained from the 163 research subject samples. The data used for determination of the inter-assay CV were obtained using the disclosed methods with the B2M-F, B2M-R, RNAP-F, RNAP-R, Tel G modified, and Tel C modified primers. The data suggest that inter-assay CV is not a function of T:S ratio, in other words, the inter-assay CV neither increases or decreases with telomere length.
Figure 7A:
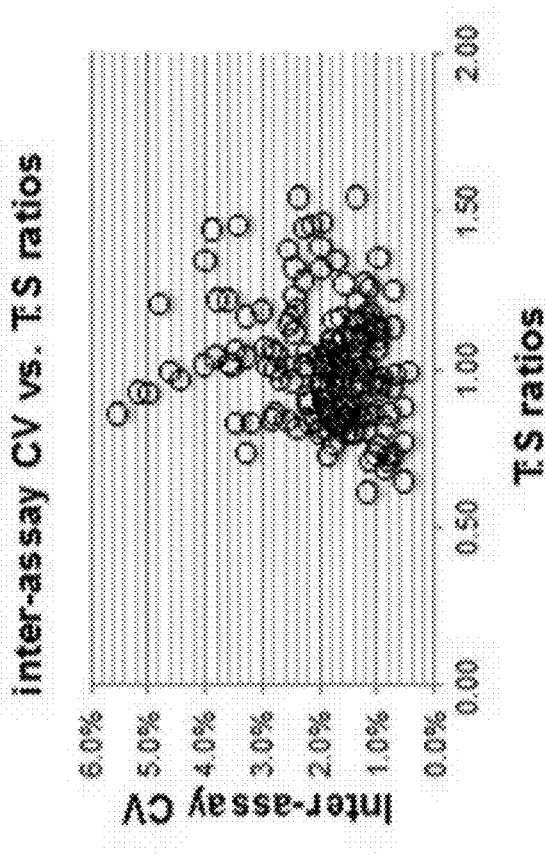
FIG. 7A shows a representative graph of the inter-assay CV values versus T/S ratios. The T/S ratios were determined using the disclosed methods with the B2M-F, B2M-R, RNAP-F, RNAP-R, Tel G modified, and Tel C modified primers in reactions carried out on 163 samples from healthy research participants. The data show that the median CV for plate-to-plate variation with the disclosed triplex qPCR assay is about 1.5%, which is significantly lower than that for the older versions of the monochrome or monochrome multiplex assays (typically in the 5% range or higher).

Example 7—T/S Determination in a Patient Population Using the Disclosed Triplex qPCR Assay Method The disclosed triplex qPCR assay method as described herein was used with 163 patient DNA samples from an asymptomatic population. The DNA samples were extracted from blood obtained from each patient. The results established a T/S ratio range of 0.61-1.55 in (FIG. 6A). The patient population examined had an age range of 21-78 years (mean 51 years), with a gender distribution of 82 females and 81 males. A strong correlation between T/S ratios and age was observed ($R^2=0.36$, see FIG. 6B). The disclosed triplex qPCR method displayed a very low inter-assay CV value (see FIG. 7A and FIG. 7B). For example, the mean inter-assay CV of these 163 samples is 1.9% even when the PCR assay plate was pipetted manually by a single individual. In contrast, it should be noted that typical inter-plate and inter-operator variability (CV values) with are in the 5-10% range when the assay was carried out as described by Cawthon (Cawthon, R. M., *Nucleic. Acids Res.*, 2002, 30(10):e47). In a recent publication by Martin-Ruiz, et al. (Int. J. Epidemiol. (2014) doi: 10.1093/ije/dyu191), the authors reported that inter and intra-batch CV values for qPCR within individual laboratories CV's ranged from 2.3% to 28%". The data obtained using the methods of the present invention demonstrate that the disclosed triplex qPCR assay provides much greater precision than previously described qPCR methods developed for telomere length determination, e.g., the method of Cawthon (Cawthon, R. M., *Nucleic. Acids Res.*, 2002, 30(10):e47). Moreover, the data described herein provide significantly improved CV values than the average CV values reported for batch variations by Martin-Ruiz, et al. (Int. J. Epidemiol. (2014) doi: 10.1093/ije/dyu191).

Example 8—Total Variability in the Disclosed Triplex qPCR Assay Method

Each of 9 patient samples was assayed in triplicate in a single assay carried out in a single 96-well plate by a three operators. The sample locations for the patient samples in each assay were as shown in Table 11. The T/S ratio was calculated for each of the three replicates which provided an estimate of the "within run" variance. The same plate arrangement was then repeated on five separate days, once in the morning and once in the evening, using 3 different operators, for a total of 10 plate repeats per the schedule shown in Table 12. Nine of the ten plates passed QC and were used for analysis.

TABLE 11

| | 1 | 2 | 3 | 4 | 5 | 6 | 7 | 8 | 9 | 10 | 11 | 12 |
|---|---|---|---|---|---|---|---|---|---|---|---|---|
| A | | APR_7 | | | | APR_7 | | | | | APR_7 | |
| B | APR_1 | APR_8 | | | APR_1 | APR_8 | | | | APR_1 | | |
| C | APR_2 | | | | | APR_9 | | | | APR_2 | APR_8 | |
| D | APR_3 | APR_9 | | | APR_2 | | | | | | APR_9 | |
| E | APR_4 | | | | APR_3 | | | | | APR_3 | | |

TABLE 11-continued

|   | 1 | 2 | 3 | 4 | 5 | 6 | 7 | 8 | 9 | 10 | 11 | 12 |
|---|---|---|---|---|---|---|---|---|---|----|----|----|
| F | APR_5 |   |   |   | APR_4 |   |   |   |   | APR_4 |   |   |
| G | APR_6 |   |   |   | APR_5 |   |   |   |   | APR_5 |   |   |
| H |   |   |   |   | APR_6 |   |   |   |   | APR_6 |   |   |

TABLE 12

|    | Day 1 | Day 2 | Day 3 | Day 4 | Day 5 |
|----|-------|-------|-------|-------|-------|
| AM | Operator 1 | Operator 3 | Operator 3 | Operator 1 | Operator 1 |
| PM | Operator 2 | Operator 2 | Operator 2 | Operator 3 | Operator 2 |

Figure 8A:
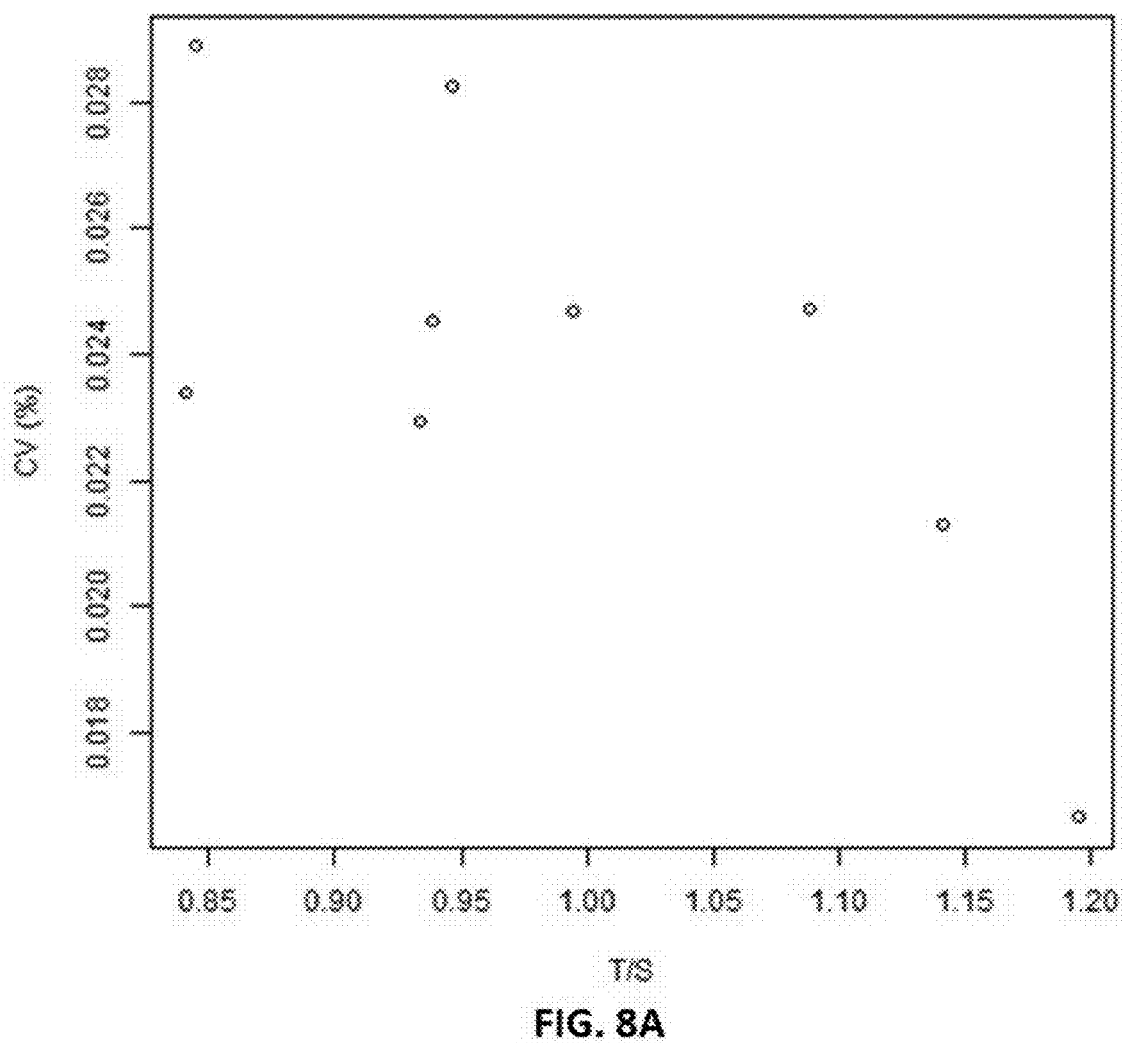
FIG. 8A shows the intra-assay CV estimates for T/S ratios obtained using 9 research subject samples analyzed in triplicate per day for experimental determination on each of five different days by three separate operators. The CV was calculated using a random effects model wherein the "sample run" was the random effect in the model. The T/S ratios were determined using the disclosed methods with the B2M-F, B2M-R, RNAP-F, RNAP-R, Tel G modified, and Tel C modified primers. The intra-assay CV (the coefficient of variation between technical replicates, i.e. theoretically identical samples) for the T:S ratio was 2-3%.
Figure 8B:
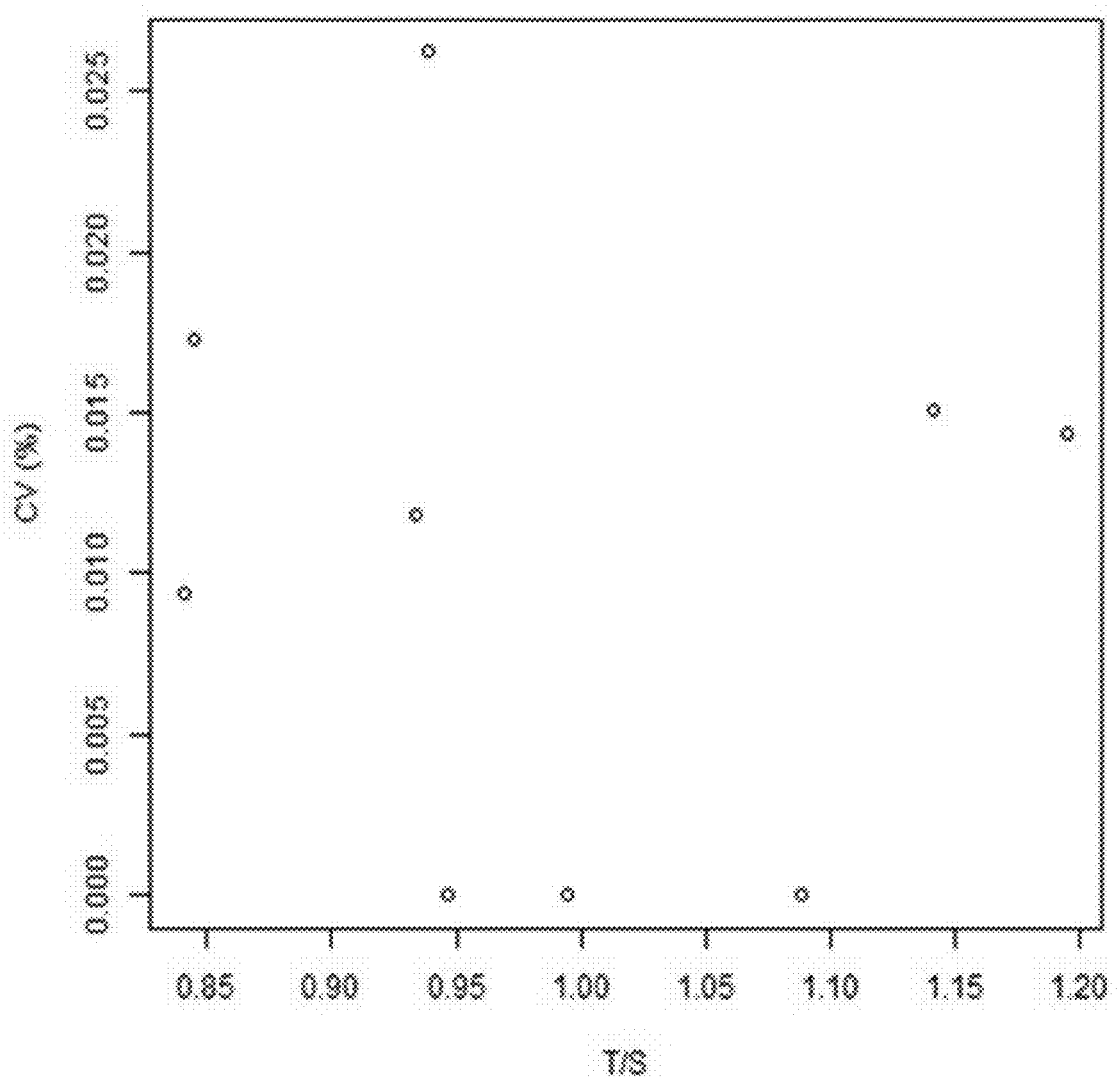
FIG. 8B shows the inter-assay CV estimates for T/S ratios (i.e. the plate-to-plate variation) obtained using 9 patient samples analyzed in triplicate per day for experimental determination on each of five different days by three separate operators. The CV was calculated using a random effects model wherein the "sample run" was the random effect in the model. The T/S ratios were determined using the disclosed methods with the B2M-F, B2M-R, RNAP-F, RNAP-R, Tel G modified, and Tel C modified primers. The data show a very low CV (roughly 0-2.5% for sample run variations on different days using 3 different operators over 5 different days). To our knowledge, this is the lowest inter-plate CV for ATL ever reported.
Figure 8C:
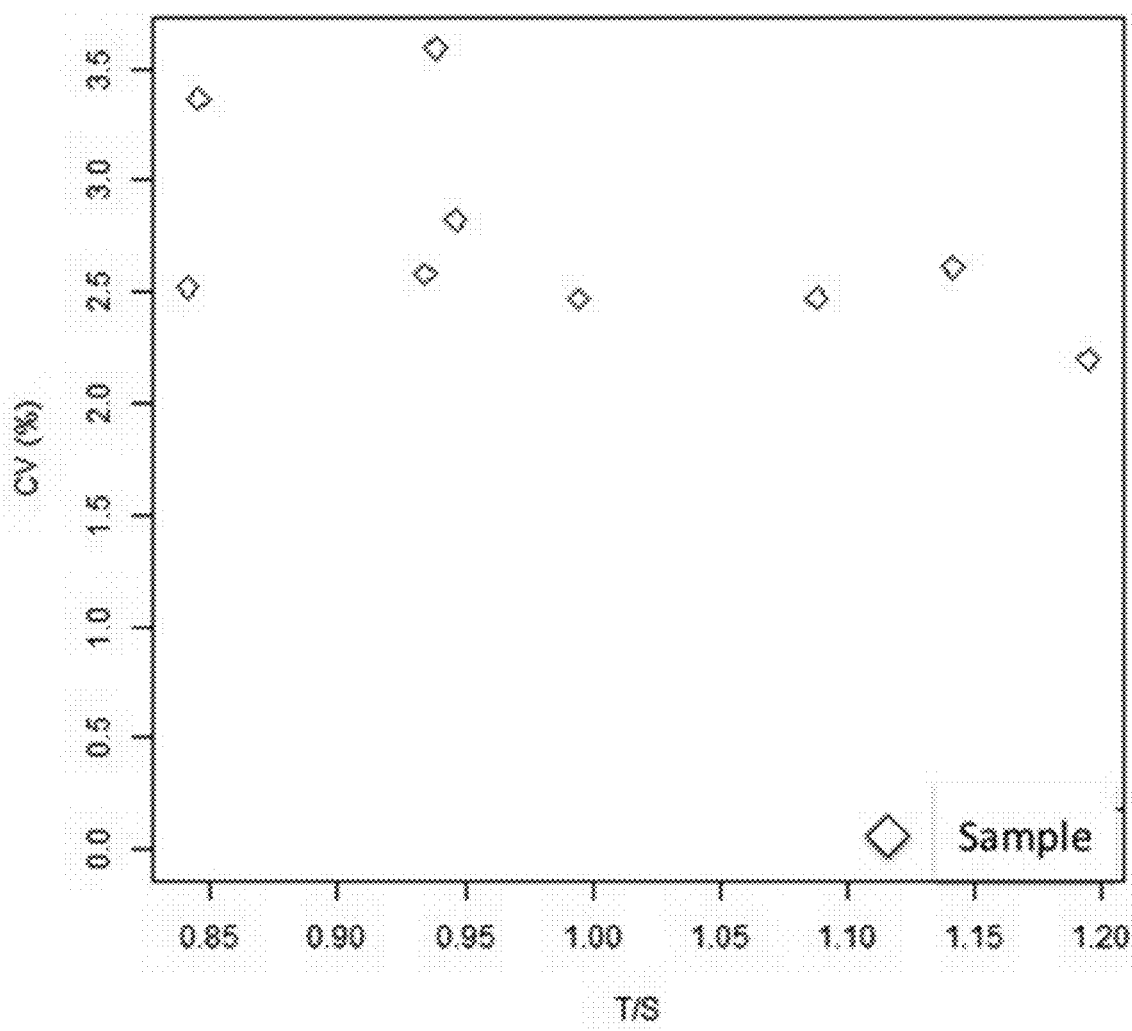
FIG. 8C shows the total CV estimates for T/S ratios obtained using the same 9 patient samples analyzed in triplicate per day for experimental determination on each of five different days by three separate operators. The CV was calculated using a random effects model wherein the "sample run" was the random effect in the model. The T/S ratios were determined using the disclosed methods with the B2M-F, B2M-R, RNAP-F, RNAP-R, Tel G modified, and Tel C modified primers. The data show that the whole-assay CV is in the 2-4% range.

The sample data from the multiple assays carried out as described above were analyzed using a random effects model with "run" being the random effect. Estimates of within, between and total run variability were obtained. The design of the study and data analysis follows the guidelines for evaluation of precision performance of quantitative assays, outlined in the CLSI (formerly NCCLS) guidelines. The intra, inter and total CV of the assay, across the range of T/S covered by the 9 samples was excellent (FIG. 8A-FIG. 8C). The intra and inter assay CVs ranged from close to zero to 2.9% while the total CV ranged from ~2.2% to 3.5%.

Example 9—E. coli Clone with Telomeric Sequence

PCR product was prepared by amplification of the target sequence from genomic DNA obtained from the bladder cancer cell line, UMUC-3. The PCR reaction used the primers Tel-4rp (SEQ ID NO.: 14; obtained from Integrated DNA Technologies, Inc., Coralville, Iowa, "IDT") and SUS SEQ ID NO.: 15; obtained from IDT; HPLC purified). The reaction was carried out under following conditions: 40 ng UMUC-3 genomic DNA, 1.5 mM $MgCl_2$, 500 nM SUS primer, 500 nM Tel-4rp, 300 µM dNTP (BioRad, Cat. No. 170-8874), 0.125 U/µl Platinum Taq (Invitrogen) in 50 µl reaction. The PCR cycles were as follows: 1 cycle at 94° C., 2 min; 35 cycles at 94° C., 15 sec, 65° C., 30 sec, 72° C., 5 min, and 1 cycle at 72° C., 20 min. The PCR product was purified by gel electrophoresis using a 0.8% E-gel (Cat No. G5018-08; Thermo Fisher Scientific Corporation, Carlsbad, Calif.) and the 0.8-1.2 kb size range products were isolated from the gel using the GeneClean Turbo Kit (Cat. No. 1102-200; MP Biomedicals, LLC, Santa Ana, Calif.). The PCR product was then cloned into the TA cloning vector (TOPO® TA Cloning® Kit for Subcloning, Cat. No. K4510-20; Thermo Fisher Scientific Corporation, Carlsbad, Calif.). The vector with cloned PCR product was transformed into transformation competent E. coli cells, and following growth overnight, selected colonies were picked from the transformation agar plate. The DNA sequence cloned into the plasmid was determined for the selected colonies. One clone, Y3 (SEQ ID NO.: 12), contained a 135 bp telomeric sequence fragment. This clone was chosen to be the source of the absolute telomere length reference.

Example 10—Preparation of an Absolute Telomere Reference

DNA obtained from rolling circle amplification ("RCA") of the Y3 clone described above was used as the template for PCR amplification. Two rounds of PCR amplification were used to obtain the absolute telomere reference. In the first round of PCR amplification, M13 forward (SEQ ID NO.: 16) and M13 reverse primers (SEQ ID NO.: 17) were used in a reaction with 1 µl of the RCA product material. The PCR amplification product, Y3-M13 PCR product, was purified with the QIAquick PCR purification kit (Cat. No. 28104; QIAGEN Inc., Valencia, Calif.), and then quantified by nanodrop UV-Vis spectrophotometry (NanoDrop 8000, Thermo Fisher Scientific). In the second round of PCR amplification, M13 forward primer (SEQ ID NO.: 16) and TeloAnchor primer (SEQ ID NO.: 18) were used with 5 ng of the previously purified Y3-M13 PCR product. The product of the second round of PCR amplification, Y3-Telotail PCR product, was purified by the QIAquick PCR purification kit and quantified by Picogreen assay (Quant-iT™ PicoGreen® dsDNA reagent, Cat. No. P11495, Thermo Fisher Scientific, Inc.). The Y3-Telotail PCR product was used as the absolute telomere reference DNA.

Example 11—Southern Blot Analysis

Southern blot analysis was performed according to published protocols (Masayuki K., et al. Nature Protocols 5, 1596-1607 (2010) with minor modifications. Briefly, genomic DNA was extracted from unselected blood samples obtained from anonymous donors at the Stanford Blood center and was isolated as high molecular weight DNA. The genomic DNA 3-5 µg) was digested by incubation with 20 U of HphI (Cat. No. R0158S, New England Biolabs Inc., Ipswich, Mass.) and 20 U of MnlI (Cat. No. R0163S, New England Biolabs Inc.) at 37° C. for 6 hr or overnight (≥16 hr) in a reaction volume of 40 µL. The digested genomic DNA was separated by agarose gel electrophoresis using a 0.5% agarose gel in presence of 0.5×TBE with electrophoresis carried out at 40 VDC for 16 hr in a BioRad Sub-Cell GT gel apparatus. DIG-labeled size markers III (Cat. No. 11218603910, Roche Applied Science, Indianapolis, Ind.) and VII (Cat. No. 11669940910, Roche Applied Science) were used. The DNA in the gel was depurinated (0.25 M HCl), denatured (0.5 M NaOH, 1.5 M NaCl) and transferred to a TurboBlotter™ system (Cat. No. 10416316, GE Healthcare Bio-Sciences Corp., Piscataway, N.J.). Transfer was onto a Nytran SPC membrane in the presence of 20×SSC transfer buffer and carried out from 4 hr to overnight (about 16 hr). The DNA was crosslinked to the membrane by two treatments of the membrane with DNA at 120 mJ $cm^{-2}$ in a Stratagene Crosslinker and prehybridized in DIG Easy Hyb (Cat. No. 11603558001, Roche Applied Science) at 37° C. for 2 hr, followed by hybridization with 2.5 pmol of DIG labeled TeloProbe (SEQ ID NO.: 19; obtained from IDT and HPLC purified) per mL Easy Hyb solution (a total of 30 pmol probe, or 6.6 µL for 12 mL, was used) at 37° C. overnight. Signal was detected by Anti-Digoxigenin-AP (Cat. No. 1109327491, Roche Applied Science) and images were captured using a BioRad ChemiDoc Imager.

Example 12—Telomere Restriction Fragment Length Quantification

TRF was quantified using the following procedure using ImageJ software (see imagej.nih.gov/ij).

To Generate the Standard Curve of Converting Mobility to Molecular Weight.

In the ImageJ program, a line was drawn from the top of the well to the bottom, then select the menu option: Select Analyze→Plot Profile, Select "List" and then in the new window, "File→Save As" and save the molecular ladder's profile. Open the profile in Excel, graph the Distance vs. Intensity. Manually find the distance/intensity corresponding to each of the peak. Graph a scatterplot of Distance vs. Log (molecular Weight) for the peaks and generate a linear formula Log(MW)=A*Distance+B.

Generation of the Telomere Restriction Fragment (TRF) Length of Each Lane.

As above, in ImageJ, a profile was generated for each of the lanes and Excel was used to convert the Distance to Log(MW) for each of the data points by applying the formula above, and transformed the Log(MW) data to MW data. We then obtained the intensity/MW data by diving the Intensity (from the Image J profile) data by the MW data. The 20 kb and 1 kb positions were identified based on the MW data set and used to calculate the TRF length in kbp by the following formula using the data points from 20 kb to 1 kb: TRF=SUM(Intensity)/SUM(Intensity/MW).

Example 13—PCR Efficiency of aTL Standard Curve

Figure 9:
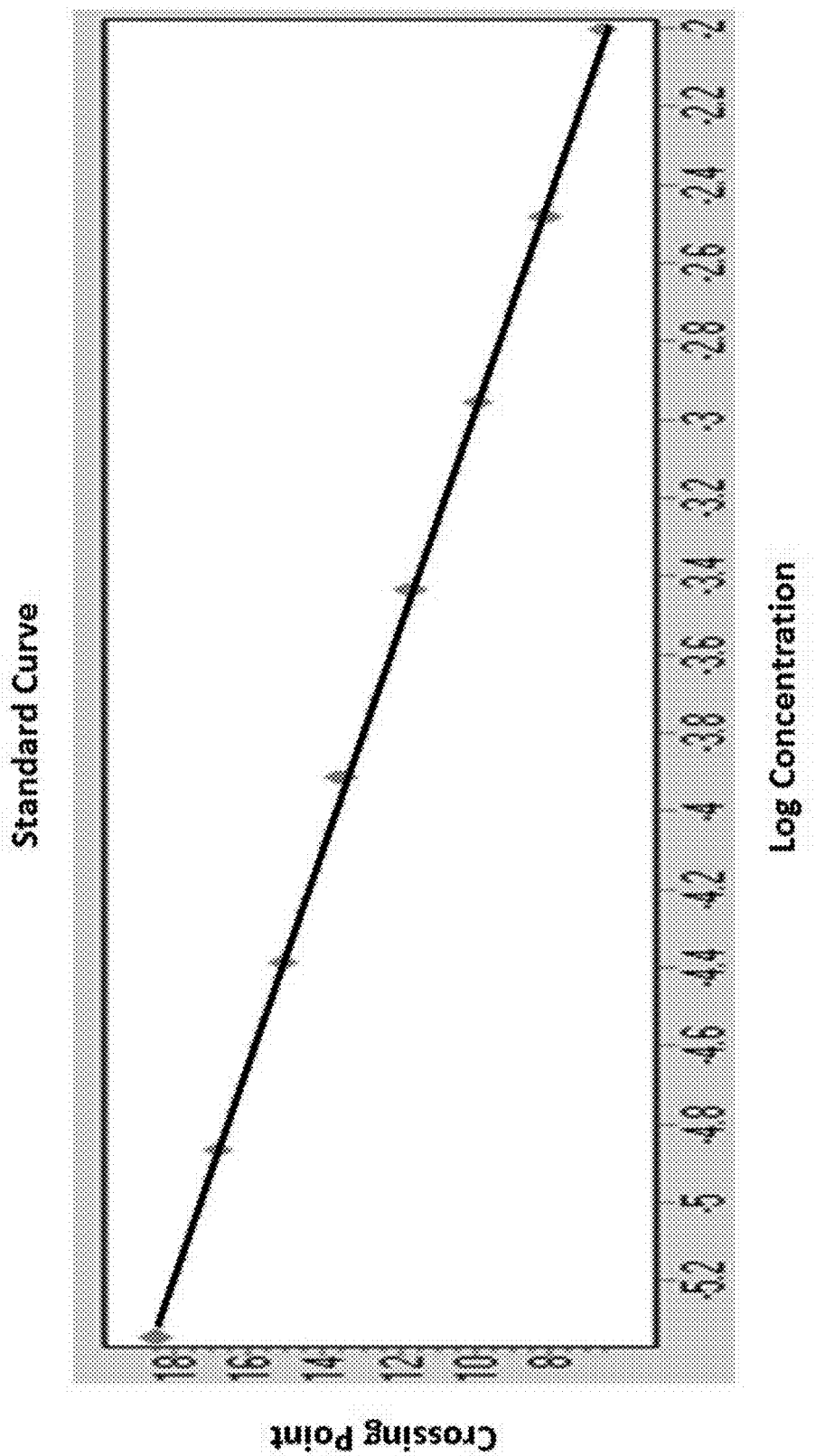
FIG. 9 shows the 8-point standard curve with 3-fold serial dilution points of Y3-plasmid clone (a plasmid containing a 286 amplicon containing the 135 bp of telomeric DNA (SEQ ID NO:12), Y3 Clone). qPCR efficiency based on slope of the standard curve is 91.6%+/−6% standard deviation (mean of 4 measurements). R2 linearity was greater than 0.99.

A 1 ng/µl stock solution (measured by PicoGreen method) of the Y3-Telotail PCR product was prepared by diluting the purified Y3-Telotail PCR product in DNA suspension buffer (10 mM Tris-HCl, 0.1 mM EDTA) and stored at −20° C. in 20 µL aliquots. A 1:50 dilution was made with DNA suspension buffer to prepare the Y3-Telotail PCR product at 20 pg/µL. A 3-fold serial dilution was further made to create an 8-point standard curve, with 20 pg/µL as the highest concentration. The T/S ratios for the 8-point serial dilutions of Y3-Telotail PCR product were determined using the previously described qPCR assay of Cawthon (Cawthon, R. M., *Nucleic. Acids Res.*, 2002, 30(10):e47). PCR efficiency was calculated using the Roche LC480 software with the absolute quantification method and second derivative method. The average efficiency was 91.6% (STDEV=6%). This was slightly higher than the PCR efficiency of the reference standard Mosaic M genomic DNA (average 88.4%). All four runs had linearity of $R^2$ greater than 0.99 (Table 13) A typical standard curve is shown in FIG. 9.

TABLE 13

| Run Set | Individual Run | Efficiency (%) | Linearity -$R^2$ |
| --- | --- | --- | --- |
| Run Set A | 1 | 90.2 | 0.9996 |
|  | 2 | 89.7 | 0.9998 |
| Run Set B | 1 | 100.1 | 0.9953 |
|  | 2 | 86.2 | 0.996 |

Example 14—Calculation of aTL in a Test Sample

A. Conversion of Y3-Telotail PCR DNA Concentration to Telomere Sequence Concentration.

The Y3-Telotail PCR product is a 268 bp long, double stranded amplicon, wherein 135 bp of the amplicon are perfect telomere repeats (TTAGGG:CCCTAA). The molecular weight ("MW") of this amplicon is 165477.2, and the weight of one molecule of amplicon is the MW divided by Avogadro's number. Thus, the weight of the Y3-Telotail PCR product standard is:

$$165477.2/6.02 \times 10^{23} = 2.74879 \times 10^{-19} \text{ g}.$$

The highest concentration of the standard (STD1) used in PCR reaction was 2 pg/µL DNA based on Picogreen measurement. Therefore, the calculation to provide the number of molecules DNA per µL in STD1 is as follows:

$$2 \times 10^{-12}/2.74879 \times 10^{-19} = 7275929.$$

Thus, multiplying the above by 135 yields the result that there are 982250 kb perfect telomere sequence per µL in STD1. The equation to convert telomere concentration calculated using the Y3 clone standard to perfect telomere sequence concentration (kb per µl):

$$\text{telomere concentration}\left(\frac{ng}{ul}\right) \times 982250 \ kb(\text{Value } A).$$

B. Calculation of the Genome Copy Number Concentration Using Human Beta-Globin Concentration.

The weight of one haploid human genome molecule is $3.59 \times 10^{-3}$ ng. The human beta-globin concentration is one measure of a single copy gene in the human genome. The genome copy number concentration (copy number per µL) per diploid for a single copy gene such as beta-globin can then be calculated as follows:

$$\text{concentration}(ng/uL)/(0.00359 \times 2)(\text{Value } B).$$

C. Calculation of Absolute Telomere Length

The absolute telomere sequence per genome (in kb per genome) is equal to the perfect telomere sequence concentration per genome copy number concentration, which in turn is equal to the calculation:

Value $A$/Value $B$, where the values are calculated as described herein above. Thus, aTL on each end of chromosome (in kb), is calculated as follows:

(Value $A$/Value $B$)/92.

Example 15—Correlation of T/S Values and aTL

Figure 10:
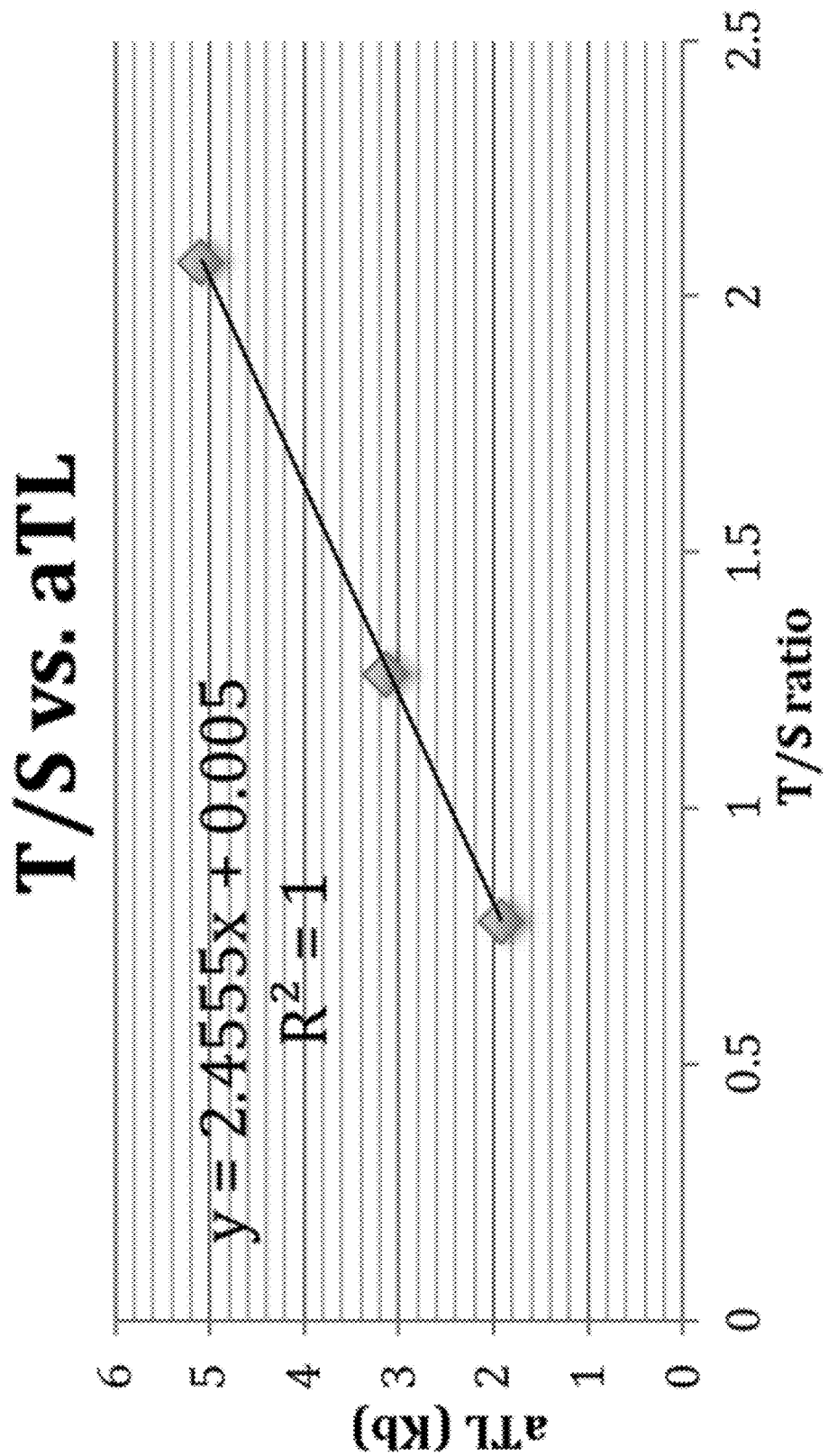
FIG. 10 shows the average telomere length (in kilobase pairs, "kbp"), determined using the Y3-plasmid clone as a standard and the disclosed triplex qPCR assay described herein, plotted as a function of T/S ratio. The slope of the regression line is 2.46, indicating that one T:S unit represents 2.46 kbp based with this methodology. The three data points were from analysis of 3 quality control samples representing low, medium, and high telomere length.

T/S ratios were determined using the methods described herein and compared to aTL values derived using the calculations described herein above. The comparison of three QC samples showed that the values are highly correlated with $R^2$ of 0.99998 (FIG. 10). Based on these data, the following formula was derived:

$$kbp = 2.4555 * (T/S) + 0.005$$

In addition, a series of genomic DNA derived from the UMUC-3 bladder cancer cell line infected with the gene for the RNA component of telomerase hTER were used to compare T/S ratios and aTL. Similar results were obtained and the following formula was derived for these data:

$$kbp = 2.589 * (T/S) - 0.074$$

Data for the correlation of T/S and aTL for QC samples from two independent runs using freshly prepared Y3 standards are shown below in Table 14.

TABLE 14

| Run | Sample | aTL (kb) | T/S Ratio | Average aTL (kb) | Average T/S |
|---|---|---|---|---|---|
| 1 | QC1 | 2.0271 | 0.7950 | 1.9200 | 0.7819 |
|   | QC2 | 3.3204 | 1.3221 | 3.1199 | 1.2653 |
|   | QC3 | 5.4852 | 2.1279 | 5.0825 | 2.0690 |
| 2 | QC1 | 1.8128 | 0.7688 | — | — |
|   | QC2 | 2.9195 | 1.2085 | — | — |
|   | QC3 | 4.6798 | 2.0101 | — | — |

Example 16—Correlation of T/S and aTL with UMUC3-hTER Series

Figure 11:
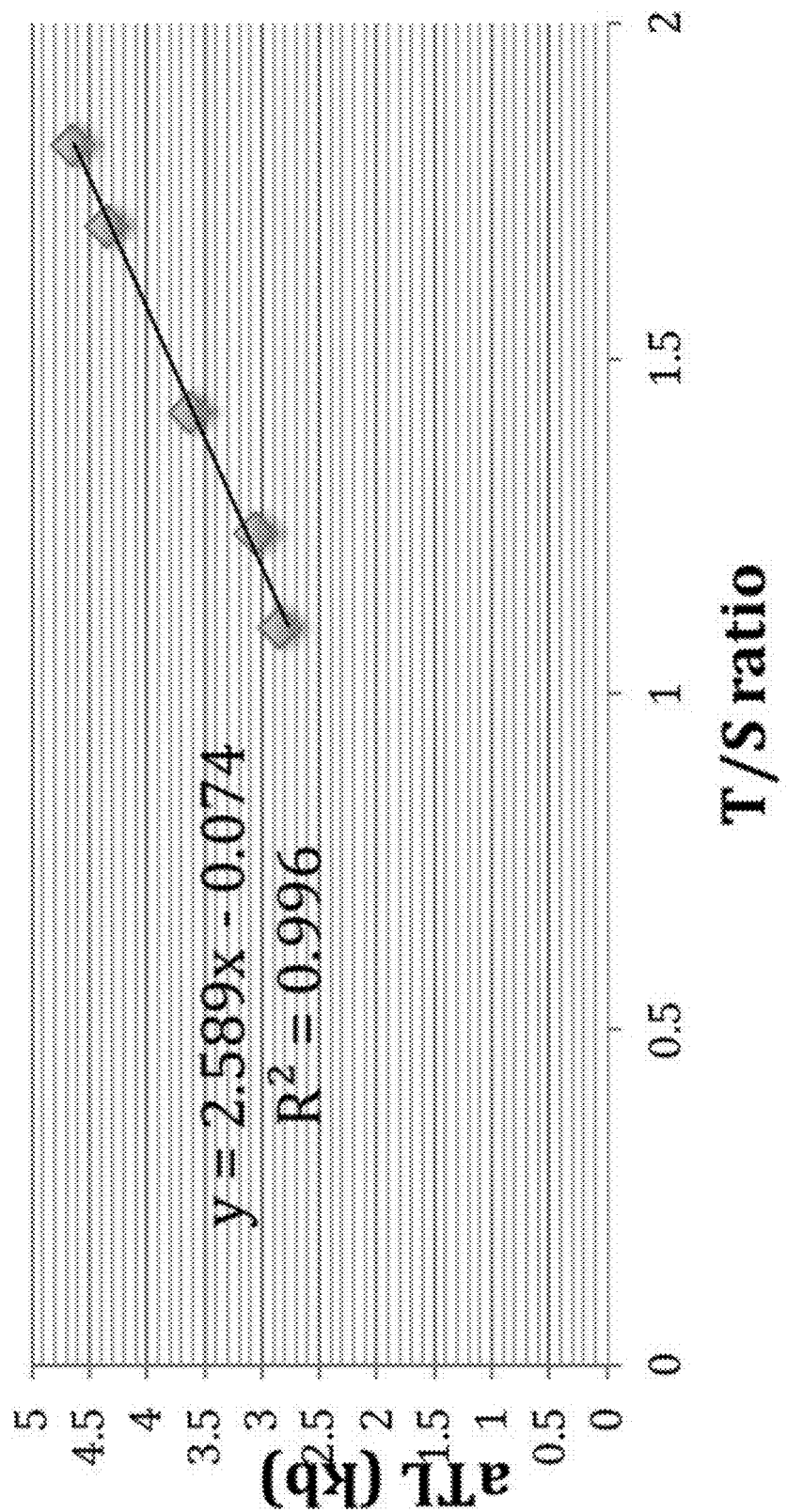
FIG. 11 shows the average telomere length (in kbp) plotted as a function of T/S ratio for 5 samples derived from a single cell line (a UMUC-3 bladder cancer line) which underwent telomere extensions by transfection of the cell line with the RNA subunit of telomerase (hTER). The average telomere length was determined using the disclosed triplex qPCR assay described herein. Telomere length increased from an initial value of approximately 2.8 kbp to 4.6 kbp, with data collected at baseline and 4 additional points during cell culture. The slope of the regression line is 2.59, indicating that one T:S unit represents 2.59 kbp based on this methodology.
Figure 12:
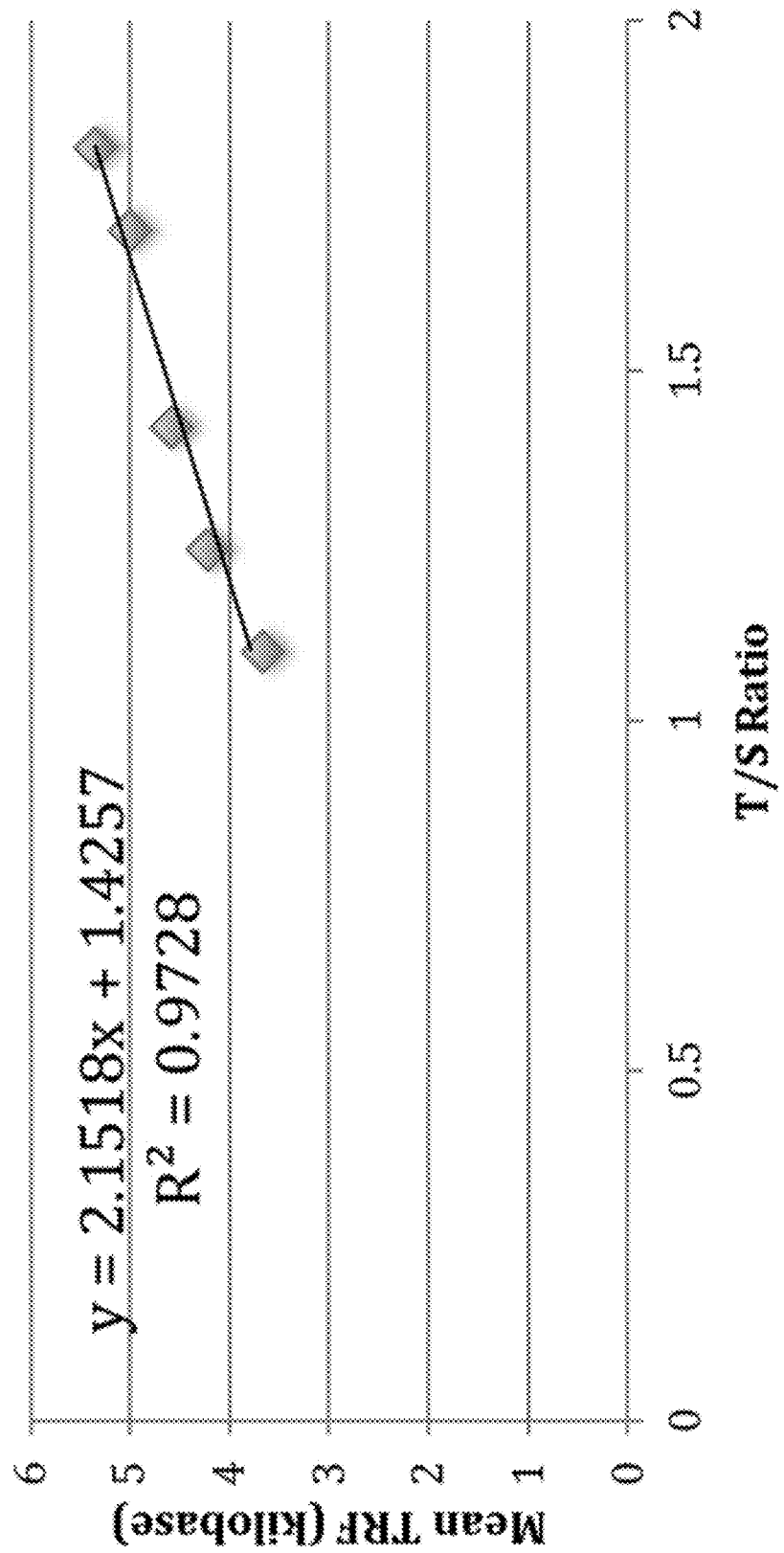
FIG. 12 shows average telomere length (in kbp), determined using the Southern Blot methodology, plotted as a function of T:S ratio. Based on this comparison, with a regression line slope of 2.15, one T:S unit represents 2.15 kbp. The samples for this comparison are identical to those used for FIG. 11.

The relationship between telomere length in kbp and T/S ratio (i.e., determining kbp per T/S units) was further assessed using a cell line (UMUC3) that was transduced with RNA component (TER) of telomerase, thus increasing telomerase activity and adding TTAGGG repeats to the ends of chromosomes. This cell line was named (UMUC3-TER). The length of telomeres in UMUC3-TER increased over time as the cells expanded in culture. T/S was determined using the assay described by Cawthon (Cawthon, R. M., *Nucleic. Acids Res.*, 2002, 30(10):e47). For each data point in FIG. 11, the y-axis represents the average terminal restriction fragment length (TRF) in kbp, determined as described herein, and the x-axis represents the measured T/S ratio of the DNA sample. Since telomerase only adds telomeric DNA to the ends of chromosome, the slope of the curve is a direct measure of telomeric DNA per T/S units: which from this experiment yields 2.45 kbp per T/S unit.

Example 17—Comparison of T/S to TRF by Southern Blot Analysis

As an third independent method of verifying the absolute telomere length calculation, telomere length of the same UMUC3-hTER series was measured using Southern blot analysis. Genomic DNA was digested with HphI and MnlI, run on a 0.5% gel and probed with an oligo comprising four telomeric repeats. To calculate telomeric restriction fragment, the formula originally proposed by Harley et al (Nature (1990) 345(6274):458-60) was used. This formula was also used by Cawthon et al. to compare the T/S ratios and TRF (Cawthon, R. M., *Nucleic. Acids Res.*, 2002, 30(10):e47). Comparison of T/S ratios using the assay described by Cawthon (Cawthon, R. M., *Nucleic. Acids Res.*, 2002, 30(10):e47) and TRF results yielded the following equation:

$$TRF = 2.1518*(T/S) + 1.4257 (R^2 = 0.97283).$$

The Y-intercept in this equation represents the average length of the subtelomeric region (Cawthon, R. M., *Nucleic. Acids Res.*, 2002, 30(10):e47), and the slope represents the factor for conversion of T/S ratios to bp. Thus, in this assay:

$$kbp = 2.1518*(T/S),$$

which provides a conversion factor of 2.15 kbp per T/S unit.

A similar methodology was used with samples of genomic DNA derived from the human lung fibroblast IMR90. Farzaneh-Far R, et al. (see Farazaneh-Far, R., et al. (2010) *PLoS ONE* 5(1): e6612. doi:10.1371/journal.pone.0008612) reported that:

$$TRF = 2.413*(T/S) + 3.274.$$

Thus, using the above formula, there are 2.41 kbp per T'S units, that is:

$$kbp = 2.413*(T/S).$$

This is very similar to the conversion factor above. Without wishing to be bound by a particular theory, it is possible that the difference in the Y intercept (subtelomeric region length) is due to the fact that in Lin et al., RsaI and HinfI were used to digest genomic DNA. HphI and MnlI (used in this report) are known to cut closer to the telomeric region compared to RsaI and HinfI. In addition, without wishing to be bound by a particular theory, two different cell lines were used in the studies described herein and in Farzaneh-Far R, et al. (see Farazaneh-Far, R., et al., (2010) PLoS ONE 5(1): e8612. doi:10.1371/journal.pone.0008612). Thus, it is possible that these cell lines have different subtelomeric length.

Example 18—Aggregated aTL Conversion Factor

In summary, the aggregated telomere length conversion factor to convert the T/S ratio to bp, the data in Table 15 are used. The average for the conversion factor from the four results (from four distinct methods) in Table 15 is 2.4 kbp per T/S unit, with a standard deviation of 0.19 for the four estimates.

TABLE 15

| Y3 aTL standard* | UMUC3-hTER series** | Cawthon† | Lin et al.‡ |
|---|---|---|---|
| 2.46 | 2.59 | 2.14 | 2.41 |

*Comparison of T/S ratios and aTL using three QC samples as described herein.
**Comparison of T/S ratios and aTL using UMUC3-hTER samples as described herein.
†Based on the data from Cawthon, R. M., *Nucleic Acids Res.*, 2009, 37(3):e21.
‡Based on data from Farzaneh-Far R, et al. (see Farazaneh-Far, R., et al. (2010) PLoS ONE 5(1): e8612. doi: 10.1371/journal.pone.0008612).

Example 19—Primer Impact on Quantitation of Canonical Telomere Sequences

"Variant sequence" is a term that refers to sequences of DNA frequently found within the sub-telomeric regions of DNA, but which are not considered true telomeric sequences. True telomere repeat sequences consist of blocks of CCCTAA:TTAGGG, while variant sequences can contain blocks of "degenerate" telomere-like sequences. One challenge for any method of telomere length measurement is differentiating between the "true" or canonical telomere and a series of repeats that vary from the canonical repeats by a small number of base pairs, e.g. a 1-3 base-pair variance from the canonical telomere sequence. Specific examples of such variant or degenerate sequences include TGAGGG, TCAGGG, TTGGGG, TTCGGG etc.

Experiments were carried out to compare amplification of three different templates representing canonical or degenerate target sequence repeats which were 90 nucleotides in length (synthetic "ultramers"). The studies were carried out using equimolar concentrations of the three different templates in order to provide data showing enhanced specificity of the disclosed primers for the canonical telomere repeats compared to a prior standard that is frequently used, i.e. the primers described by Cawthon (Cawthon, R. M., *Nucleic. Acids Res.*, 2002, 30(10):e47). The synthetic ultramers used are shown below in Table 16.

TABLE 16

| SEQ ID NO. | Ultramer | Sequence |
|---|---|---|
| 28 | Tel-repeat/telomere | (CCCTAA)$_{15}$ |
| 29 | G-rich variant/degenerate1 | (CCCTCA)$_{15}$ |
| 30 | C-rich variant/degenerate2 | (CCCTGA)$_{15}$ |

The assay was carried out using the disclosed triplex qPCR assay described herein above (see Example 1) with either the Cawthon primers, TeloTest Tel 1b and Tel 2b primers (SEQ ID NOs: 20 and 21, respectively), or using the Tel G modified and Tel C modified primers (SEQ ID NOs: 1 and 2, respectively). In the figures, these assay conditions are referred to, respectively, as "Triplex TT" or "ATL T."

Figure 13A:
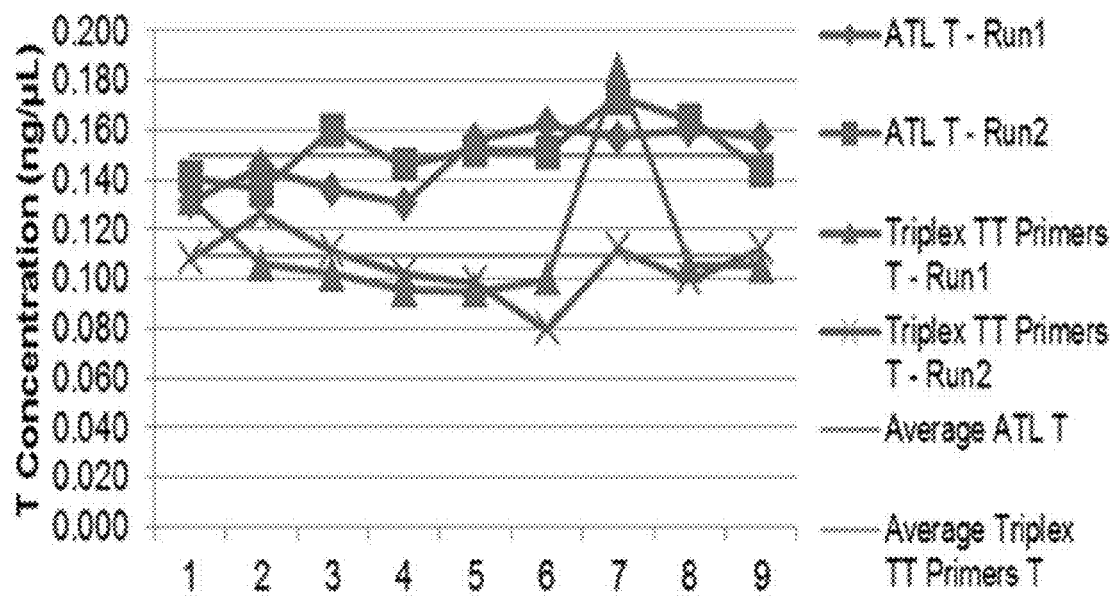
FIGS. 13A-13D show data comparing amplification using the disclosed triplex qPCR assay, described herein, of a canonical telomere repeat, $(CCCTAA)_{15}$, with either the Tel 1b and Tel 2b primers (SEQ ID NOs: 20 and 21, respectively) or the using the Tel G modified and Tel C modified primers (SEQ ID NOs: 1 and 2, respectively). Reactions containing the Tel 1b and Tel 2b primers are indicated with "TT" in the figures, and reactions containing the Tel G modified and Tel C modified primers are indicated with "ATL" in the figures.
Figure 13B:
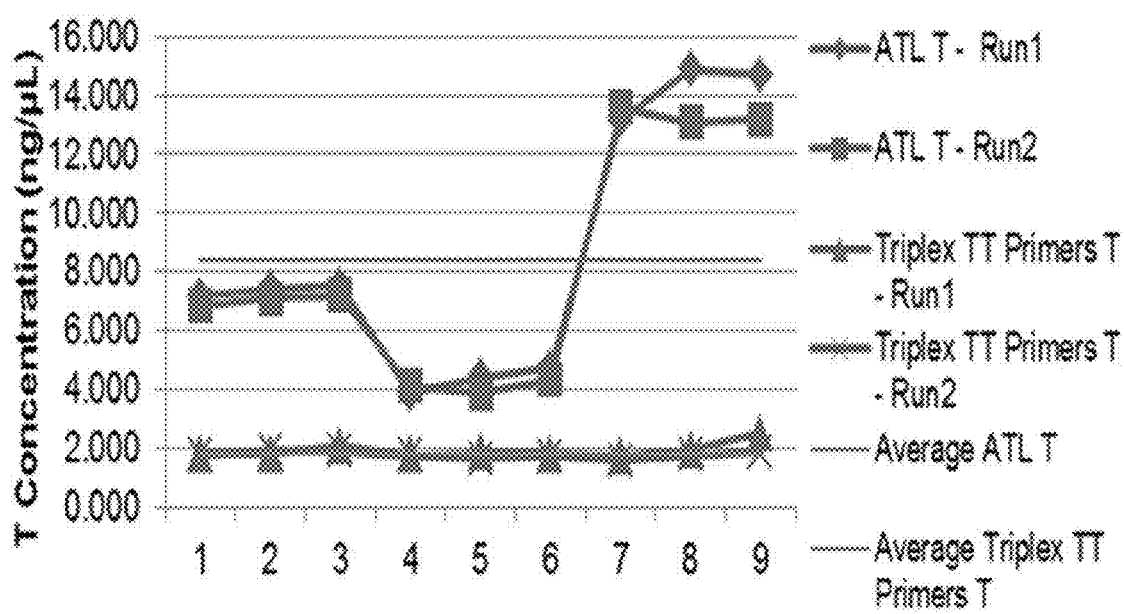
Figure 13C:
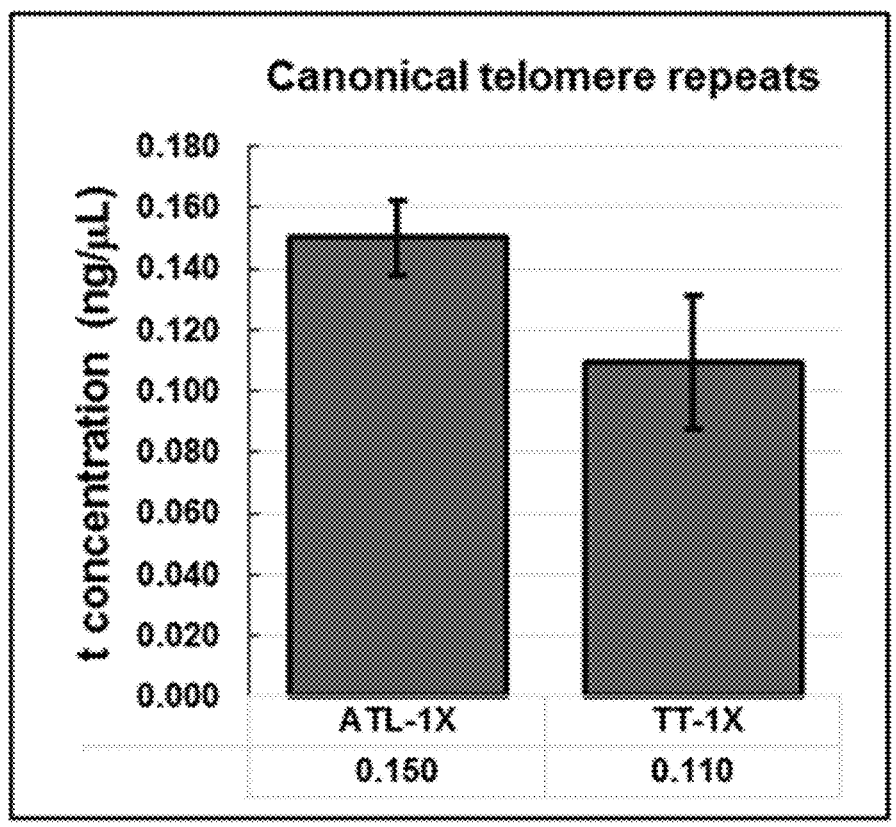
Figure 13D:
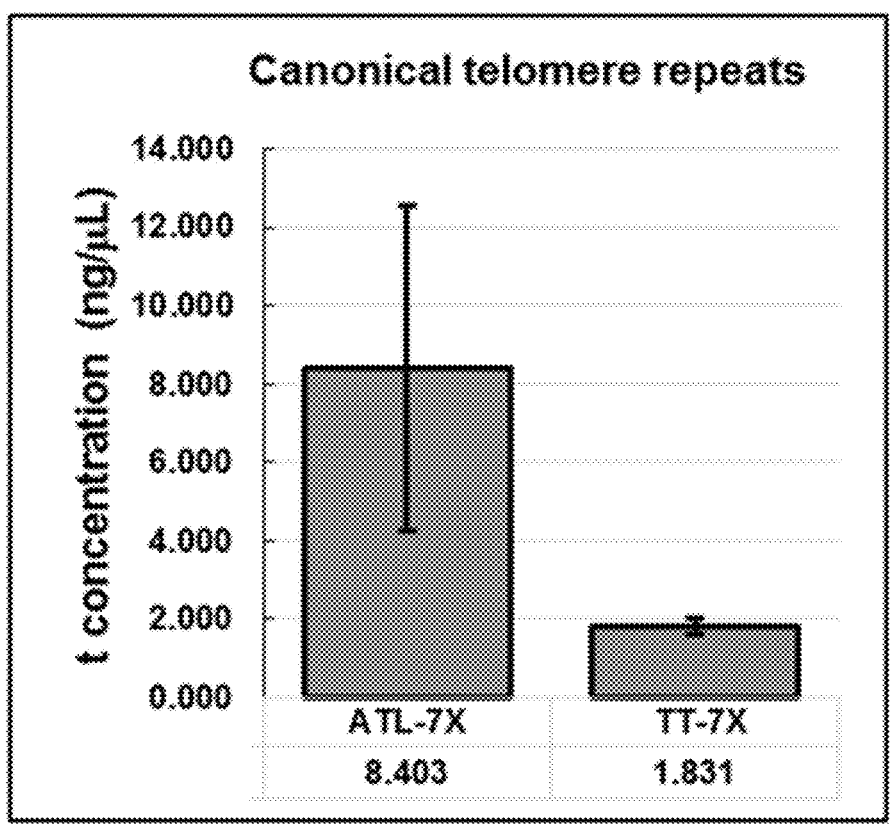

In the first set of experiments, the Tel-repeat/telomere ultramer representing the "true" telomere template was used (SEQ ID NO: 28). As shown above, it is made up of 15 repeats of the canonical CCCTAA telomere sequence. Evaluation of nine replicates using the disclosed triplex qPCR assay showed a consistent 'T' concentration greater than that seen in the Cawthon 2002 assay (see FIG. 13A). It should be noted that the initial (1×) ultramer DNA concentration (1.67 ng/μL) was calculated to mimic an average genomic telomere length of 3 kb. The difference was magnified when using a seven-fold higher concentration of the template ((11.69 ng/μL; see FIG. 13B). At the initial ultramer DNA concentration, the average T concentration of nine Tel-repeat replicates under the disclosed conditions described herein above, using the disclosed triplex qPCR assay was determined using the assay to be 0.15 ng/μL (see FIG. 13C). In contrast, under the conditions of the Cawthon 2002 assay, the T concentration was determined to be 0.11 ng/μL using IX template concentration (FIG. 13C). However, when the ultramer DNA concentration was increased to 7×, the average T concentration were, respectively, 8.40 ng/μL and 1.83 ng/μL, for the disclosed triplex qPCR assay and the Cawthon 2002 assay (see FIG. 13D). These data suggest that the tel G modified and tel C modified primers have greater specificity for the canonical telomere repeats than the TeloTest primers.

Example 20—Primer Impact on Quantitation of G-Rich Telomere-Like Sequences

Figure 14A:
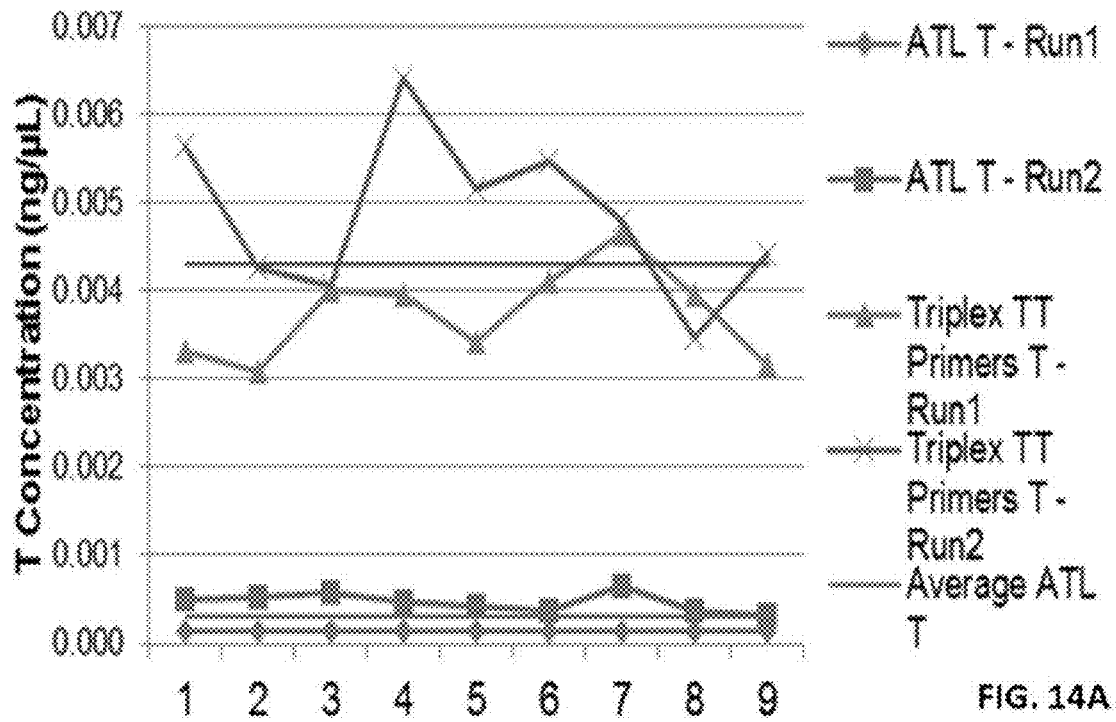
FIGS. 14A-14C shows a similar experiment to that described above for FIGS. 13A-13D. The amplification reactions were carried under the same conditions, except that the target template was a G-rich target sequence, $(CCCTCA)_{15}$. Reactions containing the Tel 1b and Tel 2b primers are indicated with "TT" in the figures, and reactions containing the Tel G modified and Tel C modified primers are indicated with "ATL" in the figures.
Figure 14B:
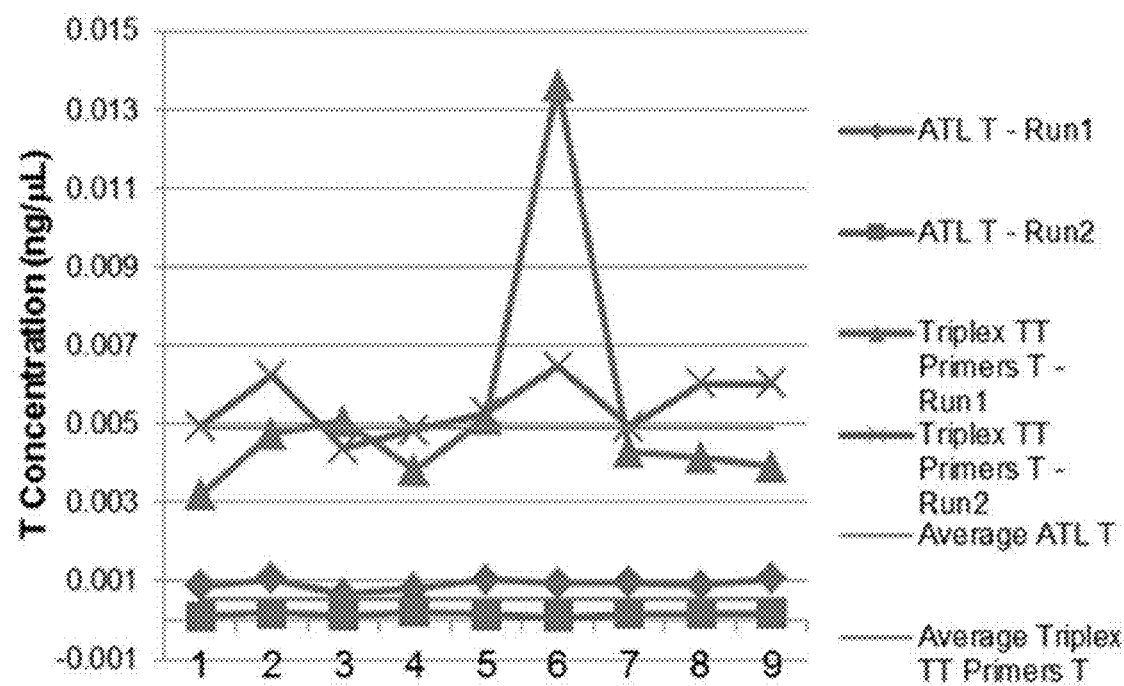
Figure 14C:
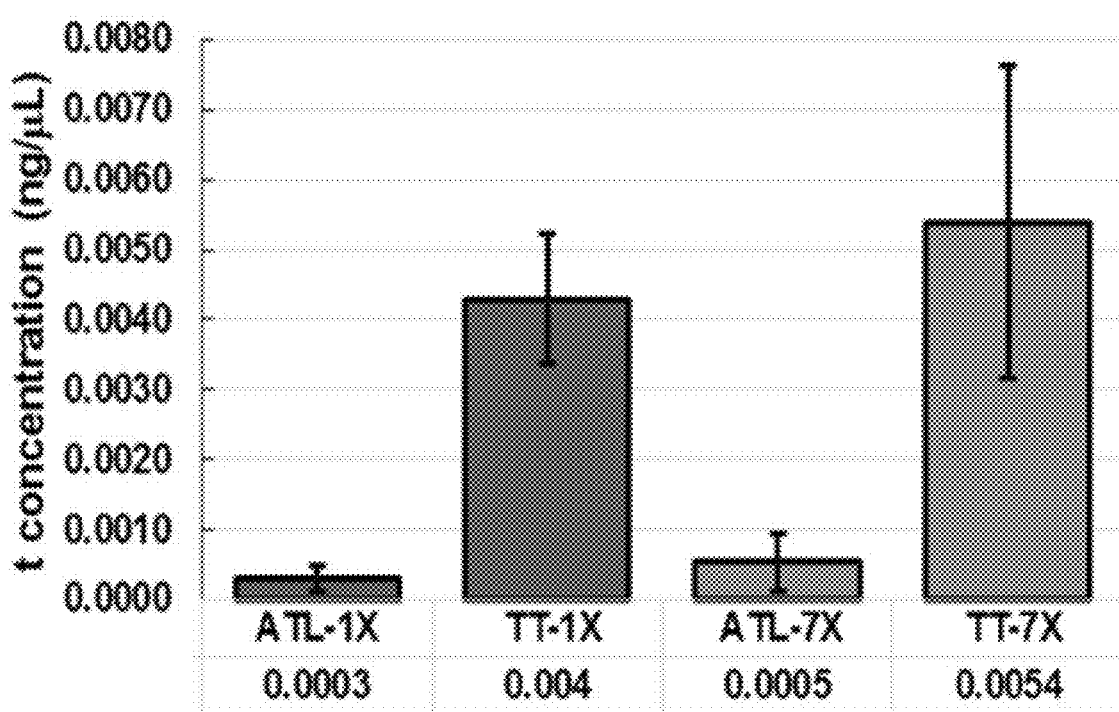

To represent one of the most common variant repeats found in the telomere associated region located immediately proximal to the canonical telomere repeats, the G-rich variant/degenerate1 ultramer was used (SEQ ID NO: 29). As described above, this ultramer sequence is made up of 15 repeats of CCCTCA sequence. Using the Cawthon 2002 primers in the disclosed triplex qPCR assay resulted in ten-fold excess amplification of the G-rich template compared to using the Tel G modified and Tel C modified primers at the IX (see FIG. 14A) and 7× (see FIG. 14B) template concentration. The IX and 7× template concentration (1.67 and 11.69 ng/μL, respectively), have the same meaning as described in the immediately preceding example. The average T concentration of nine G-rich variant replicates under the Cawthon 2002 assay conditions was 4.30×10$^{-3}$ ng/μL, in contrast, using the disclosed triplex qPCR assay yielded a T concentration of 3.06×10$^{-4}$ ng/μL (see FIG. 14C). Similar values were seen when the template concentration was increased to 7×, i.e. 4.90×10$^{-3}$ ng/μL and 5.34×10$^{-4}$ ng/μL for the Cawthon 2002 assay and the disclosed triplex qPCR assay, respectively (see FIG. 14C). These data indicate that the tel G modified and tel C modified primers of the present invention do not use the G-rich variant repeat sequence, TGAGGG, as a template for amplification. Additionally, these data, taken with the data in the preceding example, suggest that the tel G modified and tel C modified primers of the present invention have greater specificity for the canonical telomere repeats.

Example 21—Primer Impact on Quantitation of C-Rich Telomere-Like Sequences

Figure 15A:
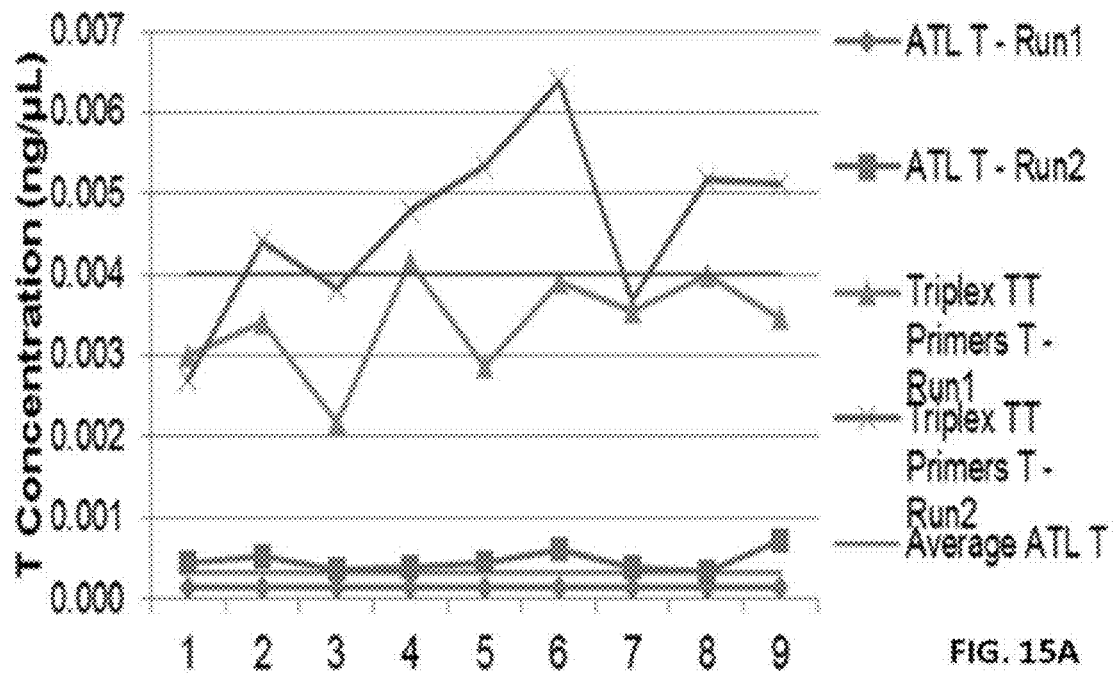
FIGS. 15A-15C shows a similar experiment to that described above for FIGS. 13A-13D. The amplification reactions were carried under the same conditions, except that the target template was a G-rich target sequence, $(CCCTGA)_{15}$. Reactions containing the Tel 1b and Tel 2b primers are indicated with "TT" in the figures, and reactions containing the Tel G modified and Tel C modified primers are indicated with "ATL" in the figures.
Figure 15B:
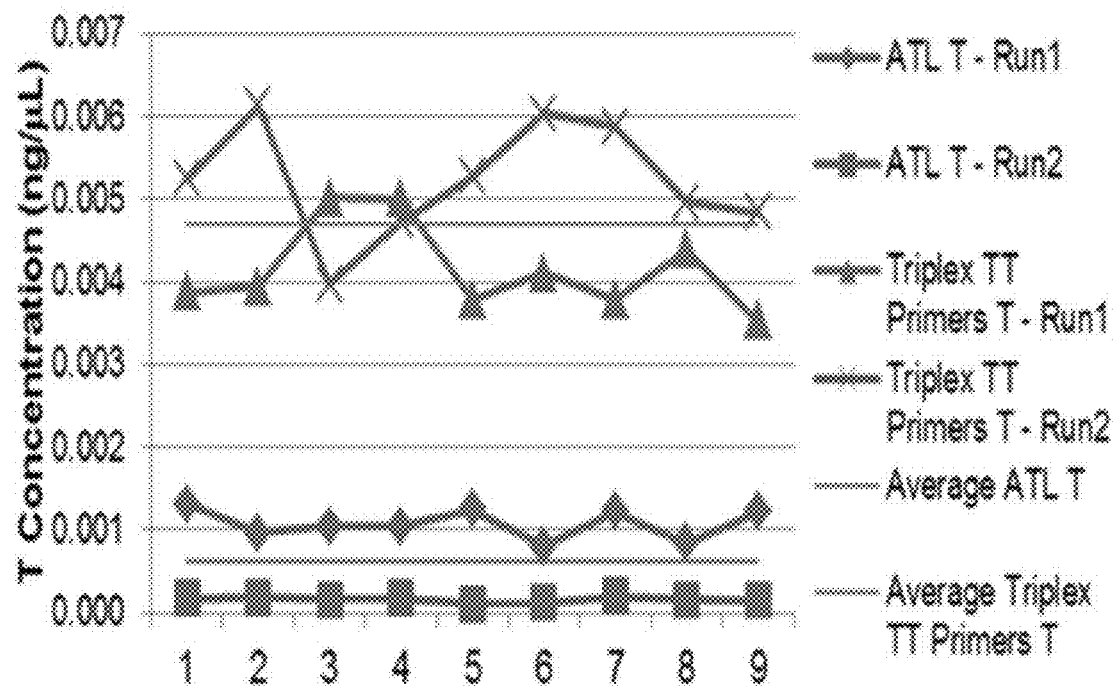
Figure 15C:
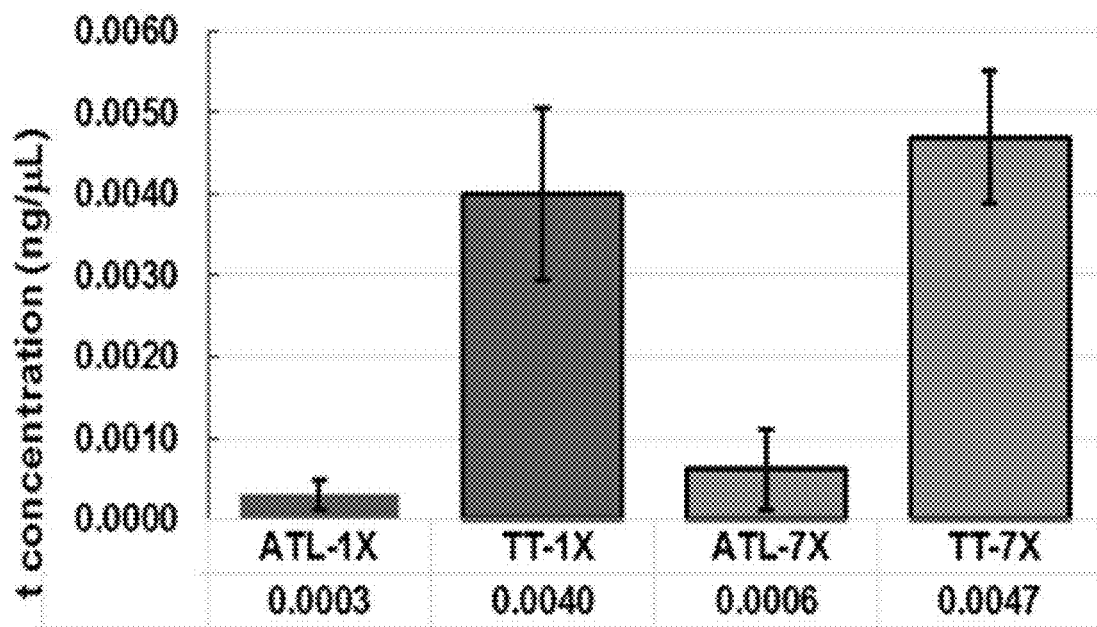

Another of the common variant repeats found in the telomere associated region is the C-rich variant, which is comprised of CCCTGA sequence, represented by the C-rich variant/degenerate2 ultramer (SEQ ID NO: 30). Similar to the data produced using the G-rich variant as a template, the Cawthon 2002 assay resulted in a 10-fold excess amplification of the C-rich template compared to the disclosed triplex qPCR assay at the IX (see FIG. 15A) and 7× (see FIG. 15B) template concentration. The average T concentration of nine C-rich variant replicates using the Cawthon 2002 assay was 3.99×10$^{-3}$ ng/μL, whereas, in contrast, the disclosed triplex qPCR assay provided a T concentration of 3.06×10$^{-4}$ ng/μL (see FIG. 15C). Similar values were seen when the template concentration was increased to 7×, 4.69×10$^{-3}$ ng/μL and 6.18×10$^{-4}$ ng/μL for the Cawthon 2002 assay and the disclosed triplex qPCR assay, respectively (see FIG. 15C). These data indicate that the tel G modified and tel C modified primers of the present invention do not use the C-rich variant repeat sequence, TCAGGG, as a template for amplification. These data further demonstrate that the tel G modified and tel C modified primers of the present invention have greater specificity for the canonical telomere repeats.

Based on the data generated in this example and the preceding two examples, it can be concluded that the Tel1b and Tel2b primers amplify typical telomere variant repeats at a much higher level than the tel G modified and tel C modified primers of the present invention. Moreover, these data suggest that the variant repeats are likely to contribute to higher T/S ratios reported by the Cawthon 2002 assay. Collectively these data surprisingly show that the el G modified and tel C modified primers of the present invention more specifically amplify canonical telomere repeats.

Example 22—Reproducibility and Precision

A multi-day, multi-operator study evaluating the total variability of the disclosed triplex qPCR assay of the present invention for measuring telomeric length was performed. Specifically, each of 40 whole blood donor samples was assayed in triplicate, on the same run by a single operator. The T/S ratio was calculated for each of the 3 replicates, providing estimates of the within run variance. The same assay/plate arrangement was then repeated over 20 days, once in the morning and once in the evening, using 3 different operators, for a total of 24 plate repeats. Twenty-four (24) average telomere length ("ATL") assays were performed, 12 ATL assays for samples 1-20 and 12 ATL assays for samples 21-40. Each sample's measurements, from the multiple runs, were analyzed using a random effects model with "run" being the random effect. Estimates of within, between and total run variability were obtained and the results are given below in Table 17.

TABLE 17

|  | Cawthon* | Disclosed Triplex Assay** |
|---|---|---|
| Intra-assay Precision (T/S ratio) | 4.7% | 3.2% |
| Total error/reproducibility | 11.2% | 6% |

*Cawthon 2002 assay using the Tel1b and Tel2b primers.
**Assay of the present invention using the tel C modified and tel G modified primers with the RNase P and B2M primers and probes as described herein above.

The foregoing results demonstrate the superiority of the disclosed triplex qPCR assay for use in clinical settings. For example, in any clinical use of quantitation of T/S ratio, e.g., to assess the correlation of T/S to a given disease, there will a threshold cut-off at a specific T/S ratio to discern differences in a between a healthy and a 'diseased' individual or population of individuals, or between subjects or populations that need to be treated differently (e.g., administered different drugs or therapeutic agents, treatments, or dosage levels). Accordingly, the reproducibility of the assay method around this cut-off defines the individuals or populations which will unequivocally fall into either the healthy or the at risk population, or need specific treatments. It will be understood that the lower the CV/total error for a given test method, the more reproducible will be results reported using that method. In the foregoing, the 6% total error/reproducibility observed for the disclosed triplex qPCR assay is 6/11, or roughly two-fold enhanced reproducibility of the Cawthon 2002 assay. Thus, the clinical utility of the disclosed triplex qPCR assay will be enhanced by approximately this same amount, due to the narrower 'indeterminate' zone, and as a consequence, more patients will be definitively reported as either a healthy or a diseased sample, or needing specific treatments.

Example 23—Improved Amplification Efficiencies

Amplification efficiency refers to how close the template amplification is to the theoretical maximum (100%), which is an exact doubling of the concentration of the amplicon template during each qPCR cycle. With the Cawthon 2002 (TeloTest assay), amplification efficiencies for the telomere and the single copy gene amplicons were typically in the 70-80%, and 85-95% range, respectively. In contrast, the qPCR efficiencies with the disclosed triplex qPCR assay for all three amplicons (i.e., the telomere amplicon and two different single copy gene amplicons) are typically in the 95-110% range, and often in the 98-101% range (see Tables 5 and 8). This represents a significant and unexpected improvement in quantitation of telomere length or telomere abundance over the TeloTest assay.

Figure 16:
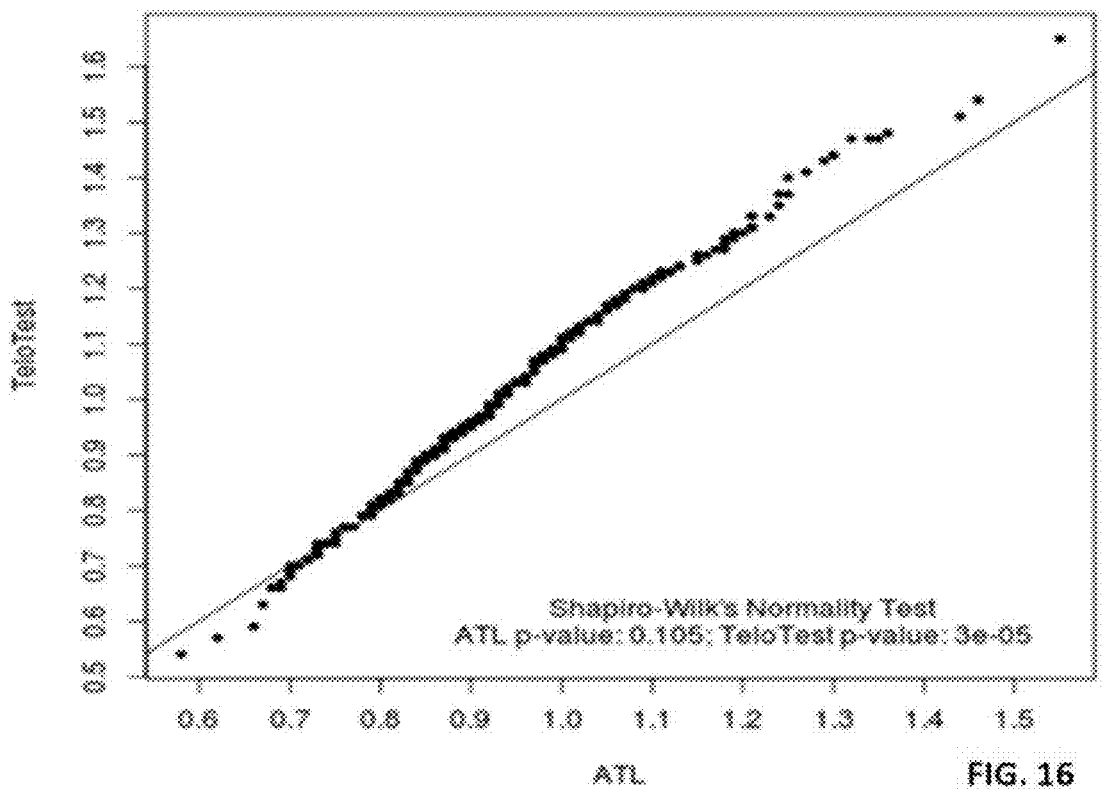
FIG. 16 shows a QQ Plot of T/S ratio data obtained from 311 normal human whole blood samples tested in the both the Cawthon 2002 assay and the disclosed triplex qPCR assay described herein. The best fit equation for the relationship between the T/S ratio obtained in the two assays was: $Y=1.13x-0.06$, with an $R^2=0.81$.

Example 24—Comparison of Methods with Normal Subject Population 311 normal human whole blood samples were tested in both the Cawthon 2002 assay and the disclosed triplex qPCR assay as described herein above. The observed T/S ratio for each assay was plotted and the data are shown in FIG. 16. The best fit equation for the relationship between the T/S ratio results for the two assays is:

$Y=1.13x-0.06 R2=0.81$.

The best fit equation yielded reasonable R2 and intercept values, but the slope of 1.13 shows that the Cawthon 2002 assay was reporting a higher T/S result than the more specific disclosed triplex qPCR assay. This is consistent with the results observed with the primer specificity described above. The difference between mean T/S ratios observed was statistically significant with a shift in T/S of 0.066 and a $\rho=4\times10^{-6}$, indicating that the difference in the assays is highly significant.

Additional analysis of the 313 normal blood sample results was performed to assess how statistically 'normal' the distribution of T/S ratio results was with each of the two methods. The distribution was assessed using Shapiro-Wild's Normality Test, in which a higher ρ-value reflects a more 'normal' distribution. The ρ-values determined for each of the two assay methods are shown below in Table 18, and surprisingly, they show a significantly improved normal distribution for the disclosed triplex qPCR assay.

TABLE 18

|  | ρ-value† | Normal distribution |
|---|---|---|
| Cawthon* | $3 \times 10^{-5}$ | Not normally distributed |
| Disclosed Triplex qPCR Assay** | 0.105 | Normally distributed |

*Cawthon 2002 assay using the Tel1b and Tel2b primers.
**Assay of the present invention using the tel C modified and tel G modified primers with the RNase P and B2M primers and probes as described herein above.

It will be apparent to those skilled in the art that various modifications and variations can be made in the present disclosure without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

SEQUENCES

Various nucleotide sequences, their name, and associated SEQ ID NO. are provided in Table 16 below.

TABLE 16

| SEQ ID NO. | Name | Sequence |
|---|---|---|
| 1 | Tel G modified | ACACCTCCTCCATGGTTTGGGTTTGGGT TTGGGTTTGGGTTAGTG |
| 2 | Tel C modified | TGTTAGCGACGCGATATCCCTATCCCTA TCCCTATCCCTAACA |
| 3 | β2 microglobulin forward primer | CCAGCAGAGAATGGAAAGTCAA |
| 4 | β2 microglobulin reverse primer | TCTCTCTCCATTCTTCAGTAAGTCAACT |
| 5 | β2 microglobulin probe | ATGTGTCTGGGTTTCATCCATCCGACA |
| 6 | RNaseP forward primer 1 | GTTCTCTGGGAACTCACCTCC |
| 7 | RNase P reverse primer 1 | ATGTCCCTTGGGAAGGTCTG |
| 8 | RNase P probe 1 | CCTAACAGGGCTCTCCCTGAG |
| 9 | RNaseP forward primer 2 | TGGCCCTAGTCTCAGACCTT |

TABLE 16-continued

| SEQ ID NO. | Name | Sequence |
|---|---|---|
| 10 | RNaseP reverse primer 2 | CGGAGGGAAGCTCATCAGTG |
| 11 | RNaseP probe 2 | CTGAGTGCGTCCTGTCAC |
| 12 | Y3 Clone | CCTAACCTAACCCTAACCCTAACCCTAACCCTAACCCTAACCCTAACCCTAACCCTAACCCTAACCCTAACCCTAACCCTAACCCTAACCCTAACCCTAACCCTAACCCTAACCCTAACCCTAACCCTAACCCT |
| 13 | Core telomere repeat sequence | TTAGGG |
| 14 | Tel-4rp | TGCTCGGCCGATCTGGCATCCCTAACCCTAACCCTAACCCTAACC |
| 15 | SUS | GATGGATCCTGAGGGTGAGGGTGAGGG |
| 16 | M13 forward | GTTGTAAAACGACGGCCAGT |
| 17 | M13 reverse | TCACACAGGAAACAGCTATGA |
| 18 | TeloAnchor Primer | TGCTCGGCCGATCTGGCATC |
| 19 | TeloProbe | CCCTAACCCTAACCCTAACCCTAA |
| 20 | Telotest primer Tel1b | CGGTTTGTTTGGGTTTGGGTTTGGGTTTGGGTTTGGGTT |
| 21 | Telotest primer Tel2b | GGCTTGCCTTACCCTTACCCTTACCCTTACCCTTACCCT |
| 22 | PGK1-Forward | AAGGGAAGCGGGTCGTTATG |
| 23 | PGK1-Reverse | GCAGAATTTGATGCTTGGGAC |
| 24 | ACTB-Forward | TCACCATTGGCAATGAGCG |
| 25 | ACTB-Reverse | TGGAGTTGAAGGTAGTTTCGTG |
| 26 | GAPDH-Forward | TGGACCTGACCTGCCGT |
| 27 | GAPDH-Reverse | TGGAGGAGTGGGTGTCGC |
| 28 | Tel-repeat Ultramer | $(CCUTAA)_{15}$ |
| 29 | G-rich variant-degenerate 1 | $(CCCTCA)_{15}$ |
| 30 | C-rich variant-degenerate 2 | $(CCCTGA)_{15}$ |

---

What is claimed is:

1. A method for determining average telomere length or abundance, comprising:
   a) contacting a first target nucleic acid with a first primer set, a second target nucleic acid with a second primer set, and a third target nucleic acid target with a third primer set;
      i. wherein the first primer set comprises a first forward primer and a first reverse primer; wherein the first forward primer comprises the sequence of SEQ ID NO: 1; and wherein the first reverse primer comprises the sequence of SEQ ID NO: 2;
      ii. wherein the second primer set comprises a second forward primer and a second reverse primer;
      iii. wherein the third primer set comprises a third forward primer and a third reverse primer; and
      iv. wherein the first target nucleic acid comprises a telomere repeat sequence;
   b) amplifying by polymerase chain reaction the first target nucleic acid with the first primer set to form a first amplicon, the second target nucleic acid with the second primer set to form a second amplicon, and the third target nucleic acid with the third primer set to form a third amplicon;
   c) determining during the polymerase chain reaction the amount of the first, second, and third amplicons;
      i. wherein the first amplicon is detected using a first detection label;
      ii. wherein the second amplicon is detected using a second detection label; and
      iii. wherein the third amplicon is detected using a third detection label; and
   d) determining the average length or abundance of telomeric DNA in the sample, wherein the average length or abundance of telomeric DNA in the sample is determined by: i) determining a concentration of the first, second and third amplicon by comparison to a control polymerase reaction; (ii) determining a ratio of the concentration of the first amplicon to an average concentration of the second and third amplicons; and (iii) converting the ratio from step (ii) to base pairs of telomere sequence per genome.

2. The method of claim 1, wherein each of the first forward primer and a first reverse primer comprise:
   a) a 3' portion that hybridizes to a telomeric repeat sequence under annealing conditions; and
   b) a 5' portion having an anchor sequence that does not hybridize to a telomeric repeat sequence.

3. The method of claim 1, wherein the first reverse primer is a mismatch primer comprising at least one mismatched nucleotide adjacent to or including the 3' end of the primer; and wherein the at least one mismatched nucleotide is not complementary to the target nucleic acid.

4. The method of claim 1, wherein the first reverse primer is blocked from priming the first target nucleic acid.

5. The method of claim 4, wherein the first reverse primer is blocked from priming the first target nucleic acid by a terminal 3' mismatched base.

6. The method of claim 1, wherein the second target nucleic acid is within a gene of known copy number.

7. The method of claim 6, wherein the gene of known copy number is a low copy number gene.

8. The method of claim 6, wherein the second target nucleic acid is a single copy number gene.

9. The method of claim 1, wherein the second forward primer comprises SEQ ID NO.: 3; and wherein the second reverse primer comprises SEQ ID NO: 4.

10. The method of claim 1, wherein each of the first detection label, second detection label, and third detection label independently comprise fluorogenic moieties; and wherein each of the fluorogenic moieties is detectable separably and simultaneously.

11. The method of claim 10, wherein the second detection label further comprises an oligonucleotide comprising the sequence of SEQ ID NO: 5.

12. The method of claim 1, wherein the second amplicon is from about 50 to about 250 bp in length; and wherein the third amplicon is from about 50 to about 250 bp in length.

13. The method of claim 1, further comprising the step of obtaining a chromosomal DNA sample prior to contacting the first, second, and third target nucleic acids with the first, second, and third primer sets, respectively; and wherein the chromosomal DNA sample comprises the first, second, and third target nucleic acids.

14. The method of claim 13, wherein the step of obtaining a chromosomal DNA sample comprises isolating one or more cell type from a fluid sample obtained a subject; and wherein the cell type isolated comprise circulating tumor cells, circulating stem cells, lymphocytes, granulocytes, myeloid cells, neutrophils, monocytes, macrophages, platelets, and leukocytes.

15. The method of claim 1, wherein the concentration of first, second, and third amplicon are determined by comparison to a control reference DNA.

16. The method of claim 1, wherein determining the average length or abundance of the first amplicon comprises the steps:
   a) determining the concentration of the first, second, and third amplicon by comparison to a control polymerase chain reaction;
   b) determine the ratio of the concentration of the first amplicon to the average or weighted concentration of the second and third amplicons; and
   c) converting the ratio from step (b) to base pairs of telomere sequence per genome.

* * * * *